(12) United States Patent
Scherz et al.

(10) Patent No.: US 9,452,172 B2
(45) Date of Patent: Sep. 27, 2016

(54) (BACTERIO)CHLOROPHYLL PHOTOSENSITIZERS FOR TREATMENT OF EYE DISEASES AND DISORDERS

(75) Inventors: Avigdor Joshua Scherz, Rehovot (IL); Yoram Salomon, Rehovot (IL); Arie Marcovich, Rehovot (IL); Alexander Brandis, Rehovot (IL); Daniel Wagner, Rehovot (IL)

(73) Assignee: Yeda Research and Development Co. LTD., Rehovot (IL)

( * ) Notice: Subject to any disclaimer, the term of this patent is extended or adjusted under 35 U.S.C. 154(b) by 0 days.

(21) Appl. No.: 14/240,328

(22) PCT Filed: Aug. 23, 2012

(86) PCT No.: PCT/IL2012/050325
§ 371 (c)(1),
(2), (4) Date: Jul. 21, 2014

(87) PCT Pub. No.: WO2013/027222
PCT Pub. Date: Feb. 28, 2013

(65) Prior Publication Data
US 2014/0378888 A1 Dec. 25, 2014

Related U.S. Application Data

(60) Provisional application No. 61/526,414, filed on Aug. 23, 2011.

(51) Int. Cl.
| | | |
|---|---|---|
| C07D 487/22 | (2006.01) |
| A61K 31/555 | (2006.01) |
| A61K 31/407 | (2006.01) |
| A61K 41/00 | (2006.01) |

(52) U.S. Cl.
CPC .......... *A61K 31/555* (2013.01); *A61K 31/407* (2013.01); *A61K 41/0071* (2013.01)

(58) Field of Classification Search
CPC .................................................. C07D 487/22
See application file for complete search history.

(56) References Cited

U.S. PATENT DOCUMENTS 5,756,541 A * 5/1998 Strong et al. ................. 514/502
7,947,672 B2 5/2011 Scherz et al.

FOREIGN PATENT DOCUMENTS

| WO | WO 03/028628 | 4/2003 |
| WO | WO 2005/120573 | 12/2005 |
| WO | WO 2008/052081 | 5/2008 |

OTHER PUBLICATIONS

Ashur et al., "Photocatalytic generation of oxygen radicals by the water-soluble bacteriochlorophyll derivative WST11, noncovalently bound to serum albumin," Journal of Physical Chemistry, 113:8027-8037 (2009).
Berdugo et al. "Evaluation of the new photosensitizer stakel (WST-11) for photodynamic choroidal vessel occlusion in rabbit and rat eyes," Investigative Ophthalmology and Visual Science, 49:1633-1644 (2008).
Bourges et al., "PDT of corneal neovessels using a new hydrosoluble photosensitizer (WST11)," Acta Ophthalmol Scand., 84 (S 239:41):352 (2006).
Brandis et al., "Novel water-soluble bacteriochlorophyll derivatives for vascular-targeted photodynamic therapy: synthesis, solubility, phototoxicity, and the effect of serum proteins," Photochem Photobiol., 81:983-993 (2005).
Ciulla et al., "MV-6401, a potent photosensitizer in experimental animal models: a review of this agent and the current state of photosensitizing agents for the treatment of exudative age-related macular degeneration," Drugs of the Future, 30(10):1031-1037 (2005).
Gohto et al., "Photodynamic effect of a new photosensitizer ATx-S10 on corneal neovascularization," Experimental Eye Research, 67(3):313-322 (1998).
Hafezi et al., "Corneal collagen crosslinking with riboflavin and ultraviolet A to treat induced keratoectasia after laser in situ keratomileusis," J Cataract Refract Surg., 33:2035-2040 (2007).
Hafezi et al., "Collagen crosslinking with ultraviolet-A and hypoosmolar riboflavin solution in thin corneas," J Cataract Refract Surg., 35:621-624 (2009).
Mazor et al., "WST11, A novel water-soluble bacteriochlorophyll derivative; cellular uptake, pharmacokinetics, biodistribution, and vascular targeted photodynamic activity against melanoma tumors," Photochem Photobiol., 81:342-345 (2005).
Raiskup-Wolf et al., "Collagen cross-linking with riboflavin and ultraviolet-A light in keratoconus: long-term results," J Cataract Refract Surg., 34:796-801 (2008).
Spoerl et al., "Safety of UVA-riboflavin cross-linking of the cornea," Cornea, 26:385-389 (2007).
Van Tenten et al., "A preliminary study on the prevention of posterior capsule opacification by photodynamic therapy with bacteriochlorin a in rabbits," Ophthalmic Research, 34(3):113-118 (2002).
Wollensak et al., "Corneal endothelial cytoxicity of riboflavin/UVA treatment in vitro," Ophthalmic Res., 35:324-328 (2003).
Wollensak et al., "Endothelial cell damage after riboflavin-ultraviolet-A treatment in the rabbit," J Cataract Refract Surg., 29:1786-1790 (2003).
Wollensak et al., "Riboflavin/ultraviolet-A-induced collagen crosslinking for the treatment of keratoconus," Am J Ophthalmol, 135:620-627 (2003).
Wollensak et al., "Keratocyte apoptosis after corneal collagen cross-linking using riboflavin/UVA treatment," Cornea., 23:43-49 (2004).
Wollensak et al., "Keratocyte cytotoxicity of riboflavin/UVA-treatment in vitro," Eye, 18:718-722 (2004).

(Continued)

*Primary Examiner* — Brian McDowell
(74) *Attorney, Agent, or Firm* — Dechert LLP

(57) ABSTRACT

An ophthalmic composition is provided, comprising chlorophyll or bacteriochlorophyll compounds for photodynamic treatment (PDT) of diseases, disorders and conditions associated with corneal or scleral anomalies, such as corneal thinning and scleral stretching.

5 Claims, 20 Drawing Sheets

(56) References Cited

OTHER PUBLICATIONS

Wollensak, "Histological changes in human cornea after cross-linking with riboflavin and ultraviolet A," Letter to the editor. Acta Ophthalmol., 88:e17-18 (2010).

Wollensak et al., "Significance of the riboflavin film in corneal collagen crosslinking," J Cataract Refract Surg., 36:114-120 (2010).
Yoon et al., "Photodynamic Therapy with Verteporfin for Corneal Neovascularization," American Journal of Ophthalmology, 144(3):390-395 (2007).

\* cited by examiner

Gauss

Gauss

(BACTERIO)CHLOROPHYLL PHOTOSENSITIZERS FOR TREATMENT OF EYE DISEASES AND DISORDERS

CROSS REFERENCE TO RELATED APPLICATIONS

This application is a National Stage of International Application No. PCT/IL2012/050325, filed Aug. 23, 2012, which claims the benefit under 35 U.S.C. §119(e) of U.S. Provisional Application No. 61/526,414, filed Aug. 23, 2011, the contents of all of which are incorporated herein in their entireties by reference thereto.

TECHNICAL FIELD

The present invention is in the fields of ophthalmology and photodynamic therapy (PDT) and relates to photodynamic therapy of diseases, disorders and conditions associated with corneal or scleral anomaly, using photosensitizers, particularly water-soluble chlorophyll and bacteriochlorophyll compounds.

BACKGROUND ART

Treatment with riboflavin (RF) followed by ultraviolet A (UVA, 370 nm) illumination results in cornea stiffening and sclera stiffening presumably because of collagen crosslinking (CXL). This has increasingly been used for halting the progression of keratoconus and post refractive laser surgery corneal ectasia (Wollensak et al., 2003(a); Hafezi et al., 2007; Raiskup-Wolf et al., 2008). However, there are several drawbacks to this treatment: (1) The prolonged time of RF treatment (30 min); (2) The prolonged eye exposure to UVA irradiation (30 min), and finally (3) Toxicity to keratocytes (Wollensak et al., 2004(a); Wollensak et al., 2004(b); Wollensak, 2010(a)) and corneal endothelial cells (Wollensak et al., 2003(c); Spoerl et al. 2007), making treatment of corneas thinner than 400 microns problematic (Hafezi et al., 2009; Wollensak, 2010(b)). Hence, there is a need for a safer treatment that can stiffen the cornea with a lesser risk to the patient (Avila and Navia, 2010; WO/2008/052081). One possibility is to use photosensitizers that inflict cornea stiffening upon illumination at the near infra red (NIR) using bacteriochlorophyll derivatives as photosensitizers.

Myopia, also termed nearsightedness is a refractive defect of the eye in which collimated light produces the image focus in front of the retina when accommodation is relaxed. The global prevalence of myopia has been estimated from 800 million to 2.3 billion. In some countries, such as China, India and Malaysia, up to 41% of the adult population is myopic to −1 dpt and about 80% to −0.5 dpt. Myopia has been related with stretching of the collagenous sclera. Elongation of the globe occurs in the posterior segment of the globe and involves the sclera. Such globe elongation causes myopic progression in predisposed myopic children and adolescents. It usually slows down and stops during the third decade of life, when maturation of body tissues occurs with natural stiffening. This stiffening is related to glycation mediated cross linking.

At present, there is no effective treatment to stop myopic progression and reduce visual loss caused by degenerative myopia. Surgical solutions to arrest myopic progression by applying reinforcement belts around the eye, and suturing them to the sclera, were reported. These surgical solutions were controversial and technically challenging, and did not gain popularity. The critical age of intervention is during childhood or early adolescence. Thus, a simpler approach to stiffen the sclera should be applied.

Since progression of myopia is associated with elongation of the posterior segment of the eye and subsequent stretching of the sclera and chorioretinal tissues, stiffening of the sclera by collagen crosslinking, is expected to retard/stop the progression of the disease and related disorders such as macular stretching and atrophy or bleeding and visual loss. Wollensak and Spoerl reported the use of RF/UVA treatment to achieve such crosslinking and strengthening in human and porcine sclera in vitro. The crosslinking stiffening was demonstrated in vivo on rabbits, and was shown to last several months. This treatment can be applied to arrest myopic progression.

However, such treatment is subjected to the UVA risks which might be hazardous. In addition, the tissue penetration of UV radiation is limited. Illumination of the sclera with UV requires external approach and necessitates surgical exposure. There is therefore, a need for alternative photosensitizers that can induce collagen crosslinking with a safer and better penetrating wavelength at the red or near infrared (NIR).

A non hazardous light with deeper tissue penetration, like NIR in bacteriochlorophyll (BChl)-based PDT has been shown to provide efficient and safe anti-cancer treatments in oncology and age related macular degeneration in the eye (AMD) (U.S. Pat. No. 7,947,672, WO 2005/120573).

Application of novel water soluble chlorophyll (Chl) and bacteriochlorophyll (BChl) derivatives as sensitizers in PDT has been reported by the present inventors in recent years (U.S. Pat. No. 7,947,672; WO 2005/120573; Ashur et al. 2009; Mazor et al. 2005; Brandis et al., 2005) and by others (Moore et al., 2009; Bourges et al., 2006; Berdugo et al. 2008). Upon NIR illumination these water soluble derivatives generate $O_2^-$ and .OH radicals (Ashur et al. 2009; Mazor et al. 2005; Brandis et al., 2005; Vakrat-Haglili et al., 2005) and have been used so far in vascular-targeted photodynamic therapy (VTP) of cancers in preclinical (Mazor et al. 2005) and advanced clinical trials of prostate cancer therapy (currently in Phase III) (Trachtenberg J et al. 2007; Lepor H. 2008; Moore et al., 2009), following i.v. administration to the treated patients. The effective generation of oxygen radicals as precursors of protein crosslinking (Liu et al., 2004), and the clinical experience established with water soluble Bchls and Chls derivatives, makes these sensitizers potential candidates for application in therapy that is mediated by collagen crosslinking, particularly corneal and scleral stiffening upon NIR illumination after topical application.

SUMMARY OF THE INVENTION

It has now been found in accordance with the present invention that the water soluble (bacterio)chlorophyll derivatives described in U.S. Pat. No. 7,947,672 and WO 2005/120573 enhance, upon NIR illumination, stiffening of the cornea and sclera of rabbit eye after topical application. Non-limiting exemplifying results are disclosed herein for ex vivo and in vivo treatment of rabbit eyes with certain water soluble sulfonated bacteriochlorophyll derivatives. Treatment of corneas and sclera of rabbit eyes with these photosensitizers appeared safe and increased significantly the biomechanical strength of the cornea and the sclera.

The present invention thus relates to the use of chlorophyll and bacteriochlorophyll derivatives for minimally invasive photodynamic therapy (PDT) of diseases, disorders and conditions associated with corneal or scleral anomaly, particularly with corneal thinning or scleral stretching.

In a main aspect, the present invention provides ophthalmic compositions for use in PDT of the eye comprising a (bacterio)chlorophyll derivative of the formula I, II or III herein, that significantly enhance corneal and scleral stiffening upon NIR irradiation.

In another aspect, the present invention relates to a method for treatment of eye diseases, disorders and conditions, particularly disorders associated with thinning of the cornea such as keratoconus, raised intraocular pressure and corneal ectasia caused by trauma, and disorders associated with eye globe elongation such as myopia and macular stretching.

The present invention further provides a method for preventing a corneal and/or scleral disease or weakening before, during or after interventional procedures.

DETAILED DESCRIPTION

Definitions and Abbreviations

Figure 1:
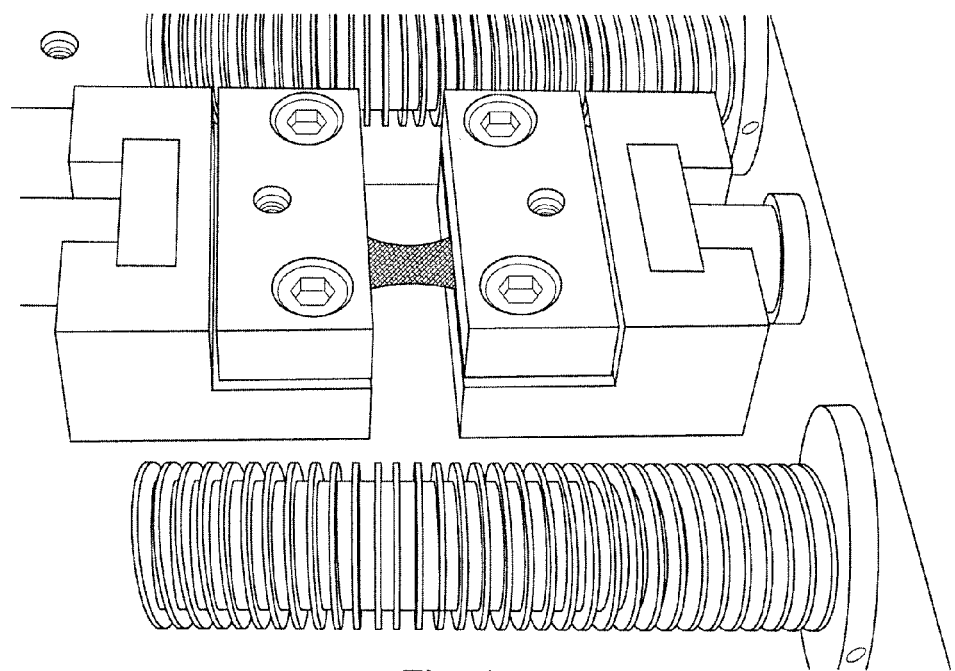
FIG. 1 is an illustration of a corneal strip clamped at a distance of 6 mm between the jaws of a microcomputer-controlled biomaterial tester.

Bchl a: bacteriochlorophyll a: pentacyclic 7,8,17,18-tetrahydroporphyrin with a 5$^{th}$ isocyclic ring, a central Mg atom, a phytyl or geranylgeranyl group at position 17$^3$, a COOCH$_3$ group at position 13$^2$, an H atom at position 13$^2$, methyl groups at positions 2, 7, 12, 18, an acetyl group at position 3, and an ethyl group at position 8, herein compound 1; Bphe: bacteriopheophytin a (Bchl in which the central Mg is replaced by two H atoms); Bpheid: bacteriopheophorbide a (the C-17$^2$-free carboxylic acid derived from Bphe without the central metal atom); Chl: chlorophyll; Rhodobacteriochiorin: tetracyclic 7,8,17,18-tetrahydroporphyrin having a -CH$_2$CH$_2$COOH group at position 17, a -COOH at position 13, methyl groups at positions 2, 7, 12, 18, ethyl group at position 8 and vinyl as position 3; Pd-Bpheid: Pd-bacteriopheophorbide a; WST 11: palladium $3^1$-oxo-15-methoxycarbonyl methyl-rhodobacteriochlonn $13^1$-(2-sulfoethyl) amide dipotassium salt; ROS: reactive oxygen species; NIR: near infrared; RF: riboflavin.

IUPAC numbering of the bacteriochlorophyll derivatives is used throughout the specification.

MODES FOR CARRYING OUT THE INVENTION

It has been found by the present inventors that certain water soluble chlorophyll and bacteriochlorophyll derivatives penetrate sclera and de-epithelialized cornea fairly fast and in a time dependent manner, and upon sensitization by the appropriate irradiation induce consistent and significant stiffening of the cornea and the sclera both ex vivo and in vivo. The fact that these photosensitizers were photochemically active was reflected in their continuous bleaching and spectra modification into their oxidized form during illumination.

Thus, it is a main object of the present invention to provide pharmaceutical compositions comprising a chlorophyll or bacteriochlorophyll photosensitizer for use in minimally invasive photodynamic therapy (PDT) of diseases, disorders and conditions associated with corneal or scleral anomaly. Particularly, the pharmaceutical composition provided by the invention is for treatment of corneal thinning and/or sclera stretching.

In preferred embodiments, the photosensitizer useful for the purpose of the invention is a water soluble (bacterio) chlorophyll of the formula I, II or III:

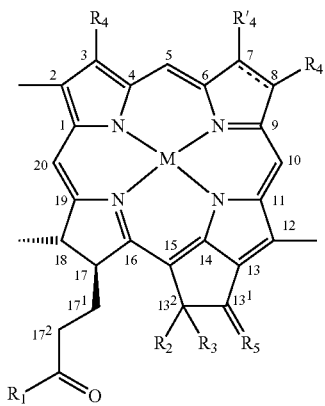

(I)

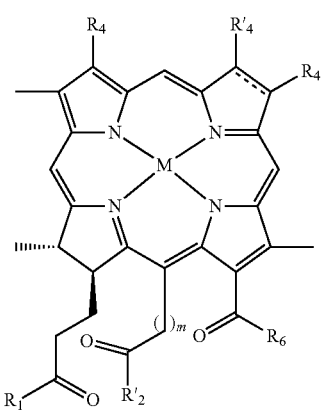

(II)

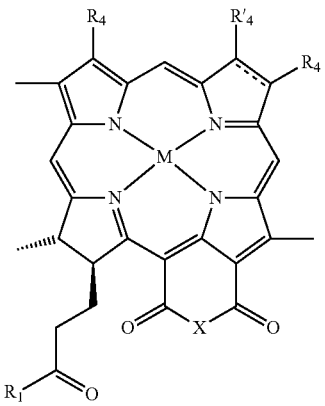

(III)

wherein

M represents 2H or an atom selected from the group consisting of Mg, Pd, Pt, Zn, In, Gd and Yb;

X is O or N—$R_7$;

$R_1$, $R'_2$ and $R_6$ each independently is Y—$R_8$, —$NR_9R'_9$ or —$N^+R_9R'_9R''_9A^-$;

Y is O or S;

$R_2$ is H, OH or $COOR_9$;

$R_3$ is H, OH, $C_1$-$C_{12}$ alkyl or $C_1$-$C_{12}$ alkoxy;

$R_4$ is —CH=$CR_9R'_9$, —CH=$CR_9$Hal, —CH=CH—$CH_2$—$NR_9R'_9$, —CH=CH—$CH_2$— $N^+R_9R'_9R''_9A^-$, —CHO, —CH=$NR_9$, —CH=$N^+R_9R'_9A^-$, —$CH_2$—$OR_9$, —$CH_2$—$SR_9$, —$CH_2$—Hal, —$CH_2$—$R_9$, —$CH_2$—$NR_9R'_9$, —$CH_2$—$N^+R_9R'_9R''_9A^-$, —$CH_2$—$CH_2R_9$, —$CH_2$—$CH_2$Hal, —$CH_2$—$CH_2OR_9$, —$CH_2$—$CH_2SR_9$, —$CH_2$—$CH_2$—$NR_9R'_9$, —$CH_2$—$CH_2$—$N^+R_9R'_9R''_9A^-$, —$COCH_3$, $C(CH_3)$=$CR_9R'_9$, —$C(CH_3)$=$CR_9$Hal, —$C(CH_3)$=$NR_9$, —$CH(CH_3)$=$N^+R_9R'_9A^-$, —$CH(CH_3)$—Hal, —$CH(CH_3)$—$OR_9$, —$CH(CH_3)$—$SR_9$, —$CH(CH_3)$—$NR_9R'_9$, —$CH(CH_3)$—$N^+R_9R'_9R''_9A^-$, or —C≡$CR_9$;

$R'_4$ is methyl or formyl;

$R_5$ is O, S, N—$R_9$, $N^+R_9R'_9A^-$, $CR_9R'_9$, or $CR_9$—Hal;

$R_7$, $R_8$, $R_9$, $R'_9$ and $R''_9$ each independently is:

(a) H;

(b) $C_1$-$C_{25}$ hydrocarbyl;

(c) $C_1$-$C_{25}$ hydrocarbyl substituted by one or more functional groups selected from the group consisting of halogen, nitro, oxo, OR, SR, epoxy, epithio, —CONRR', —COR, COOR", —$OSO_3R$, —$SO_3R''$, —$SO_2R$, —$NHSO_2R$, —$SO_2NRR'$, —NRR', =N—OR, =N—NRR', —C(=NR)—NRR', —NR—NRR', —(R)N—C(=NR)—NRR', O←NR—, >C=NR, —$(CH_2)_n$—NR—COR', —$(CH_2)_n$—CO—NRR', —O—$(CH_2)_n$—OR, —O—$(CH_2)_n$—O—$(CH_2)_n$—R, —PRR', —$OPO_3RR'$, —$PO_2HR$ and —$PO_3R''R''$, wherein n is an integer of 1 to 10 and R and R' each independently is H, hydrocarbyl or heterocyclyl, or R and R' together with the N atom to which they are attached form a 3-7 membered saturated ring optionally containing a further heteroatom selected from O, S and N, wherein the further N atom may be substituted, and R" is H, a cation, hydrocarbyl or heterocyclyl;

(d) $C_1$-$C_{25}$ hydrocarbyl substituted by one or more functional groups selected from the group consisting of positively charged groups, negatively charged groups, basic groups that are converted to positively charged groups under physiological conditions, and acidic groups that are converted to negatively charged groups under physiological conditions;

(e) $C_1$-$C_{25}$ hydrocarbyl containing one or more heteroatoms and/or one or more carbocyclic or heterocyclic moieties;

(f) $C_1$-$C_{25}$ hydrocarbyl containing one or more heteroatoms and/or one or more carbocyclic or heterocyclic moieties and substituted by one or more functional groups as defined in (c) and (d) above;

(g) $C_1$-$C_{25}$ hydrocarbyl substituted by a residue of an amino acid, a peptide, a protein, a monosaccharide, an oligosaccharide, or a polysaccharide; or (h) a residue of an amino acid, a peptide, a protein, a monosaccharide, an oligosaccharide, or a polysaccharide;

$R_7$ may further be —NRR', wherein R and R' each is H or $C_1$-$C_{25}$ hydrocarbyl, optionally substituted by a negatively charged group, preferably $SO_3^-$;

$R_8$ may further be $H^+$ or a cation $R^+_{10}$ when $R_1$, $R'_2$ and $R_6$ each independently is Y—$R_8$;

$R+_{10}$ is a metal cation, an ammonium group or an organic cation;

$A^-$ is a physiologically acceptable anion;

m is 0 or 1;

the dotted line at positions 7-8 represents an optional double bond; and pharmaceutically acceptable salts and optical isomers thereof.

In certain embodiments, the dotted line at positions 7-8 represents a double bond and the photosensitizer is a chlorophyll of the formula I, II or III.

The pentacyclic chlorophyll compound of formula I wherein M is Mg, $R_1$ at position $17^3$ is phytyloxy, $R_2$ at position $13^2$ is $COOCH_3$, $R_3$ at position $13^2$ is an H atom, $R_5$ is O, $R_4$ at position 3 is vinyl, the dotted line at positions 7-8 represents a double bond, $R'_4$ is methyl or formyl at position 7 and $R_4$ is ethyl at position 8, are chlorophyll a and b, respectively, and their derivatives will have a different metal atom and/or different substituents $R_1$, $R_2$, $R_3$, $R_4$, $R'_4$ and/or $R_5$.

The tetracyclic compound of formula II (three pyrroles and one pyrroline coupled through four methine linkages) wherein M is absent, $R_1$ at position $17^3$ is a propionic acid, $R'_2$ at position 15 is —$CH_2COOH$, $R_6$ at position $13^2$ is —COOH, $R_4$ at position 3 is vinyl, the dotted line at positions 7-8 represents a double bond, $R'_4$ is methyl at position 7 and $R_4$ is ethyl at position 8, is chlorin, and its derivatives will have different metal atoms and/or different substituents $R_1$, $R'_2$, $R_4$, $R'_4$ and/or $R_6$.

The pentacyclic compound of formula III wherein M is absent, X is oxygen, $R_1$ at position $17^3$ is a propionic acid, $R_4$ at position 3 is vinyl, the dotted line at positions 7-8 represents a double bond, $R'_4$ is methyl at position 7 and $R_4$ is ethyl at position 8 is purpurin-18, and its derivatives will have different metal atoms and/or different substituents $R_1$, $R_4$, $R'_4$, and/or X other than oxygen.

In certain other embodiments, the positions 7-8 are hydrogenated and the photosensitizer is a bacteriochlorophyll of the formula I, II or III. The pentacyclic compounds of formula I wherein M is Mg, $R_1$ at position $17^3$ is phytyloxy or geranylgeranyloxy, $R_2$ at position $13^2$ is $COOCH_3$, $R_3$ at position $13^2$ is an H atom, $R_5$ is O, $R_4$ at position 3 is acetyl and at position 8 is ethyl, and the dotted line at positions 7-8 is absent, is bacteriochlorophyll a (Bchla), and its optional derivatives will have different metal atoms and/or different substituents $R_1$, $R_2$, $R_3$, $R_4$, $R'_4$ and/or $R_5$.

The tetracyclic (two pyrroles and two pyrroline coupled through four methine linkages) compounds of formula II wherein M is absent, methyl groups at positions 2, 7, 12, 18, $R_1$ at position $17^3$ is propionic acid, $R'_2$ at position 13 is $COOCH_3$, $R_4$ at position 3 is acetyl and at position 8 is ethyl, and the dotted line at positions 7-8 is absent, is bacteriochlorin a. When a vinyl group is attached at positions 3, the compound is rhodobacteriochlorin (($3^1$-vinyl)-bacteriochlorin a). Derivatives of bacteriochlorin a and rhodobacteriochlorin will have different metal atoms and/or different substituents $R_1$, $R'_2$, $R_4$ at position 3 and/or $R_6$.

The pentacyclic compound of formula III wherein M is absent, X is oxygen, $R_1$ at position $17^3$ is a propionic acid, $R_4$ at position 3 is acetyl and at position 8 is ethyl, the dotted line at positions 7-8 is absent, is bacteriopurpurin-18, and its derivatives will have different metal atoms and/or different substituents $R_1$, $R_4$, $R'_4$ and/or X other than oxygen.

As used herein, the term "hydrocarbyl" means any straight or branched, saturated or unsaturated, acyclic or cyclic, including aromatic, hydrocarbyl radicals, of 1-25 carbon atoms, preferably of 1 to 20 or 1 to 10, more preferably 1 to 6, most preferably 2-3 carbon atoms. The hydrocarbyl may be a lower alkyl radical of 1-6, preferably of 1-4 carbon atoms, e.g. methyl, ethyl, propyl, isopropyl, butyl, isobutyl, tert-butyl, or alkenyl, alkynyl or cycloalkyl, or at the position 17 of the compounds of formula I, II or III, the hydrocarbyl is a radical derived from natural Chl and Bchl compounds, e.g. geranylgeranyl (2,6-dimethyl-2,6-octadienyl) or phytyl (2,6,10,14-tetramethyl-hexadec-14-en-16-yl).

In one embodiment, the alkyl group has 10 carbon atoms or more, e.g. —$C_{10}H_{21}$, —$C_{15}H_{31}$, —$C_{16}H_{33}$, —$C_{17}H_{35}$, —$C_{18}H_{37}$, —$C_{20}H_{41}$, and the like.

In another embodiment, the $C_1$-$C_{25}$ hydrocarbyl is a straight or branched $C_2$-$C_{25}$ alkenyl or alkynyl radical, preferably of 2-6 carbon atoms, e.g. vinyl, prop-2-en-1-yl, but-3-en-1-yl, pent-4-en-1-yl, hex-5-en-1-yl, ethynyl, propargyl, and the like.

In yet another embodiment, the $C_1$-$C_{25}$ hydrocarbyl is a $C_3$-$C_{25}$ monocyclic or polycyclic cycloalkyl or partially unsaturated cycloalkyl, preferably $C_3$-$C_{14}$, more preferably $C_3$-$C_7$ cycloalkyl, such as cyclopropyl, cyclobutyl, cyclopentyl, cyclohexyl and cycloheptyl.

The hydrocarbyl may further be aryl or aralkyl, wherein the term "aryl" as used herein refers to a "$C_6$-$C_{14}$" aromatic carbocyclic group having 6 to 14 carbon atoms, preferably 6 to 10 carbon atoms, consisting of a single, bicyclic or tricyclic ring system, such as phenyl, naphthyl, carbazolyl, anthryl, phenanthryl and the like, and the term "aralkyl" refers to a radical derived from an arylalkyl compound wherein the aryl moiety is preferably a $C_6$-$C_{14}$, more preferably a $C_6$-$C_{10}$ aryl such as benzyl, phenanthryl and the like.

The term "heterocyclic ring" or "heterocyclyl" means a radical derived from a saturated, partially unsaturated, optionally substituted, monocyclic, bicyclic or tricyclic heterocycle of 3-12, preferably 5-10, more preferably 5-6 members in the ring containing 1 to 3 heteroatoms selected from O, S and/or N. Particular examples are dihydrofuryl, tetrahydrofuryl, pyrrolynyl, pyrrolydinyl, dihydrothienyl, dihydropyridyl, piperidinyl, quinolinyl, piperazinyl, morpholino or 1,3-dioxanyl.

The terms "heteroaryl" or "heteroaromatic moiety" refer to a mono- or polycyclic heteroaromatic ring that may comprise both carbocyclic and heterocyclic rings, containing 1 to 3 heteroatoms selected from O, S and/or N and optionally substituted. Particular examples are, without being limited to, pyrrolyl, furyl, thienyl, pyrazolyl, imidazolyl, oxazolyl, thiazolyl, pyridyl, quinolinyl, isoquinolinyl, pyridazinyl, pyrimidinyl, pyrazinyl, 1,3,4-triazinyl, 1,2,3-triazinyl, 1,3,5-triazinyl, benzofuryl, isobenzofuryl, indolyl, imidazo[1,2-a]pyridyl, benzimidazolyl, benzthiazolyl, benzoxazolyl, benzodiazepinyl, and other radicals derived from further polycyclic heteroaromatic rings.

Any "carbocyclyl", "heterocyclyl", "aryl" or "heteroaryl" may be substituted by one or more radicals such as halogen, $C_6$-$C_{14}$ aryl, $C_1$-$C_{25}$ alkyl, nitro, OR, SR, —COR, —COOR, COOR", —SO$_3$R, —SO$_3$R", —SO$_2$R, —NHSO$_2$R, —NRR', —(CH$_2$)$_n$—NR—COR', and —(CH$_2$)$_n$—CO—NRR', wherein n, R, R' and R" are as defined above. It is to be understood that when a polycyclic heteroaromatic ring is substituted, the substitutions may be in any of the carbocyclic and/or heterocyclic rings.

The term "alkoxy" as used herein refers to a group ($C_1$-$C_{25}$)alkyl-O—, wherein $C_1$-$C_{25}$ alkyl is as defined above. Examples of alkoxy are methoxy, ethoxy, n-propoxy, isopropoxy, butoxy, isobutoxy, tert-butoxy, pentoxy, hexoxy, —OC$_{12}$H$_{25}$, —OC$_{15}$H$_{31}$, —OC$_{16}$H$_{33}$, —OC$_{17}$H$_{35}$, —OC$_{18}$H$_{37}$, and the like. The term "aryloxy" as used herein refers to a group ($C_6$-$C_{18}$)aryl-O—, wherein $C_6$-$C_{18}$ aryl is as defined above, for example, phenoxy and naphthoxy.

The term "halogen", as used herein, refers to fluoro, chloro, bromo or iodo.

The hydrocarbon chain of $R_7$, $R_8$, $R_9$, $R'_9$ and/or $R''_9$ may optionally contain one or more heteroatoms such as O, S and/or NH, and/or one or more carbocyclic rings or heterocyclic ring moieties, wherein "carbocyclic" as used herein encompasses cycloalkyl and aryl as defined herein. In one embodiment, the hydrocarbyl chain contains one or more O atoms and has a OH end group as represented by an oligooxyethyleneglycol residue of 4 to 10 carbon atoms, preferably pentaoxyethyleneglycol. In other embodiments, the hydrocarbyl contains phenyl or pyridyl.

$R_7$, $R_8$, $R_9$, $R'_9$ and/or $R''_9$ may also be hydrocarbyl substituted by one or more functional groups such as halogen, for example Cl, Br, F or I, nitro, oxo, alkoxy (OR), SR, epoxy, epithio, —CONRR', —COR, COOR", COSR, —OSO$_3$R, —SO$_3$R", —SO$_2$R, —NHSO$_2$R, —SO$_2$NRR'—NRR', =N—OR, =N—NRR', —C(=NR)—NRR', —NR—NRR', —(R)N—C(=NR)—NRR', O←NR—, >C=NR, —(CH$_2$)$_n$—NR—COR', —(CH$_2$)$_n$—CO—NRR', —O—(CH$_2$)$_n$—OR, —O—(CH$_2$)$_n$—O—(CH$_2$)$_n$—R, —PRR', —OPO$_3$RR', —PO$_2$HR and —PO$_3$R"R", wherein n is an integer of 1 to 10 and R and R' each independently is H, hydrocarbyl, or heterocyclyl, or R and R' together with the N atom to which they are attached form a 3-7 membered saturated ring, optionally containing one or more heteroatoms selected from the group consisting of O, S or N, and optionally further substituted at the additional N atom, and R" is H, a cation, hydrocarbyl, or heterocyclyl.

In certain embodiments, some of the functional groups above are acidic groups that may convert to negatively charged groups under physiological pH, for example COOH, COSH, SO$_3$H, PO$_3$H$_2$, or the functional groups are negatively charged group such as COO$^-$, COS$^-$, SO$_3^-$, or PO$_3^{2-}$. The negatively charged group and the acidic group may be an end group or a group within the hydrocarbyl chain. In most preferred embodiments, the hydrocarbyl has 2 or 3 carbon atoms and an end group selected from COO$^-$, PO$_3^{2-}$, or, most preferably, SO$_3^-$.

As used herein, "physiological conditions" refers to the conditions in different tissues and cell compartments of the body.

In certain embodiments, $R_7$, $R_8$, $R_9$, $R'_9$ and/or $R''_9$ may by substituted by at least one positively charged group and/or at least one basic group that is converted to a positively charged group under physiological conditions. In a preferred embodiment, the at least one positively charged group may be a cation derived from a N-containing group such as, but not limited to, an ammonium —N$^+$(RR'R"), hydrazinium —(R)N—N$^+$(R'R"), ammoniumoxy O←N$^+$(RR')—, iminium >C=N$^+$(RR'), amidinium —C(=RN)—N$^+$R'R" or guanidinium —(R)N—C(=NR)—N$^+$R'R" group, wherein R, R' and R" are as defined above. It is to be understood that the positively charged N-containing group may be an end group, a group within the hydrocarbyl chain, or part of a saturated ring in which the N is protonated, as defined hereinafter. In addition, the at least one positively charged group may also be a cation derived from a N-containing heteroaromatic radical, as defined hereinafter.

In one preferred embodiment, the hydrocarbyl chain is substituted by an ammonium group of the formula —N$^+$(RR'R"), wherein each of R, R' and R" independently is H, hydrocarbyl, preferably $C_1$-$C_{25}$ alkyl, more preferably $C_1$-$C_{10}$ or $C_1$-$C_6$ alkyl, or heterocyclyl. When one of R, R' or R" is OH, the group is a hydroxyl ammonium group. Preferably, the ammonium group is a quaternary ammonium group wherein R, R' and R" each independently is $C_1$-$C_6$ alkyl such as methyl, ethyl, propyl, butyl, pentyl or hexyl.

In certain embodiments, the ammonium group of the formula —N$^+$(RR'R") is a cyclic group, wherein two of R, R' and R" together with the N atom form a 3-7 membered saturated ring, optionally containing a further heteroatom selected from the group consisting of O, S and N atom, and optionally further substituted at the additional N atom, as defined hereinafter. Examples of such cyclic ammonium groups include aziridinium, pyrrolidinium, piperidinium, piperazinium, morpholinium, thiomorpholinium, azepinium, and the like.

In certain embodiments, the positively charged group is a cation derived from a N-heteroaromatic compound that may be a mono- or polycyclic compound that may further contain O, S or additional N atoms. The ring from which the cation is derived should contain at least one N atom and be aromatic, but the other ring(s), if any, can be partially saturated. Examples of N-heteroaromatic cations include pyrazolium, imidazolium, oxazolium, thiazolium, pyridinium, pyrimidinium, quinolinium, isoquinolinium, 1,2,4-triazinium, 1,3,5-triazinium and purinium.

The cation may also be an onium group not containing N such as, but not limited to, a phosphonium [—P$^+$(RR'R")], arsonium [—As$^+$(RR'R")], oxonium [—O$^+$(RR')], sulfonium [—S$^+$(RR')], selenonium [—Se$^+$(RR')], telluronium [—Te$^+$(RR')], stibonium [—Sb$^+$(RR'R")], or bismuthonium [—Bi$^+$(RR'R")] group, wherein R, R' and R" are as defined above. In preferred embodiments, R, R' and R" are H, $C_1$-$C_6$ alkyl such as methyl, ethyl, propyl, isopropyl, n-butyl, isobutyl, sec-butyl, pentyl or hexyl, an aryl group, preferably, phenyl, or an aralkyl group, such as benzyl and phenethyl.

In certain other embodiments, $R_7$, $R_8$, $R_9$, $R'_9$ and/or $R''_9$ are substituted by at least one basic group that is converted to a positively charged group under physiological conditions. As defined herein, "a basic group that is converted to a positively charged group under physiological conditions" is, at least theoretically, any basic group that will generate under physiological conditions a positively charged group as defined herein, wherein the physiological conditions, as used herein, do not refer solely to the serum, but to different tissues and cell compartments in the body.

In certain embodiments, the basic group is a N-containing group. Examples of such N-containing basic groups include, without being limited to, any amino group that will generate an ammonium group, any imine group that will generate an iminium group, any hydrazine group that will generate a hydrazinium group, any aminooxy group that will generate an ammoniumoxy group, any amidine group that will generate an amidinium group, any guanidine group that will generate a guanidinium group, all as defined herein. Other examples include phosphino and mercapto groups.

Thus, $R_7$, $R_8$, $R_9$, $R'_9$ and/or $R''_9$ may be substituted by at least one basic group such as —NRR', —C(=NR)—NR'R", —NR—NR'R", —(R)N—C(=NR)—NR'R", O←NR—, or >C=NR, wherein R, R' and R" are as defined above but preferably $C_1$-$C_{25}$ alkyl, more preferably $C_1$-$C_{10}$ or $C_1$-$C_6$ alkyl, or heterocyclyl. In preferred embodiments, the basic group is an amino group NRR', an end group or a group within the hydrocarbyl chain, that may be a secondary amino, wherein only one of R and R' is H, or a tertiary amino wherein none of R and R' is H, or it may be a cyclic amino wherein R and R' together with the N atom form a 3-7 membered saturated ring, optionally containing a further heteroatom selected from the group consisting of O, S and N atom, and optionally further substituted at the additional N atom.

The $C_1$-$C_{25}$ hydrocarbyl defined for $R_7$, $R_8$, $R_9$, $R'_9$ and/or $R''_9$ may also be substituted by the residue of a mono-, oligo- or polysaccharide such as glycosyl, or of an amino acid, peptide or protein. In addition, $R_8$, $R_9$, $R'_9$ and $R''_9$ each may independently be is a moiety of an oligosaccharide, or a polysaccharide, preferably a monoaccharide such as glucosamine, and/or the residue of an amino acid, a peptide or a protein. In one preferred embodiment, $R_8$, $R_9$, $R'_9$ or $R''_9$ at any of the positions, but preferably at position $17^3$, is the residue of an amino acid, a peptide or a protein. The amino acid, peptide or protein may be negatively charged if they contain a free terminal carboxyl group and/or a residue of an amino acid containing a non-terminal free carboxylic group, e.g. aspartic or glutamic acid.

In one embodiment, $R_7$, $R_8$, $R_9$, $R'_9$ or $R''_9$ is the residue of an amino acid containing a hydroxy group, such as serine, threonine and tyrosine or a derivative thereof selected from esters such as alkyl, preferably methyl, esters, and N-protected derivatives wherein the N-protecting group is for example tert-butyloxy, carbobenzoxy or trityl, or peptides (oligopeptide or polypeptide) containing such amino acid and/or amino acid derivatives. The hydroxylated amino acid or peptide is linked to the COO⁻ group, preferably at position $17^3$, of the (bacterio)chlorophyll derivative through its hydroxy group. Examples of such amino acid derivatives are serine methyl ester, N-tert-butyloxycarbonyl-serine, N-trityl-serine methyl ester, tyrosine methyl ester, and N-tert-butoxy-tyrosine methyl ester, and an example of a peptide containing said amino acid derivative is N-carbobenzoxy-seryl serine methyl ester, all of which are prepared as described in the EP 0584552 incorporated herein by reference as if fully disclosed herein.

In certain embodiments, $R_7$, $R_8$, $R_9$, $R'_9$ or $R''_9$ is the residue of a cell-specific or tissue-specific ligand selected from peptides and proteins, which are exemplified by, but not limited to, hormone peptides and antibodies, e.g. immunoglobulins. The peptide or protein may be linked directly to the —CO group via an ester, thioester or amide bond, or it may be linked via an ester or amide bond to an end functional group of the $C_1$-$C_{25}$ hydrocarbyl radical selected from OH, COOH and $NH_2$.

In certain embodiments, the (bacterio)chlorophyll derivatives used in accordance with the invention contain COOH, COSH, COO⁻, and/or COS⁻ group derived from $R_1$, $R'_2$ and $R_6$ being OH or SH, O⁻$R_{10}^+$ or S⁻$R_{10}^+$, respectively, i.e., when a carboxylic or thiocarboxylic group or a carboxylate or thiocarboxylate anion is present at the position $13^1$, $15^1$ (m is 0), $15^2$ (m is 1), and/or $17^3$.

In certain embodiments $R_1$, $R'_2$ and/or $R_6$ is a basic group —$NR_9R'_9$ or an ammonium group —$N^+R_9R'_9R''_9$, or $R_5$ is N—$R_9$ or $N^+R_9R'_9$.

In certain embodiments, $R_1$, $R'_2$ and/or $R_6$ is Y—$R_8$ wherein Y is O and $R_8$ is a residue of an amino acid or peptide (oligo or polypeptide) linked through an amide bond via a free —$NH_2$ group.

The cation $R_{10}^+$ may be a monovalent or divalent cation derived from an alkaline or alkaline earth metal such as $K^+$, $Na^+$, $Li^+$, $Ca^+$, more preferably $K^+$; or $R_{10}^+$ is an organic cation such as herein defined for "a cation derived from a N-containing group". Preferably, the organic cation is derived from an amine, e.g., $NH_4^+$.

As defined herein, A⁻ is a physiologically acceptable anion such as chloride, bromide, iodide, perchlorate, sulfate, phosphate or an organic anion such as acetate, benzoate, caprylate, citrate, lactate, malonate, mandelate, mesylate, oxalate, propionate, succinate, tosylate, and the like.

As defined herein, "a 3-7 membered saturated ring" formed by R and R' together with the N atom to which they are attached may be a ring containing only N such as aziridine, pyrrolidine, piperidine, piperazine or azepine, or it may contain a further heteroatom selected from O and S such as morpholine or thiomorpholine. The further N atom in the piperazine ring may be optionally substituted by alkyl, e.g. $C_1$-$C_6$ alkyl, that may be substituted by halogen, OH or amino. The onium groups derived from said saturated rings include aziridinium, pyrrolidinium, piperidinium, piperazinium, morpholinium, thiomorpholinium and azepinium.

In certain embodiments, the (bacterio)chlorophyll derivative used in accordance with the present invention is unmetalated, namely M is 2H. In preferred embodiments, the photosensitizer is metalated and M is Mg, Pd, Pt, Zn, In, Gd, or Yb, more preferably Pd.

In one preferred embodiment, the ophthalmic composition provided by the present invention for treatment of eye diseases and disorders associated with corneal thinning or scleral stretching comprises chlorophyll or bacteriochlorophyll derivative of the formula I wherein: M represents divalent Pd; $R_1$ is —NH—$(CH_2)_n$—$SO_3^-R_{10}^+$, —NH—$(CH_2)_n$—$COO^-R_{10}^+$; or —NH—$(CH_2)_n$—$PO_3^{2-}(R_8^+)_2$; $R_2$ is methoxy; $R_3$ is —C(=O)—$CH_3$; $R_5$ is O; $R_{10}^+$ is a monovalent cation such as $K^+$, $Na^+$, $Li^+$, or $NH_4^+$; and n is an integer from 1 to 10, preferably 2 or 3. Preferably, according to this embodiment, $R_1$ is —NH—$(CH_2)_3$—$SO_3^-$ $K^+$.

In more preferred embodiments, the photosensitizer is a bacteriochlorophyll of the formula I having a sole negatively charged group ($SO_3^-$) at position 17, represented by the compound palladium bacteriopheophorbide a $17^3$-(3-sulfopropyl) amide potassium salt.

In certain embodiments, the ophthalmic composition for treatment of corneal thinning or scleral stretching comprises a derivative of chlorophyll or bacteriochlorophyll of formula II in which $R_6$ or both $R_1$ and $R_6$ are —$NR_9R'_9$. Preferably according to these embodiments, $R_9$ is H and $R'_9$ is a $C_1$-$C_{10}$ alkyl substituted by at least one group selected from a positively charged group, a negatively charged group, an acidic group that is converted to a negatively charged group under physiological conditions, or a basic group that is converted to a positively charged group under physiological conditions. In more particular embodiments $R'_9$ is a $C_1$-$C_6$ alkyl substituted by the acidic $SO_3H$ group or an alkaline salt thereof, or by a basic group —NRR' or —NH—$(CH_2)_{2-6}$—NRR', wherein each of R and R' independently is H, $C_1$-$C_6$ alkyl optionally substituted by $NH_2$, or R and R' together with the N atom form a 5-6 membered saturated ring, optionally containing an O or N atom and optionally further substituted at the additional N atom by $—(CH_2)_{2-6}—NH_2$.

In certain embodiments, the ophthalmic composition of the invention comprises a bacteriochlorophyll derivative of formula II, wherein:

M is 2H, Mg, Pd, or Zn;

$R_1$ is selected from:
(i) $—O^-R_{10}^+$;
(ii) $Y—R_8$ wherein Y is O or S and $R_8$ is the residue of an amino acid, a peptide or a protein;
(iii) $—NH—CH_2—CH(OH)—CH_2OH$;
(iv) $—NH—(CH_2)_n—OH$;
(v) $—NH—CH(OH)—CH_3$;
(vi) $—NH—(CH_2)_n—NR—(CH_2)_n—OH$;
(vii) glycosylamino; or
(viii) $NHR'_9$ which is as defined for $R_6$;

$R'_2$ is $C_1$-$C_6$ alkoxy such as methoxy, ethoxy, propoxy or butoxy, more preferably methoxy;

$R_4$ is $—C(=O)—CH_3$, $—CH=N—(CH_2)_n—SO_3^-R_{10}^+$; $—CH=N—(CH_2)_n—COO^-R_{10}^+$; $—CH=N—(CH_2)_n—PO_3^{2-}(R_{10}^+)_2$; $—CH_2—NH—(CH_2)_n—SO_3^-R_{10}^+$; $—NH—(CH_2)_n—COO^-R_{10}^+$; $—NH—(CH_2)_n—PO_3^{2-}(R_{10}^+)_2$; or $—C(CH_3)=NR_9$, preferably $C(CH_3)=N—(CH_2)_n—NH_2$, or $—C(CH_3)=N—(CH_2)_n—N(R)_3^+A^-$;

$R_6$ is selected from (i) $NHR'_9$, selected from:
(a) $—NH—(CH_2)_n—SO_3^-R_{10}^+$, preferably $—NH—(CH_2)_2—SO_3R_{10}^+$ or $—NH—(CH_2)_3—SO_3R_{10}^+$;
(b) $—NH—(CH_2)_n—COO^-R_{10}^+$;
(c) $—NH—(CH_2)_n—PO_3^{2-}(R_{10}^+)_2$;
(d) $—NH—(CH_2)_n—B$:
(e)

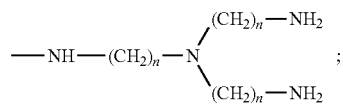

(f)

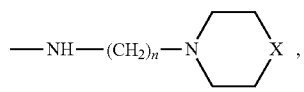

preferably $—NH—(CH_2)_2$-1-morpholino or $—NH—(CH_2)_3$-piperazino;

(g)

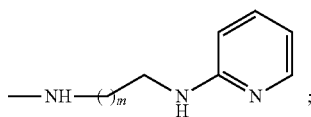

(h) $—NH—(CH_2)_n—N(R")—(CH_2)_n—NRR'$, preferably $—NH—(CH_2)_3—NH—(CH_2)_3—NH_2$;
(j) $—NH—(CH_2)_n—NRR'$, preferably $—NH—CH_2—CH_2—NRR'$;

$R_{10}^+$ is $H^+$, or a monovalent cation such as $K^+$, $Na^+$, $Li^+$, or $NH_4^+$, more preferably $K^+$;

X is O, S or NH;

B is a positively charged group selected from ammonium $—N^+RR'R"$, preferably $—N(CH_3)_3^+A^-$, guanidinium, sulfonium, phosphonium, arsonium; or B is a basic group that is converted to a positively charged group under physiological conditions, selected from amino $—NRR'$, preferably $—NH_2$, guanidino, phosphino, or arsino;

m is 1, n is an integer from 1 to 10, preferably 2 or 3; and $A^-$ is a physiologically acceptable anion;

wherein R, R' and R" each independently is H or $C_1$-$C_6$ alkyl.

In preferred embodiments, the pharmaceutical composition comprises bacteriochlorin or rhodobacteriochlorin derivative of formula II wherein only $R_6$ or both $R_1$ and $R_6$ are selected from $—NH—(CH_2)_2—SO_3R_{10}^+$, $—NH—(CH_2)_3—SO_3R_{10}^+$, $—NH—(CH_2)_3—NH—(CH_2)_3—NH_2$, $—NH—(CH_2)_2$-1-morpholino, or $—NH—(CH_2)_3$-piperazino-$(CH_2)_3—NH_2$, and $R_{10}^+$ is a monovalent cation such as $K^+$, $Na^+$, $Li^+$, $NH_4^+$, preferably $K^+$. In certain more preferred embodiments, $R_1$ and $R_6$ are both $—NH—(CH_2)_2—SO_3R_{10}^+$ or $—NH—(CH_2)_3—SO_3R_{10}^+$.

In other preferred embodiments, chlorin or (rhodo)bacteriochlorin derivatives of the formula II are used in accordance with the invention, having at least one negatively charged group and M is absent or is divalent Pd or Zn ion, preferably Pd. In these embodiments, $R_1$ is selected from $—O^-R_{10}^+$, $—NH—(CH_2)_n—SO_3^-R_{10}^+$, $—NH—(CH_2)_n—COO^-R_{10}^+$ or $—NH—(CH_2)_n—PO_3^{2-}(R_{10}^+)_2$, or $R_1$ is $Y—R_8$ wherein Y is O, S and $R_8$ is the residue of an amino acid, a peptide or a protein; $R'_2$ is $C_1$-$C_6$ alkoxy such as methoxy, ethoxy, propoxy, butoxy, more preferably methoxy; $R_4$ is selected from $—C(=O)—CH_3$, $—CH=N—(CH_2)_n—SO_3^-R_{10}^+$, $—CH=N—(CH_2)_n—COO^-R_{10}^+$, $—CH=N—(CH_2)_n—PO_3^{2-}(R_{10}^+)_2$, or $—CH_2—NH—(CH_2)_n—SO_3^-R_{10}^+$; $R_6$ is $—NH—(CH_2)_n—SO_3^-R_{10}^+$, $—NH—(CH_2)_n—COO^-R_{10}^+$, or $—NH—(CH_2)_n—PO_3^{2-}(R_{10}^+)_2$; $R_{10}^+$ is a monovalent cation such as $K^+$, $Na^+$, $Li^+$, or $NH_4^+$, more preferably $K^+$; m is 1, and n is an integer from 1 to 10, preferably 2 or 3.

In a more preferred embodiment, the negatively charged photosensitizer used in accordance with the invention is a bacteriochlorin derivative of the formula II wherein: M is Pd; $R_1$ is $—O^-R_{10}^+$, $NH—(CH_2)_n—SO_3^-R_{10}^+$, or $Y—R_8$ wherein Y is O or S and $R_8$ is the residue of a protein, preferably immunoglobulin; $R'_2$ is $C_1$-$C_6$ alkoxy such as methoxy, ethoxy, propoxy, butoxy, more preferably methoxy; $R_4$ is $—C(=O)—CH_3$, $—CH=N—(CH_2)_n—SO_3^-R_{10}^+$ or $—CH_2—NH—(CH_2)_n—SO_3^-R_{10}^+$; $R_6$ is $—NH—(CH_2)_n—SO_3^-R_{10}^+$, $NH—(CH_2)_n—COO^-R_{10}^+$, or $NH—(CH_2)_n—PO_3^{2-}(R_8^+)_2$; $R_{10}^+$ is a monovalent cation such as $K^+$, $Na^+$, $Li^+$ or $NH_4^+$, more preferably $K^+$; m is 1, and n is 2 or 3, more preferably 2.

Examples of rhodobacteriochlorin derivatives of formula II having one, two or three negatively charged groups at positions 3, 13 and/or 17 are:

Palladium $3^1$-oxo-15-methoxycarbonylmethyl-rhodobacteriochlorin $13^1$-(2-sulfoethyl)amide dipotassium salt (herein designated WST11);

Palladium $3^1$-oxo-15-methoxycarbonylmethyl-rhodobacteriochlorin $13^1$-(-sulfopropyl)amide dipotassium salt (compound 1);

Palladium $3^1$-oxo-15-methoxycarbonylmethyl-rhodobacteriochlorin $13^1,17^3$-di-(2-sulfoethyl)amide dipotassium salt (compound 2);

Palladium $3^1$-oxo-15-methoxycarbonylmethyl-rhodobacteriochlorin $13^1,17^3$-di-(3-sulfopropyl)amide dipotassium salt (compound 3);

$3^1$-oxo-15-methoxycarbonylmethyl-rhodobacteriochlorin $13^1$-(2-sulfoethyl) amide dipotassium salt (compound 4);
$3^1$-oxo-15-methoxycarbonylmethyl-rhodobacteriochlorin $13^1$-(-sulfopropyl)amide dipotassium salt (compound 5);
$3^1$-oxo-15-methoxycarbonylmethyl-rhodobacteriochlorin $13^1,17^3$-di-(2-sulfoethyl)amide dipotassium salt (compound 6);
$3^1$-oxo-15-methoxycarbonylmethyl-rhodobacteriochlorin $13^1,17^3$-di-(3-sulfopropyl)amide dipotassium salt (compound 7);
Zinc $3^1$-oxo-15-methoxycarbonylmethyl-rhodobacteriochlorin $13^1$-(2-sulfoethyl) amide dipotassium salt;
Palladium $3^1$-oxo-15-methoxycarbonylmethyl-rhodobacteriochlorin $13^1$-(2-sulfoethyl)amide, $17^3$-(N-immunoglobulin G)amide potassium salt;
Palladium $3^1$-oxo-15-methoxycarbonylmethyl-rhodobacteriochlorin $13^1$-(2-carboxyethyl)amide dipotassium salt;
Palladium $3^1$-oxo-15-methoxycarbonylmethyl-rhodobacteriochlorin $13^1$-(3-phosphopropyl)amide tripotassium salt
Palladium $3^1$-(3-sulfopropylimino)-15-methoxycarbonylmethyl-rhodobacteriochlorin $13^1,17^3$-di(3-sulfopropyl)amide tripotassium salt;
Palladium $3^1$-(3-sulfopropylamino)-15-methoxycarbonylmethyl-rhodobacteriochlorin $13^1,17^3$-di(3-sulfopropyl)amide tripotassium salt.
Palladium $3^1$-oxo-15-methoxycarbonylmethyl-rhodobacteriochlorin $13^1,17^3$-di(3-propionyl)amide salt;
Palladium $3^1$-oxo-15-methoxycarbonylmethyl-rhodobacteriochlorin $13^1,17^3$-di[2-(3-propionylamino)-sulfoethyl]amide dipotassium salt;
Palladium $3^1$-oxo-15-methoxycarbonylmethyl-rhodobacteriochlorin $13^1,17^3$-di[2-(3-propionylamino)-phosphoethyl]amide dipotassium salt;
Palladium $3^1$-oxo-15-methoxycarbonylmethyl-rhodobacteriochlorin $13^1,17^3$-di(3-thiopropionyl)amide dipotassium salt $3^1$-hydroxy-$3^1$-deoxo-bacteriopheophorbide a;
$3^1$-(Pyridin-4-ylmethoxy)-$3^1$-deoxo-bacteriopheophorbide a;
Bacteriopheophorbide a $17^3$-[(2,6-dichloro-4-methoxyphenyl)(2,4-dichlorophenyl)]methyl ester;
$3^1$-Hydroxy-$3^1$-deoxo-bacteriopheophorbide a $17^3$-[(2,6-dichloro-4-methoxyphenyl)(2,4-dichlorophenyl)]methyl ester;
$3^1$-trifluoroacetoxy-$3^1$-deoxo-bacteriopheophorbide a $17^3$-[(2,6-dichloro-4-methoxyphenyl)(2,4-dichlorophenyl)]methyl ester;
$3^1$-Bromo-$3^1$-deoxo-bacteriopheophorbide a;
3-Vinyl-3-deacetyl-bacteriopheophorbide;
$3^1$-(2-Hydroxyethoxy)-$3^1$-deoxo-bacteriopheophorbide a;
$3^1$-(2,2,2-Trifluoroethoxy)-$3^1$-deoxo-bacteriopheophorbide a;
$3^1$-(2-Mercaptoethylsulfanyl)-$3^1$-deoxo-bacteriopheophorbide a;
$3^1$-(2-Hydroxyethylamino)-$3^1$-deoxo-bacteriopheophorbide a;
Cobalt(III) $3^1$-oxo-15-methoxycarbonylmethyl-rhodobacteriochlorin $13^1$-(2-sulfoethyl)amide dipotassium salt;
Iron(III) $3^1$-oxo-15-methoxycarbonylmethyl-rhodobacteriochlorin $13^1$-(2-sulfoethyl)amide dipotassium salt; and
Nickel(II) Bacteriopheophorbide a;
Platinum(II) Bacteriopheophorbide a.

In a preferred embodiment, the compounds used in accordance with the present invention are pharmaceutically acceptable salts of taurinated or homotaurinated bacteriochlorin derivatives with a monovalent or divalent alkaline or alkaline earth metal cation, or with $NH_4^+$ selected from:

Palladium $3^1$-oxo-15-methoxycarbonylmethyl-rhodobacteriochlorin $13^1$-(2-sulfoethyl)amide;
Palladium $3^1$-oxo-15-methoxycarbonylmethyl-rhodobacteriochlorin $13^1$-(3-sulfopropyl)amide;
Palladium $3^1$-oxo-15-methoxycarbonylmethyl-rhodobacteriochlorin $13^1,17^3$-di-(2-sulfoethyl)amide;
Palladium $3^1$-oxo-15-methoxycarbonylmethyl-rhodobacteriochlorin $13^1,17^3$-di-(3-sulfopropyl)amide;
$3^1$-oxo-15-methoxycarbonylmethyl-rhodobacteriochlorin $13^1$-(2-sulfoethyl)amide;
$3^1$-oxo-15-methoxycarbonylmethyl-rhodobacteriochlorin $13^1$-(-sulfopropyl)amide;
$3^1$-oxo-15-methoxycarbonylmethyl-rhodobacteriochlorin $13^1,17^3$-di-(2-sulfoethyl)amide; and
$3^1$-oxo-15-methoxycarbonylmethyl-rhodobacteriochlorin $13^1,17^3$-di-(3-sulfopropyl)amide.

Most preferred compounds are WST11 and compounds 1-7.

The bacteriochlorophyll derivatives used in the invention can be prepared by the methods described in U.S. Pat. No. 7,947,672 or in WO 2005/120573. For the preparation of compounds wherein $R_8$ is the residue of an amino acid, peptide or protein, the methods described in EP 0584552 may be applied. For the preparation of negatively charged bacteriochlorin derivatives wherein $R_8$ is a residue of amino acid, the method disclosed in EP 0584552 may be combined with the method described in Scheme 1 of U.S. Pat. No. 7,947,672.

Method for the preparation of negatively-charged compounds of formula II are disclosed in U.S. Pat. No. 7,947,672 mentioned above. For example, preparation of a bacteriochlorin compound wherein $R_1$ is $—O^-$ $R_{10}^+$; $R'_2$ is $—OCH_3$; $R_3$ is acetyl; $R_6$ is a group $—NH—(CH_2)_n—SO_3^-$ $R_{10}^+$, $—NH—(CH_2)_n—COO^-R_{10}^+$, or $—NH—(CH_2)_n—PO_3^{2-}(R_{10}^+)_2$; $R_{10}^+$ is a monovalent cation; m is 1 and n is 1 to 10, comprises: (i) reacting the corresponding metalated bacteriopheophorbide (M-bacteriopheophorbide) of formula I herein wherein $R_1$ is OH with an aminosulfonic acid of the formula $H_2N—(CH_2)_n—SO_3H$ (e.g., taurine $H_2N—(CH_2)_2—SO_3H$ or homotaurine $H_2N—(CH_2)_3—SO_3H$) aminocarboxylic acid of the formula $H_2N—(CH_2)_n—COOH$ or aminophosphonic acid of the formula $H_2N—(CH_2)_n—PO_3H_2$, respectively, in a $R_{10}^+$-buffer; and (ii) isolating the desired compound of formula II.

Bacteriochlorins of formula II having the same negatively charged groups mentioned above at positions 13 and 17 may be prepared by reacting the corresponding M-bacteriopheophorbide with an excess of the reagent aminosulfonic, aminocarboxylic or aminophosphonic acid as described above, and isolation of the desired 13,17-disubstituted derivative, or a different route can be followed as disclosed in U.S. Pat. No. 7,947,672. For example, a bacteriochlorin of the formula II wherein $R_1$ and $R_6$ are each a group $—NH—(CH_2)_n—SO_3^-R_{10}^+$; $R_2$ is $—OCH_3$; $R_3$ is acetyl; $R_{10}^+$ is a monovalent cation; m is 1 and n is 1 to 10, are prepared by: (i) coupling the corresponding M-bacteriopheophorbide of formula I wherein $R_1$ is OH with N-hydroxy-sulfosuccinimide (sulfo NHS) in the presence of 1-ethyl-3-(3-dimethylaminopropyl)-carbodiimide (EDC); (ii) reacting the resulting M-bacteriopheophorbide-$17^3$-N-hydroxysulfosuccinimide ester with an excess of an aminosulfonic acid of the formula $H_2N—(CH_2)_n—SO_3H$ in a $R_8^+$-buffer, thus obtaining a compound of formula I having a sole negatively charged group at position 17; (iii) reacting this product with an excess of $H_2N—(CH_2)_n—SO_3H$ in a $R_8^+$-buffer; and isolating the desired bacteriochlorin of formula II. When the aminosulfonic acid is replaced by aminocarboxylic or aminophosphonic acid, the corresponding carboxylate and phosphonate derivatives are obtained.

In other embodiments, the photosensitizer used in accordance with the invention is a purpurin-18 or bacteriopurpurin-18 derivative of formula III, wherein X is —$NR_7$, $R_7$ is —NRR', R is H and R' is $C_1$-$C_6$ alkyl substituted by $SO_3$— or an alkaline salt thereof, preferably the photosensitizer is a bacteriopurpurin-18, wherein X is —$NR_7$ and $R_7$ is —NH—$(CH_2)_3$—$SO_3^-R_{10}^+$, wherein $R^+_{10}$ is a metal cation, an ammonium group or an organic cation, preferably $K^+$.

In certain embodiments, the pharmaceutical compositions used in accordance with the invention comprise a chlorophyll or bacteriochlorophyll derivative of the formula I, II or III containing at least one positively charged group and/or at least one basic group that is converted to a positively charged group at the physiological pH, wherein the positively charged groups and basic group are as defined above.

In certain embodiments, the photosensitizer is a chlorophyll or (rhodo)bacteriochlorophyll derivative of formula II and $R_6$ is —$NR_9R'_9$, $R_9$ is H and $R'_9$ is $HOCH_2$—CH(OH)—$CH_2$—.

In certain preferred embodiments, the pharmaceutical composition used according to the invention comprises a bacteriochlorin or rhodobacteriochlorin derivative of the formula II wherein $R_1$ is selected from OH, —$NR_9R'_9$, or —$NR_9$—$CH_2$—CH(OH)—$CH_2OH$; and $R_6$ is selected from —$NR_9R'_9$ or —$NR_9$—$CH_2$—CH(OH)—$CH_2OH$, wherein $R_9$ is H or $C_1$-$C_6$ alkyl; and $R'_9$ is $C_1$-$C_{25}$ hydrocarbyl substituted by at least one positively charged group and/or at least one basic group that is converted to a positively charged group under physiological conditions. In preferred embodiments, $R'_9$ is $C_1$-$C_{25}$ alkyl, preferably $C_1$-$C_{10}$, more preferably $C_1$-$C_6$ alkyl, substituted by at least one positively charged group, more preferably —$N^+RR'R''$, or by at least one basic group, preferably —NRR', and optionally interrupted by a —N(R'')-group, wherein R and R' each independently is H, $C_1$-$C_6$ alkyl optionally substituted by NR''R', or heterocyclyl such as pyridyl, or R and R' together with the N atom form a 6-membered ring further containing an O, S or N atom, and R'' is H or $C_1$-$C_6$ alkyl.

Particular compounds used in accordance with these preferred embodiments are positively charged bacteriochlorophyll derivatives wherein M is absent or is Pd; $R'_2$ is —$OR_8$ wherein $R_8$ is $C_1$-$C_6$ alkyl; $R_4$ is —$COCH_3$; and wherein:

(a) $R_1$ is OH and $R_6$ is —$NHR'_9$;
(b) $R_1$ and $R_6$ are both the same —$NHR'_9$ group;
(c) $R_1$ is —NH—$CH_2$—CH(OH)—$CH_2OH$ and $R_6$ is a —$NHR'_9$ group;
(d) $R_1$ is a $NHR'_9$ group and $R_6$ is —NH—$CH_2$—CH(OH)—$CH_2OH$; and
(e) $R_6$ is —NH—$CH_2$—$CH_2$—NRR'; and $R_1$ is selected from the group consisting of
—NH—$(CH_2)_n$—OH;
—NH—CH(OH)—$CH_3$;
—NH—$(CH_2)_n$—NR—$(CH_2)_n$—OH; or
—glycosylamino.

The $NHR'_9$ group is selected from:
(i) —NH—$(CH_2)_n$—NRR' or —NH—$(CH_2)_n$—$N^+RR'R''$;
(ii) —NH—$(CH_2)_n$—N(R'')—$(CH_2)_n$—NRR';
(iii)

$$-NH-(CH_2)_n-N\begin{matrix}(CH_2)_n-NH_2\\(CH_2)_n-NH_2\end{matrix};$$

(iv)

$$-NH-(CH_2)_n-N\underset{\phantom{X}}{\bigcirc}X;$$

and (v)

$$-NH-()_m-\underset{H}{N}-\underset{N}{\bigcirc},$$

wherein
X is O, S or NR;
R, R' and R'' are as defined above, but preferably each independently is H or $C_1$-$C_6$ alkyl, more preferably methyl or ethyl;
n is an integer from 1 to 10, preferably 2 to 6, more preferably 2 or 3; and
m is an integer from 1 to 6, preferably 1 to 3.

Particular examples of such positively charged compounds or compounds that become positively charged under physiological pH are compounds include the herein designated compounds 4'-7',8-12 and 24-75:

Palladium $3^1$-oxo-15-methoxycarbonylmethyl-rhodobacteriochlorin-$13^1$-(2-$N^3$-trimethylammoniumethyl)amide chloride salt (compound 12);

Palladium $3^1$-oxo-15-methoxycarbonylmethyl-rhodobacteriochlorin-$13^1$-(2-$N^3$-(trimethylammoniumethyl)amide acetate salt (compound 24);

Palladium $3^1$-oxo-15-methoxycarbonylmethyl-rhodobacteriochlorin-$13^1$-(2-$N^2$-dimethylaminoethyl)amide (compound 25);

Palladium $3^1$-oxo-15-methoxycarbonylmethyl-rhodobacteriochlorin-$13^1$-(3-$N^2$-dimethylaminopropyl)amide (compound 26);

Palladium $3^1$-oxo-15-methoxycarbonylmethyl-rhodobacteriochlorin-$13^1$-(2-[(2-aminoethyl)amino]ethyl)amide (compound 27);

Palladium $3^1$-oxo-15-methoxycarbonylmethyl-rhodobacteriochlorin-$13^1$-([2-bis(2-aminoethyl)amino]ethyl)amide (compound 28);

Palladium $3^1$-oxo-15-methoxycarbonylmethyl-rhodobacteriochlorin-$13^1$-(2-morpholino-N-ethyl)amide (compound 29);

Palladium $3^1$-oxo-15-methoxycarbonylmethyl-rhodobacteriochlorin-$13^1$-(2-piperazino-N-ethyl)amide (compound 30);

Palladium $3^1$-oxo-15-methoxycarbonylmethyl-rhodobacteriochlorin-$13^1$-(2-[(2-$N^2$-diethylaminoethyl)amino]ethyl)amide (compound 31);

Palladium $3^1$-oxo-15-methoxycarbonylmethyl-rhodobacteriochlorin-$13^1$-(3-[(3-aminopropyl)amino]propyl)amide (compound 32);

$3^1$-oxo-15-methoxycarbonylmethyl-rhodobacteriochlorin-$13^1$,$17^3$-di(2-aminoethyl)amide (compound 4');

$3^1$-oxo-15-methoxycarbonylmethyl-rhodobacteriochlorin-$13^1$,$17^3$-di(2-$N^3$-trimethylammoniumethyl)amide dicitrate salt (compound 5');

$3^1$-oxo-15-methoxycarbonylmethyl-rhodobacteriochlorin-$13^1$,$17^3$-di(3-aminopropyl)amide (compound 6');

3¹-oxo-15-methoxycarbonylmethyl-rhodobacteriochlorin-13¹,17³-di(3-N³-trimethylammoniumpropyl)amide dicitrate salt (compound 7');

3¹-oxo-15-methoxycarbonylmethyl-rhodobacteriochlorin-13¹,17³-di(6-aminohexyl)amide (compound 8);

3¹-oxo-15-methoxycarbonylmethyl-rhodobacteriochlorin-13¹,17³-di(6-N³-trimethylammoniumhexyl)amide dicitrate salt (compound 9);

Palladium 3¹-oxo-15-methoxycarbonylmethyl-rhodobacteriochlorin 13¹,17³-di(2-aminoethyl)amide (compound 10);

Palladium 3¹-oxo-15-methoxycarbonylmethyl-rhodobacteriochlorin 13¹,17³-di(2-N³-trimethylammoniumethyl)amide diphosphate salt (compound 11);

Palladium 3¹-oxo-15-methoxycarbonylmethyl-rhodobacteriochlorin-13¹,17³-di(2-N³-trimethylammoniumethyl)amide diacetate salt (compound 33);

Palladium 3¹-oxo-15-methoxycarbonylmethyl-rhodobacteriochlorin-13¹,17³-di(3-aminopropyl)amide (compound 34);

Palladium 3¹-oxo-15-methoxycarbonylmethyl-rhodobacteriochlorin-13¹,17³-di(4-aminobutyl)amide (compound 35);

Palladium 3¹-oxo-15-methoxycarbonylmethyl-rhodobacteriochlorin-13¹,17³-di(2-N²-dimethylaminoethyl)amide (compound 36);

Palladium 3¹-oxo-15-methoxycarbonylmethyl-rhodobacteriochlorin-13¹,17³-di(3-N²-dimethylaminopropyl)amide (compound 37);

Palladium 3¹-oxo-15-methoxycarbonylmethyl-rhodobacteriochlorin-13¹,17³-di-(2-[(2-aminoethyl)amino]ethyl)amide (compound 38);

Palladium 3¹-oxo-15-methoxycarbonylmethyl-rhodobacteriochlorin-13¹,17³-di-(2-[(2-N²-diethylaminoethyl)amino]ethyl) amide (compound 39);

Palladium 3¹-oxo-15-methoxycarbonylmethyl-rhodobacteriochlorin-13¹,17³-di(2-morpholino-N-ethyl)amide (compound 40);

Palladium 3¹-oxo-15-methoxycarbonylmethyl-rhodobacteriochlorin-13¹,17³-di(2-piperazino-N-ethyl)amide (compound 41);

Palladium 3¹-oxo-15-methoxycarbonylmethyl-rhodobacteriochlorin-13¹,17³-di-(3-[(3-aminopropyl)amino]propyl) amide (compound 42);

Palladium 3¹-oxo-15-methoxycarbonylmethyl-rhodobacteriochlorin-13¹,17³-di([2-bis(2-aminoethyl)amino]ethyl) amide (compound 43);

Palladium 3¹-oxo-15-methoxycarbonylmethyl-rhodobacteriochlorin-13¹,17³-di(2-N-(2'-pyridyl)aminoethyl)amide (compound 44);

Palladium 3¹-oxo-15-methoxycarbonylmethyl-rhodobacteriochlorin-13¹,17³-di(2-N²-diethylaminoethyl)amide (compound 45);

Palladium 3¹-oxo-15-methoxycarbonylmethyl-rhodobacteriochlorin-13¹-(2-aminoethyl)amide-17³-(2,3-dihydroxypropyl) amide (compound 48);

Palladium 3¹-oxo-15-methoxycarbonylmethyl-rhodobacteriochlorin-13¹-(2-N²-dimethylaminoethyl)amide-17³-(2,3-dihydroxypropyl)amide (compound 50);

Palladium 3¹-oxo-15-methoxycarbonylmethyl-rhodobacteriochlorin-13¹-(2-[(2-aminoethyl)amino]ethyl)amide-17³-(2,3-dihydroxypropyl)amide (compound 55);

Palladium 3¹-oxo-15-methoxycarbonylmethyl-rhodobacteriochlorin-13¹-(2-N-(2'-pyridyl)aminoethyl)amide-17³-(2,3-dihydroxypropyl)amide (compound 57);

Palladium 3¹-oxo-15-methoxycarbonylmethyl-rhodobacteriochlorin-13¹-([2-bis(2-aminoethyl)amine]ethyl)amide-17³-(2,3-dihydroxypropyl)amide (compound 59);

Palladium 3¹-oxo-15-methoxycarbonylmethyl-rhodobacteriochlorin-13¹-(3-aminopropyl)amide-17³-(2,3-dihydroxypropyl)amide (compound 60);

Palladium 3¹-oxo-15-methoxycarbonylmethyl-rhodobacteriochlorin-13¹-(4-aminobutyl)amide-17³-(2,3-dihydroxypropyl) amide (compound 61);

Palladium 3¹-oxo-15-methoxycarbonylmethyl-rhodobacteriochlorin-13¹-(2-N²-diethylaminoethyl)amide-17³-(2,3-dihydroxy propyl)amide (compound 62);

Palladium 3¹-oxo-15-methoxycarbonylmethyl-rhodobacteriochlorin-13¹-(2-N-ethylaminoethyl)amide-17³-(2,3-dihydroxy propyl)amide (compound 63);

Palladium 3¹-oxo-15-methoxycarbonylmethyl-rhodobacteriochlorin-13¹-(3-N-methylaminopropyl)amide-17³-(2,3-dihydroxypropyl)amide (compound 64);

Palladium 3¹-oxo-15-methoxycarbonylmethyl-rhodobacteriochlorin-13¹-(3-N-(2'-pyridyl)aminopropyl)amide-17³-(2,3-dihydroxypropyl)amide (compound 71);

Palladium 3¹-oxo-15-methoxycarbonylmethyl-rhodobacteriochlorin-13¹-(4-N-(2'-pyridyl)aminobutyl)amide-17³-(2,3-dihydroxypropyl)amide (compound 72);

Palladium 3¹-oxo-15-methoxycarbonylmethyl-rhodobacteriochlorin-13¹-(2,3-dihydroxypropyl)amide-17³-(2-trimethylammoniumethyl)amide (compound 46);

Palladium 3¹-oxo-15-methoxycarbonylmethyl-rhodobacteriochlorin-13¹-(2,3-dihydroxypropyl)amide-17³-(2-aminoethyl) amide (compound 47);

Palladium 3¹-oxo-15-methoxycarbonylmethyl-rhodobacteriochlorin-13¹-(2,3-dihydroxypropyl)amide-17³-(2-N²-dimethyl aminoethyl)amide (compound 49);

Palladium 3¹-oxo-15-methoxycarbonylmethyl-rhodobacteriochlorin-13¹-(2,3-dihydroxypropyl)amide-17³-(2-[(2-aminoethyl)amino]ethyl)amide (compound 51);

Palladium 3¹-oxo-15-methoxycarbonylmethyl-rhodobacteriochlorin-13¹-(2,3-dihydroxypropyl)amide-17³-(2-[(2-N²-diethyl aminoethyl)amino]ethyl)amide (compound 52);

Palladium 3¹-oxo-15-methoxycarbonylmethyl-rhodobacteriochlorin-13¹-(2,3-dihydroxypropyl)amide-17³-(2-morpholino-N-ethyl)amide (compound 53);

Palladium 3¹-oxo-15-methoxycarbonylmethyl-rhodobacteriochlorin-13¹-(2,3-dihydroxypropyl)amide-17³-(2-piperazino-N-ethyl)amide (compound 54);

Palladium 3¹-oxo-15-methoxycarbonylmethyl-rhodobacteriochlorin-13¹-(2,3-dihydroxypropyl)amide-17³-(2-N-(2'-pyridyl)aminoethyl)amide (compound 56);

Palladium 3¹-oxo-15-methoxycarbonylmethyl-rhodobacteriochlorin-13¹-(2,3-dihydroxypropyl)amide-17³-([2-bis(2-aminoethyl)amino]ethyl)amide (compound 58);

Palladium 3¹-oxo-15-methoxycarbonylmethyl-rhodobacteriochlorin-13¹-(2,3-dihydroxypropyl)amide-17³-(3-N-(2'-pyridyl)aminopropyl)amide (compound 73);

Palladium 3¹-oxo-15-methoxycarbonylmethyl-rhodobacteriochlorin-13¹-(2,3-dihydroxypropyl)amide-17³-(4-N-(2'-pyridyl)aminobutyl)amide (compound 74);

Palladium 3¹-oxo-15-methoxycarbonylmethyl-rhodobacteriochlorin-13¹-(2-N²-dimethylaminoethyl)amide-17³-(2-hydroxy ethyl)amide (compound 65);

Palladium 3¹-oxo-15-methoxycarbonylmethyl-rhodobacteriochlorin-13¹-(2-N²-dimethylaminoethyl)amide-17³-(3-hydroxy propyl)amide (compound 66);

Palladium 3¹-oxo-15-methoxycarbonylmethyl-rhodobacteriochlorin-13¹-(2-N²-dimethylaminoethyl)amide-17³-(2-hydroxy propyl)amide (compound 67);

Palladium $3^1$-oxo-15-methoxycarbonylmethyl-rhodobacteriochlorin-$13^1$-(2-$N^2$-dimethylaminoethyl)amide-$17^3$-((R)-2-hydroxypropyl)amide (compound 68);

Palladium $3^1$-oxo-15-methoxycarbonylmethyl-rhodobacteriochlorin-$13^1$-(2-$N^2$-dimethylaminoethyl)amide-$17^3$-((S)-2-hydroxypropyl)amide (compound 69);

Palladium $3^1$-oxo-15-methoxycarbonylmethyl-Rhodobacteriochlorin-$13^1$-(2-$N^2$-dimethylaminoethyl)amide-$17^3$-(2-(2-hydroxyethyl amino)ethyl) amide (compound 70); and Palladium $3^1$-oxo-15-methoxycarbonylmethyl-rhodobacteriochlorin-$13^1$-(2-$N^2$-dimethylaminoethyl)amide-$17^3$-(glycosyl) amide (compound 75).

The compounds listed above can be prepared e.g., as described in detail in WO 2005/120573 mentioned above.

Other positively charged bacteriochlorin derivatives and basic bacteriochlorin derivatives that become positively charged under physiological pH are compounds of the formula II, wherein M is Pd, $R'_2$ is —$OR_8$ wherein $R_8$ is $C_1$-$C_6$ alkyl, preferably methyl, $R_4$ is —$COCH_3$, and $R_1$ and/or $R_6$ are —$NR_9R'_9$, wherein $R_9$ is H and $R'_9$ is $C_1$-$C_{25}$ hydrocarbyl, preferably $C_1$-$C_{25}$ alkyl, more preferably $C_1$-$C_{10}$ alkyl, substituted by: (i) a guanidino or guanidinium group; (ii) a sulfonium group; (iii) a phosphino or phosphonium group; (iv) an arsino or arsonium group.

In a more preferred embodiment, $R_1$ and $R_6$ are both the same group selected from: (i) —NH—$(CH_2)_n$—C(=NH)—$NH_2$ or —NH—$(CH_2)_n$—C(=NH)—$N^+(R)_3A^-$, more preferably, —NH—$(CH_2)_n$—C(=NH)—$N(CH_3)_3^+A^-$;

(ii) —NH—$(CH_2)_n$—$S^+(R)_2$ $A^-$, more preferably, —NH—$(CH_2)_n$—$S(CH_3)_2^+A^-$;

(iii) —NH—$(CH_2)_n$—$P(R)_2$, more preferably, —NH—$(CH_2)_n$—$P(CH_3)_2$ or NH—$(CH_2)_n$—$P^+(R)_3$ $A^-$, more preferably, —NH—$(CH_2)_n$—$P^+(CH_3)_3$ $A^-$; or (iv) —NH—$(CH_2)_n$—$As(R)_2$, more preferably, —NH—$(CH_2)_n$—$As(CH_3)_2$ or NH—$(CH_2)_n$—$As^+(R)_3$ $A^-$, more preferably, —NH—$(CH_2)_n$—$As^+(CH_3)_3$ $A^-$, wherein n is an integer from 1 to 10, preferably 2, 3 or 6.

Examples of such compounds are the compounds herein designated compounds 14, 14a, 15-19:

Palladium $3^1$-oxo-15-methoxycarbonylmethyl-rhodobacteriochlorin $13^1$,$17^3$-di(2-guanidinoethyl)amide (compound 14);

Palladium $3^1$-oxo-15-methoxycarbonylmethyl-rhodobacteriochlorin $13^1$,$17^3$-di(2-trimethylguanidiniumethyl)amide (compound 14a);

Palladium $3^1$-oxo-15-methoxycarbonylmethyl-rhodobacteriochlorin-$13^1$-(2-$S^2$-dimethylsulfoniumethyl)amide citrate salt (compound 15);

$3^1$-oxo-15-methoxycarbomylmethyl-rhodobacteriochlorin-$13^1$,$17^3$-di(2-$P^3$-trimethylphosphoniumethyl)amide dicitrate salt (compound 17);

$3^1$-Oxo-15-methoxycarbonylmethyl-rhodobacteriochlorin-$13^1$,$17^3$-di(2-dimethylphosphinoethyl)amide (compound 18); and $3^1$-Oxo-15-methoxycarbonylmethyl-rhodobacteriochlorin-$13^1$,$17^3$-di(2-$As^3$-trimethylarsoniumethyl)amide dicitrate salt (compound 19).

The above compounds may be prepared as taught in WO 2005/120573.

In still further preferred embodiments, the Bchl derivative used in accordance with the invention is a bacteriochlorin derivative of the formula II, wherein M is 2H or Pd, $R'_2$ is —$OR_8$ wherein $R_8$ is $C_1$-$C_6$ alkyl, preferably methyl, $R_4$ is —$C(CH_3)$=$NR_9$, and/or $R_6$ are —$NR'_9R''_9$, wherein $R'_9$ is H and $R_9$ and $R''_9$ are $C_1$-$C_{25}$ hydrocarbyl, preferably $C_1$-$C_{25}$ alkyl, more preferably $C_1$-$C_{10}$ alkyl, substituted by at least one amino end group or a positively charged group, more preferably an ammonium end group of the formula —$N^+(RR'R'')A^-$, wherein R, R' and R'' are preferably the same $C_1$-$C_6$ alkyl, preferably methyl, and $A^-$ is an anion. In a more preferred embodiment of the invention, $R_4$ is a group of the formula —$C(CH_3)$=N—$(CH_2)_n$—$NH_2$ or —$C(CH_3)$=N—$(CH_2)_n$—$N(R)_3^+A^-$, most preferably —$C(CH_3)$=N—$(CH_2)_n$—$N(CH_3)_3^+A^-$, and $R_1$ and $R_6$ are a group of the formula —NH—$(CH_2)_n$—$NH_2$ or NH—$(CH_2)_n$—$N(R)_3^+A^-$, more preferably, —NH—$(CH_2)_n$—$N(CH_3)_3^+A^-$, wherein n is an integer from 1 to 10, but preferably 2, 3 or 6. Examples of such compounds are the herein designated compounds 20-23:

$3^1$-(aminoethylimino)-15-methoxycarbonylmethyl-rhodobacteriochlorin-$13^1$,$17^3$-di(2-aminoethyl)amide (compound 20);

Palladium $3^1$-(aminoethylimino)-15-methoxycarbonylmethyl-rhodobacteriochlorin $13^1$,$17^3$-di(2-aminoethyl)amide (compound 21);

$3^1$-(trimethylammoniumethylimino)-15-methoxycarbonylmethyl-rhodobacteriochlorin $13^1$,$17^3$-di(2-trimethylammoniumethyl)amide (compound 22); and Palladium $3^1$-(trimethylammoniumethylimino)-15-methoxycarbonylmethyl-rhodobacteriochlorin $13^1$,$17^3$-di(2-trimethylammoniumethyl)amide (compound 23).

The above compounds may be prepared as described in WO 2005/120573.

In certain embodiments, the positively charged photosensitizer used in accordance with the invention is a Bchl derivative of the formula I wherein M is Pd, $R_2$ is —$COOCH_3$, $R_3$ is H, $R_4$ is —$COCH_3$, $R_5$ is =O, and $R_1$ is —$OR_8$, wherein $R_8$ is a residue of an amino acid containing an hydroxy group, preferably serine, or a derivative thereof, preferably an alkyl, more preferably methyl, ester, or a peptide containing said amino acid or derivative thereof, in which amino acid residue the free amino group may be quaternized as a trimethylammonium group. An example of such derivative of formula I is the herein designated compound 13: O—[Pd-Bpheid]-[$N^3$-trimethylammonium-2-methyl]-Serine methyl ester iodide salt.

In accordance with the present invention, pharmaceutically acceptable salts of the (bacterio)chlorophyll compounds of formula I-III are used for PDT treatment of the eye, both salts formed by any carboxy groups present in the molecule, and a base as well as acid addition salts.

Pharmaceutically acceptable salts are formed with metals or amines cations, such as cations of alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," (1977) J. of Pharmaceutical Science, 66:1-19).

Acid addition salts of basic photosensitizers include salts derived from inorganic acids such as hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate or galacturonate (see, for example, Berge S. M., et al., "Pharmaceutical Salts," (1977) J. of Pharmaceutical Science, 66:1-19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The base addition salts of acidic photosensitizers used in accordance with the invention are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The negatively charged and the positively charged chlorophyll and bacteriochlorophyll compounds and pharmaceutically acceptable salts thereof used in accordance with the invention are highly water soluble and enable the preparation of aqueous formulations with no added surfactants.

The pharmaceutical composition used in accordance with the invention is an ophthalmic composition, preferably a liquid e.g., a solution, suspension, and emulsion, or a gel that is topically applied to the eye of the patient and allowed to penetrate the cornea or the sclera before PDT is applied. The ophthalmic composition usually comprises inert pharmaceutically acceptable carriers and excipients that are well known in the art. The pharmaceutical composition may further contain one or more functional excipients, for example, for the purpose of mediating the depth of active agent penetration. Limiting the depth of photosensitizer penetration may be advantageous as it confines the treatment to the region of interest thereby minimizing adverse effects to adjacent tissues caused by the reactive oxygen species (ROS) formed upon illumination of the photosensitizer.

For preparation of pharmaceutical compositions, the photosensitizers may be lyophilized, for example, with mannitol, and the dry powder is directly solubilized in saline or any other pharmaceutically acceptable aqueous solution for topical application to a patient or for application on a sample in vitro target. The preparation of the compositions is carried out by techniques well-known in the art, for example as summarized in Remington: The Science and Practice of Pharmacy, Mack Publishing Co., Easton, Pa., 1990.

The present inventors found that penetration of several bacteriochlorophyll derivatives into rabbit corneas and sclera that were exposed to the photosensitizer for 10 or 30 min was significantly deeper when the photosensitizer was applied without dextran-500 than when applied with the excipient. Fluorescence microscope measurements of rabbit cornea presented in FIGS. 4A-4H indicate that the negatively charged bacteriochlorin derivative WST11 crosses half of the corneal stroma after 10 minutes of incubation and the entire stroma depth after 30 min of incubation in the absence of dextran. In contrast, application of WST11 with dextran-500 limited the penetration depth to the outer ⅓ of the corneal stroma after 10 minutes and to ~50% after 30 minutes of incubation. Similar results were obtained when the penetration depth of other sulfonated Bchls derivatives, namely compounds 1-7, was measured in the presence of dextran in the formulation.

Treatment with WST11 (or with compounds 1-7) mixed with dextran-500 did not alter the stiffening effect as compared to WST11 without dextran. However, it greatly reduced the treatment's adverse effects. Clinically, the duration and extent of corneal edema and epithelial healing was significantly shortened. Also, epithelial haze that formed in some treated corneas, appeared only in the absence of dextran. However, the most important effect appears to be the protection of the endothelial layer and the reduced impairment of keratocytes in the treated corneas. This is clearly demonstrated in the histological sections of rabbit eyes presented in FIGS. 11A-11C herein. Histology tests after treatment with WST11 (or with compounds 1-7) admixed with dextran 500, followed by NIR illumination showed reduction in keratocyte population in the anterior cornea with no damage to the endothelium.

This protection as well as the attenuated edema and shortened time of healing are probably related to the reduced depth of WST11 penetration and subsequently, the spatially limited effect of the photogenerated radicals. Surprisingly, while WST11 in saline penetrated half of the corneal stroma after 10 minutes of incubation, it produced less stiffening than WST11 applied with dextran after penetrating to a similar depth in the cornea. This observation may qualitatively correlate with the accumulation of WST11 at the cornea central layer and the possibility to generate a higher ROS concentration in this domain compared to the more diffused distribution of WST11 in the absence of dextran.

The protective role of dextran is probably maintained in the riboflavin (RF)/UVA treatment known in the art for stiffening cornea. Although formulation of RF with dextran-500 has been claimed to help maintaining solution isoosmolarity (Letko et al., 2011), it was recently reported that the stromal penetration of RF-dextran solution (RF-D) is limited to the anterior 200 μm, even under prolonged exposure time (Søndergaard et al., 2010). This finding corroborates with data obtained by the present inventors and substantiates the conclusion that dextran limits the anterior penetration of the photosensitizer into the cornea and thereby protects the endothelium from phototoxic effect. The molecular nature of this effect is yet to be determined but it emerges that the polysaccharide forms together with the natural colagen a matrix, which acts as a barrier that prevents migration of the photosensitizer into deeper layers.

Dextran is a high molecular weight polymer of glucose, digestible and degradable, which accounts for its wide use as an excipient for ophthalmic formulations, for example, artificial tears and eye drops. Dextran fractions are derived from the partial acid hydrolysis of native dextran, they have various properties, and uses, and are supplied in molecular weights ranging from 1000 to 2 million. The molecular weight of the fraction is in most cases a key property. The designation dextran 5, dextran 10 and the like represents the mean molecular weight divided by 1000. Thus, Dextran 10 corresponds to a mean molecular weight of 10,000. In certain embodiments, the dextran fractions are selected from dextran 50, dextran 70, dextran 100, dextran 200, dextran 500, dextran 1000 and dextran 2000. The most preferable dextran fraction used for the preparation of the ophthalmic composition of the invention is dextran 500.

When a 20% dextran 500 is added to the formulation it increases the viscosity of the formulation to about 179 cP.

An alternative approach to explain the reduced penetration depth of the photosensitizer when co-administered with dextran is increased viscosity of the formulation. The present inventors tested the effect of co-administering the photosensitizer with a solution of 65% glucose or 92% glycerol having a viscosity of 200 cP, comparable to that of 20% dextran solution. It turned out that a solution of 65% glucose or 92% glycerol limited the penetration depth of the photosensitizer to the same extent as dextran.

Thus, in more preferred embodiments, the present invention provides a viscous ophthalmic composition for treatment of corneal thinning. According to these embodiments, the ophthalmic composition comprises a viscous agent as an excipient that enhances the viscosity of the formulation and thereby restricts or delays the active agent penetration into the cornea. Any viscous agent used in ophthalmic formulations is suitable for the purpose of the invention. Preferred functional excipients that function as viscous agents are biopolymers, preferably polysaccharides, more preferably natural polysaccharides that are highly biodegradable in the body as a result of natural biological processes. Natural polysaccharides are advantageous also due to their unique physico-chemical properties, relatively low cost and since they can be chemically modified to suit specific needs. Non-limiting examples of polymeric viscous agents include dextran, scleroglucan and derivatives thereof, Gellan gum, Guar gum, methylcellulose (MC), polyvinyl alcohol, polyvinyl pyrrolidone, propylene glycol, polyethylene glycol, gelatin, carbomers and the like. Preferred viscous agents are dextran, and the exopolysaccharide hydrogels scleroglucan, particularly carboxylated derivatives thereof, Gellan gum and Guar gum.

Non-polymeric viscous agents that may be used in the ophthalmic formulation of the invention include glucose and glycerol.

Alternatively, the composition may be co-administered with a viscous, inert solution, such as, but not limited to, a solution of 20% dextran or 65% glucose or 92% glycerol.

The optical application of the bacteriochlorophyll derivatives in rabbit cornea and sclera followed by illumination at 600-900 nm, and the trapping of photogenerated oxygen radicals in the cornea and sclera, induced photochemical reactions, probably polymerization reactions, that resulted in consistent corneal and scleral stiffening ex vivo and in vivo. The photochemical reactions of the bacteriochlorophyll derivatives applied to the eyes of rabbits could be observed as a continuous bleaching and spectral modifications during illumination (the bleaching is shown herein in FIG. 5).

For rabbit cornea, ex vivo incubation with WST11 for 30 minutes prior to illumination increased the Young's modulus and the ultimate stress by 369% and 267%, respectively. Treatment with the same parameters performed in vivo raised the Young's modulus and ultimate stress by 174% and 111%, respectively. The Young's modulus increased with the incubation time for the cornea treated in vivo.

For rabbit sclera, ex vivo incubation with WST11 for 30 minutes prior to illumination, increased the Young's modulus and the ultimate stress by 300% and 274%, respectively.

Thus, PDT of cornea and sclera pre-treated with water soluble (bacterio)chlorophyll derivatives enhanced the ultimate stress and the Young's modulus by at least a factor of 2, with no damage to endothelial cells. This treatment appeared safe in the animal models and may therefore be considered for clinical trials in keratoconus and corneal ectasia after refractive surgery.

Thus, in another aspect, the present invention provides a method for photodynamic therapy of eye diseases, disorders and conditions associated with corneal thinning or scleral stretching, comprising the steps of: (a) administering to an individual afflicted with corneal thinning or sclera stretching a photosensitizer which is a (bacterio)chlorophyll of the formula I, II or III as defined above or a pharmaceutical composition comprising same; and (b) irradiating the eye with light at the red or near infrared (NIR) wavelength.

The method provided by the invention is advantageous over RF/UVA treatment. UVA irradiation was shown by several reports to be toxic to corneal endothelial cells (Wollensak et al., 2004(a); Wollensak et al., 2004(b); Wollensak 2010(a)) and to result in a complete loss of keratocytes (Spoerl et al, 2007; Hafezi et al., 2009; Wollensak et al., 2010(b)) even when the penetration depth of the applied RF was limited.

The mechanism involved in corneal stiffening by bacteriochlorophyll/NIR treatment may differ from that imposed by RF/UVA. Photoexcited water soluble bacteriochlorophyll derivatives such as WST11 generate superoxide and hydroxyl radicals with minimal traces of singlet oxygen which is the major ROS product of RF/UVA treatment (see FIG. 6).

In one embodiment, the method of the invention is applied for treatment of corneal thinning diseases, disorders and conditions selected from keratoconus, corneal ectasia caused by trauma, for example, post-laser-assisted in situ keratomileusis (LASIK) ectasia, post-photorefractive keratectomy (PRK) ectasia, post-infection ectasia, peripheral ectasia, atrophy, raised intraocular pressure or as a complication of photorefractive surgery in which the corneal stroma has been left thinner than about 250 μm.

Other non-limiting diseases and conditions associated with visual loss as a result of scleral and/or cornea anomalies that can be treated by the methods of the invention include rheumatoid condition of the cornea, degenerative myopia, regular myopia, scleral staphyloma, ocular hypertension glaucoma, low tension glaucoma and combinations thereof.

The combined treatment of (bacterio)chlorophyll photosensitizer and red or NIR irradiation of the eye may be used for preventing expected scleral weakening or corneal thinning in patients that intend to, or already underwent interventional procedures.

Thus, in a further aspect, the invention provides a method for preventing a corneal and/or scleral disease or weakening before, during or after interventional procedures, comprising the steps of: (a) administering to an individual expected to be afflicted with corneal and/or scleral disease or weakening, a chlorophyll or bacteriochlorophyll compound as defined above or a pharmaceutical composition comprising same; and (b) irradiating the eye with light at a red or near infrared (NIR) wavelength.

The amount of (bacterio)chlorophyll derivative to be administered for PDT therapy will be established by the skilled physician according to the experience accumulated with other Bchl derivatives used in PDT, and will vary depending on the choice of the derivative used as active ingredient, the condition to be treated, the mode of administration, the age and condition of the patient, and the judgement of the physician.

EXAMPLES

Materials and Methods (i) Compounds.

Palladium $3^1$-oxo-15-methoxycarbonylmethyl-rhodobacteriochlorin $13^1$-(2-sulfoethyl)amide monovalent salt (e.g.

the dipotassium salt WST11) was supplied by STEBA Laboratories, Israel. Palladium $3^1$-oxo-15-methoxycarbonylmethyl-rhodobacteriochlorin $13^1$-(-sulfopropyl)amide divalent salt (e.g., the dipotassium salt compound 1); palladium $3^1$-oxo-15-methoxycarbonylmethyl-rhodobacteriochlorin $13^1,17^3$-di-(2-sulfoethyl)amide divalent salt (e.g., the dipotassium salt compound 2); palladium $3^1$-oxo-15-methoxycarbonylmethyl-rhodobacteriochlorin $13^1,17^3$-di-(3-sulfopropyl)amide salt (e.g., the dipotassium salt compound 3); $3^1$-oxo-15-methoxycarbonylmethyl-rhodobacteriochlorin $13^1$-(2-sulfoethyl)amide salt (e.g., the dipotassium salt compound 4); $3^1$-oxo-15-methoxycarbonylmethyl-rhodobacteriochlorin $13^1$-(-sulfopropyl)amide salt (e.g., the dipotassium salt compound 5); $3^1$-oxo-15-methoxycarbonylmethyl-rhodobacteriochlorin $13^1,17^3$-di-(2-sulfoethyl)amide divalent salt (e.g., the dipotassium salt compound 6) and $3^1$-oxo-15-methoxycarbonylmethyl-rhodobacteriochlorin $13^1,17^3$-di-(3-sulfopropyl)amide divalent salt (e.g., the dipotassium salt compound 7), were prepared as described in U.S. Pat. No. 7,947,672. Other bacteriochlorophyll derivatives e.g., derivatives containing negatively charged groups or positively charged groups were prepared as described in U.S. Pat. No. 7,947,672 and WO 2005/120573. Solutions of the bacteriochlorophyll derivatives were prepared in two forms: (a) in saline only, at a concentration of 2.5 mg/ml and pH adjusted to 7.3 (herein referred to as "Bchl-S solution" or "Bchl-S"); (b) 2.5 mg/ml of a bacteriochlorophyll derivative in saline with 20% dextran 500 (31392 Fluka, Switzerland) and pH adjusted to 7.3 (herein referred to as "Bchl-D solution" or "Bchl-D").

Two forms of riboflavin (RF) solution were used: (a) 0.1% solution of riboflavin-5'-phosphate in saline, pH adjusted to 7.3 (herein referred to as "RF solution"); (b) commercial (Medio Cross, Germany) 0.1% solution of riboflavin-5'-phosphate in 20% dextran T-500, measured pH 6.8 (herein "RF-D solution" or RF-D").

(ii) Light Sources.

(a) Diode laser with tunable output up to 1 W at 755 nm (CeramOptec, Germany); (b) LED system at 760 nm 2×18 mW (Roithner Lasertechnik, Austria); and (c) LED system at 370 nm 2×3 mW (Roithner Lasertechnik, Austria).

(iii) Animal.

New Zealand white (NZW) rabbits were housed and handled with ad libitum access to food and water at the Core Animal Facility of the Weizmann Institute of Science (Rehovot, Israel). All experimental procedures were approved by the Institutional Animal Care and Use Committee. All experiments were done in adherence to the ARVO Statement for the Use of Animals in Ophthalmic and Vision Research.
Methods
(a) Corneal Studies
Biomechanical Testing of Corneal Stiffness (i) Sample Preparation for Ex Vivo Biomechanical Studies of Corneal Stiffening.

Eyes of rabbits (15-16 weeks old, weighting 3-4 Kg) were enucleated post mortem. Before enucleation, the 12 and 6 h position were marked on the sclera for preservation of subsequent cutting orientation. The corneas were de-epithelialized mechanically using a PKR scraper (Becton Dickenson, USA). Usually, about 10 rabbits were assigned to bacteriochlorophyll/NIR treatment, herein the "test group" (for example WST11/NIR), and 2 rabbits were treated by RF/UVA (herein the "RF/UVA group") for comparison. In the test group, 10 eyes of 10 rabbits were immersed upside down for 30 minutes in test compound saline solution (Bchl-S) followed by NIR illumination (600-900 nm) with a diode laser at 10 mW/cm$^2$ for 30 minutes. The untreated contralateral eyes served as controls. In the RF/UVA group, RF-D solution was topically applied on 2 eyes of 2 rabbits, every 10 minutes, for 30 minutes, followed by UVA irradiation at 370 nm by a double diode at 3 mW/cm$^2$, for 30 minutes. After treatment, the corneo-scleral rings were removed and placed on paraffin hemisphere buttons with a matching shape to establish accurate sectioning without tissue streching. Corneal strips, 4±0.2 mm in width, were cut from the epithelial side in a superior-inferior orientation, with a self-constructed double-blade cutter. The strips included 2 mm of sclera on both ends. Central corneal thickness was measured by ultrasonic pachymetry (Humphrey ultrasonic pachymeter, USA). The corneal strips were then transferred to the biomechanical tester.

(ii) Sample Preparation for In Vivo Studies

Twelve to twenty five weeks old rabbits (2.5-3 Kg weight) were used. They were anesthetized by intramuscular (i.m.) injection of 35 mg/kg ketamine (Rhone Merieux, Lyon, France) and 5 mg/kg xylazine (Vitamed, Binyamina, Israel). Usually, 16 rabbits were assigned for bacteiochlorophyll treatment. After de-epithelialization, one eye of each rabbit was treated topically with a test compound in saline for 10, 20 and 30 minutes using an eye cap (12 mm in diameter), followed by NIR illumination for 10, 20 or 30 minutes (755 nm, 10 mW/cm$^2$). The other eye served as untreated control. To prevent exposure of the limbal stem cells, the illuminated area was restricted by an aluminum foil mask with an 8 mm diameter central opening. To determine the role of dextran, 12 rabbits were divided into 4 treatment groups of 3 rabbits each: group 1, the Bchl-S group, was treated with a saline solution of a bacteriochlorophyll derivative; group 2, the Bchl-D group, treated with a bacteriochlorophyll-dextran solution. Both groups were incubated with the test compound for 20-min, followed by NIR illumination (755 nm, 10 mW/cm$^2$) for 30 minutes. Group 3, the RF group, was treated with riboflavin without dextran, and group 4, the RF-D group was treated with RF-dextran solution (RF-D). Both groups were incubated with RF or RF-D solutions for 30-minute, followed by UVA illumination (370 nm, 3 mW/cm$^2$) for 30 minutes. An ophthalmic ointment containing dexamethasone 0.1%, neomycin and polymixin B (Maxitrol®, Alcon, Belgium) was applied on the treated eyes once daily for two weeks. Four weeks after the treatment the rabbits were sacrificed, and the corneoscleral rings were removed and placed on paraffin hemisphere buttons of matching shape to assure accurate sectioning without stretching the tissue. Corneal strips, 4±0.2 mm in width, were cut from the epithelial side, as described above in the ex-vivo section. The corneal strips were transferred to the biomechanical tester without delay.

Drug Accumulation, Penetration and Photobleaching (i) Photosensitizer Overall Accumulation Eyes of rabbits were de-epithelialised mechanically immediately post mortem. For most studies, 6 rabbits were used, wherein 6 eyes of 6 rabbits were exposed to the bacteriochlorophyll test compound for 10, 20 and 30 minutes (2 eyes for each test) using an eye cap, while the contralateral eyes were left untreated and served as controls. The corneas were removed and the central buttons of 8-mm diameter were punched out with a round trephine and placed onto the outer side of a polymethylmethacrylate cuvette in the area of light beam passage. Absorption spectra were recorded, and optical density (OD) at 600-900 nm (in most cases at 755 nm) was measured using V-570 spectrophotometer (Jasco, Japan).

(ii) Depth Penetration Studies

Eyes of rabbits were enucleated and deepithelialised mechanically post mortem. The eyes were exposed to Bchl-S solution using an eye cap for 5, 10, and 30 minutes and to Bchl-D solution for 10 and 30 min, in darkness. Controls: untreated eyes, and one eye treated with dextran-500 only for 30 min in darkness. Following this pretreatment, the corneas were briefly rinsed with saline and the central 8-mm buttons were trephined, removed, wrapped in aluminum foil and frozen on dry ice until further use. Central serial corneal sagittal slices (12 µm) were cut with a cryomicrotome, mounted on a microscope glass slide and stored frozen in −70° C. until use. For measurement of fluorescence, the individual slices were placed on the microscope base and a photographic record was immediately taken. Fluorescence intensity of Bchl-S or Bchl-D treated corneas from 3 serial cryo sections was recorded at 760 nm, upon excitation at 740 nm, using a fluorescence microscope (BX61 Olympus, Japan) equipped with CCD camera (Cascade 512B, Roper Sci., USA) and a long pass filter of above 760 nm. The digital data was analyzed, using ImageJ software (NIH, USA).

(iii) Photobleaching of Photosensitizes

Corneas of eyes from euthanized rabbits were de-epithelialized. Usually, 5 rabbits were tested, and 8 of the 10 eyes were pretreated for 20 minutes with a bacteriochlorophyll derivative in saline (Bchl-S), using an eye cap. The solution excess was carefully tipped off with filter paper. The eyes were irradiated for the specified time duration: 0, 10, 30, and 60 min (two corneas per time frame). Additional two eyes were used as control. The corneas were removed, and the central buttons of 8-mm diameter were punched out with a round trephine. Absorption spectra were recorded using V-570 spectrophotometer (Jasco, Japan).

Fluorescence Spectroscopy Following Bchl/NIR and RF/UVA Treatment

Figure 2:
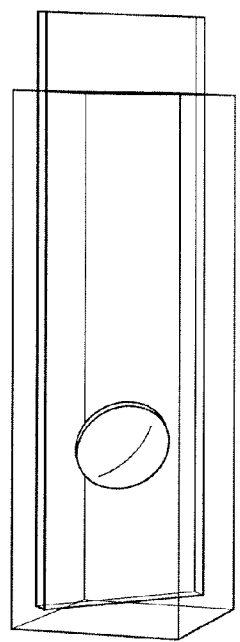
FIG. 2 is an illustration of a central corneal disc, 8 mm in diameter, mounted on a glass slide that was placed obliquely in a quartz cuvette for fluorescence spectroscopy measurements after WST11/NIR and RF/UVA treatment.

Rabbit eyes were enucleated post mortem. The corneal epithelium was de-epithelialised with a scraper. Usually, two eyes of two rabbits were immersed in Bchl-S or Bchl-D solutions for 30 min, followed by NIR irradiation (30 min). RF-D solution was applied on two eyes for 30 min, followed by UVA irradiation (30 min). Two eyes served as controls. The corneas were removed and the central 8-mm buttons were punched out with a round trephine. The buttons were mounted on a glass slide that was placed obliquely at 45° (FIG. 2) in a spectrofluorimeter (Varian-Cary Eclipse, USA). Excitation beam was set at 295, 315, 320, 328, 335 nm and corresponding emission spectra were read at 360 to 480 nm. Other readings were performed with excitation at 350 nm and emission at 380-480 nm, and excitation at 370 nm and emission at 400-700 nm. Excitation slit was 10 nm, emission slit ~10 nm.

Histology

Forty eight hours or 1 week after treatment with Bchl-S, Bchl-D, RF or RF-D, rabbits were euthanized, and the eyes were immediately enucleated and fixed in Davidson's fixative (48 hour post treatment) or in 4% formaldehyde (1 week post treatment). Six-µm sections were prepared from either the whole eye or corneas and stained with hematoxylin-eosin (H&E). The pathology of the corneal and retinal sections was examined. The sections were photographed with a digital video camera (Nikon DS-Ri1, Japan), mounted on a light microscope (E-800 Leica, Germany). Keratocyte and endothelial cell densities were counted in 2 areas of 2 central histological sections and calculated, using Image-Pro software (MediaCybernetics, MD, USA).

Staining for Apoptosis.

For apoptosis detection, rabbits were euthanized one day post Bchl-S or Bchl-D treatment. Their corneas were removed, fixated in 4% formaldehyde and embedded in paraffin. Six-µm central sections were prepared from the corneas, placed on microscope slides and deparaffinized. Peroxidase-based terminal deoxyribonucleotidyl transferase-mediated dUTP-digoxigenin nick and labeling (TUNEL) assay was performed according to the manufacturer's instructions (Apop-Tag assay, Chemicon, Merck Millipore, Darmstadt, Germany).

Endothelial Staining.

Rabbits underwent analysis of corneal endothelial damage 1 day post treatment, using alizarine red S and trypan blue staining as described in Spence and Peyman, 1976. The treatment included either a 20-minute pretreatment with Bchl-S or Bchl-D solutions, followed by 30-minute irradiation at 755 nm (2 rabbits), or only a 30-minute irradiation at 760 nm (2 rabbits). Contralateral non-treated eyes served as controls.

(b) Scleral Studies

Sample Preparation for Ex Vivo Biomechanical Studies of Scleral Stiffening

Rabbit eyes were enucleated immediately post mortem and treated externally by applying an eye cap with a 2.5 mg/ml of a test compound in saline (Bchl-S) for 30 minutes on the superior or inferior sclera, followed by irradiation with NIR at 10 mW/cm$^2$ for 30 minutes. The opposite side of the sclera served as control. Scleral strips, 4 mm in width, were cut at the equatorial treated area and the opposite sclera, and stress-strain measurements were performed using a biomaterial tester.

Impregnation Measurements

Ex-Vivo Impregnation:

Eyes of euthanized rabbits were enucleated, and the superior equatorial sclera (or inferior equatorial) was exposed to a test compound (Bchl-S) solution (2.5 mg/ml) for 10 minutes and 30 minutes using an eye cap of 10 mm diameter filled with the test compound. The inferior equatorial sclera (or the superior equatorial sclera, if impregnation was applied to the inferior equator) served as control.

In Situ Impregnation:

Test compound solution was applied in the supero-temporal or infero-nasal (alternating) quadrant of the rabbit by a curved plastic or metal glide with attached Merocel® sponge connected by a tube that ran along the glide outside. The glide was inserted through a conjunctival opening at the limbus (see FIGS. 17A-17B). After placing the glide attached to the sclera, the tube was connected to a syringe or pump, and the test compound reservoir was injected to impregnate the sclera. Application of the photosensitizer was continued for 10 or 30 minutes. Afterwards, the glide with the Merocel® was withdrawn.

The following technique was performed after ex-vivo or in-situ impregnation of photosensitizer:

The treated scleral area and the opposing control sclera were trephined with a round skin trephine of 8-mm diameter and scissors and immediately frozen. Sagittal slices of 20 microns were dissected with a cryomicrotome at the central area of the scleral button. The fluorescence intensity at 755 nm was recorded upon excitation at 740 nm using a fluorescence microscope (Olympus, Japan).

Illumination In Vivo Through the Anterior Segment.

NIR illumination was performed through the cornea and lens by a diode laser with a fundus contact lens (Volk pan-fundoscopic) or by mounting the optic fiber to an indirect ophthalmoscope, and using a +20 diopter lens applying the light on the sclera through the retina and pigment epithelium. The illumination intensity was adjusted accordingly due to the attenuation of the light.

After illumination, the rabbits were euthanized, their eyes were enucleated, and the treated scleral area and the opposing control sclera were trephined with a round skin trephine of 8-mm diameter and scissors. The scleral buttons were frozen immediately. Sagittal slices of 50 microns were performed with a cryomicrotome at the central area of the scleral button. Fluorescence spectroscopy was performed using a fluorescence microscope (Olympus, Japan), and fluorescence intensity at 755 nm was recorded upon excitation at 740 nm.

(c) Biomechanical Testing

The corneal and scleral strips were clamped horizontally, at a distance of 6 mm, between the jaws of a microcomputer-controlled biomaterial tester (Minimat, Germany) with a 200 Newton force cell (FIG. 1). Controlled tightening of screws was performed with a calibrated screwdriver at a preset torque of 9 cN·m (Torqueleader, England). The strain was increased linearly at a rate of 1.0 mm/min and was measured up to tissue rupture. Young's modulus was calculated by the testing machine. Ultimate stress and Young's modulus were expressed in Mega Pascal (MPa) units.

(d) Electron Spin Resonance (ESR) Spectroscopy

All ESR measurements were carried out using a Magnettech ESR Miniscope MS 100 Spectrometer (Germany), with a Microwave X-band Bridge. The ESR spectrometer operates at 9.3-9.55 GHz, 20 mW microwave power. ESR measurements were carried out at room temperature in glass capillaries or flat cells.

Samples of aqueous solutions of bacteriochlorophyll derivatives without or with dextran (Bchl-S and Bchl-D, respectively), and of riboflavin without or with dextran (RF and RF-D, respectively), were illuminated at 755 nm as described in Ashur et al, 2009. To each solution, the spin-trap α-(4-pyridyl N-oxide)-N-tert-butylnitrone (4-POBN, 65 mM) and ethanol (8%) were added. Controls contained illuminated 4-POBN in saline with/without dextran, and non-illuminated Bchl-S, Bchl-D, RF and RF-D solutions with/without 4-POBN.

Ex-Vivo ESR Measurements of Rabbit Corneas.

Eyes of rabbits were enucleated post mortem. The corneas were de-epithelialized mechanically and corneal strips, 5 mm in width, were cut with a self-constructed double-blade cutter. The strips were immediately immersed for 30 mM in solutions containing 4-POBN (65 mM) and ethanol (8%), and either Bchl-S or RF-D. Next, the strips were washed with saline and put in the flat-cells (0.5×5 mm$^3$) for NIR/UVA illumination followed by ESR measurements with the aforementioned Miniscope.

Example 1

WST11 Uptake by Rabbit Corneal Tissue (i) Overall Accumulation of WST11 by the Rabbit Cornea Six eyes of 3 euthanized rabbits were de-epithelialized mechanically immediately post mortem. Five of these eyes were exposed to WST11 in saline (WST11-S solution) for 10, 20 and 30 min, using an eye cap, and the optical absorption at 755 nm of the washed corneas was determined as described in Materials and Methods. One eye served as untreated control.

Figure 3:
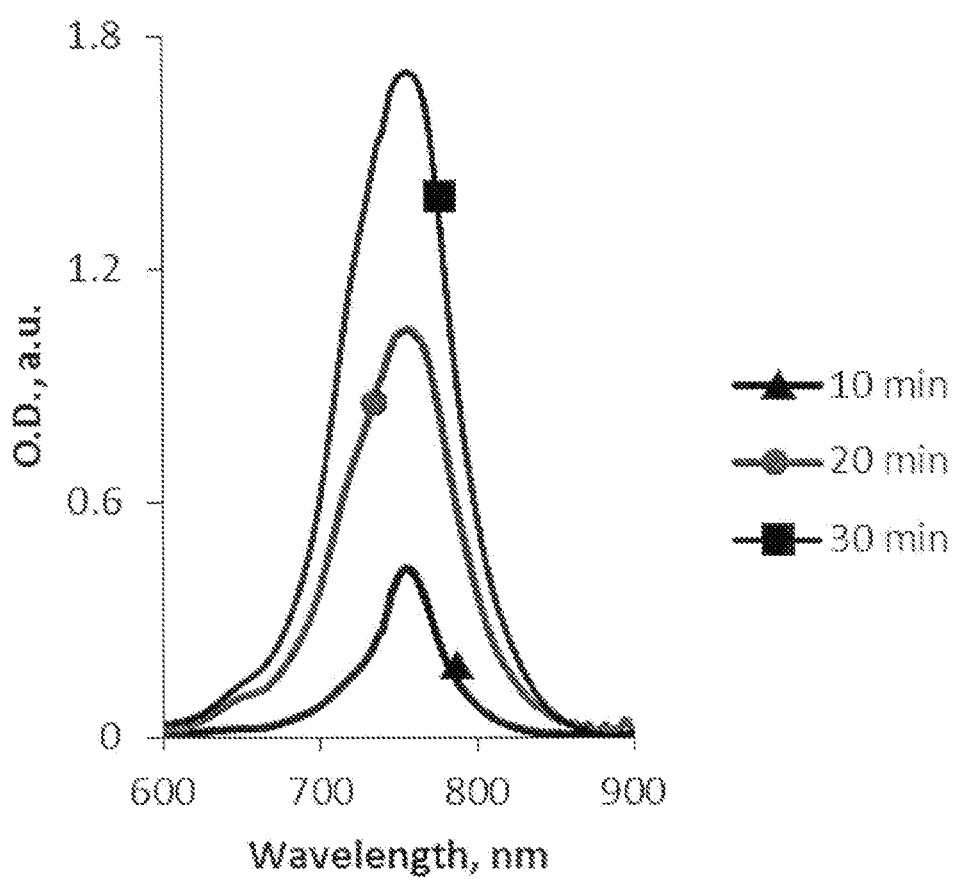
FIG. 3 are optical absorption spectra (755 nm) of WST11 accumulated in de-epithelialized corneas of rabbit exposed to a solution of WST11 in saline for 10, 20 and 30 minutes.

As shown in FIG. 3, the optical density of the impregnated corneas increased with time up to a value of 1.71 OD units, without interference with the native spectrum of WST11.

(ii) WST11 Depth of Penetration into the Rabbit Cornea

Upon topical application, the penetration and the depth of photochemical impact on the corneal tissue was determined for several bacteriochlorophyll derivatives. Results are provided herein for measurements with WST11.

The penetration depth of the photosensitizer determines the extent of cornea's tissue exposure to the photodynamic effect. In particular, the deeper the penetration, the higher is the probability for endothelial impairment. To resolve the penetration depth of test compounds following different times of incubation, the digitized fluorescence of dissected corneal discs was monitored using fluorescence microscopy as described in Materials and Methods.

The penetration depth of WST11 into the de-epithelialized cornea, following various incubation times, was performed in the darkness in the absence or presence of dextran, using saline or dextran solutions of WST11 (WST11-S or WST11-D solutions, respectively) in 20 eyes of euthanized rabbits. Sagittal frozen sections mounted on glass slides were subjected to fluorescence microscopy. The distribution of WST11 across the cornea was recorded photographically by fluorescence microscopy (excitation/emission 740/760 nm). The controls were 4 untreated eyes and 1 eye treated only with dextran-T 500 for 30 minutes.

Figure 4A:
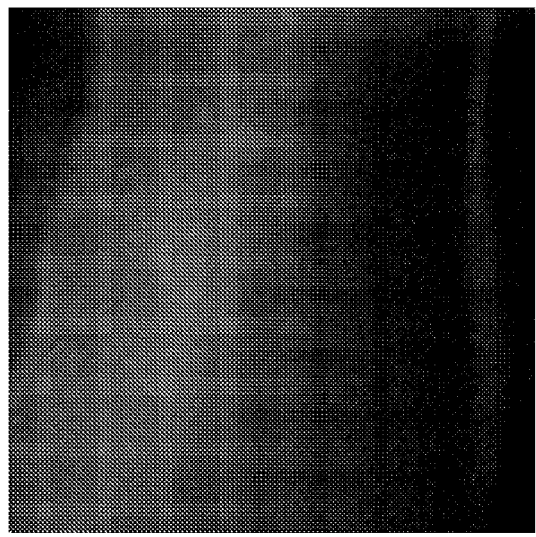
FIGS. 4A-4H are fluorescence microscope pictures (FIGS. 4A, 4B, 4E, 4F) and graphs related thereto (FIGS. 4C, 4D, 4G, 4H), showing fluorescence intensity versus penetration depth into de-epithelialized rabbit corneas that were exposed ex-vivo to WST11 in saline for 10 minutes (4A and 4C) and 30 minutes (4B and 4D), and to a solution of WST11 and dextran-500 for 10 minutes (4E and 4G), and 30 minutes (4F and 4H). Fluorescence of central corneal sagittal slices (12 μm) was detected at 760 nm upon excitation at 740 nm.
Figure 4B:
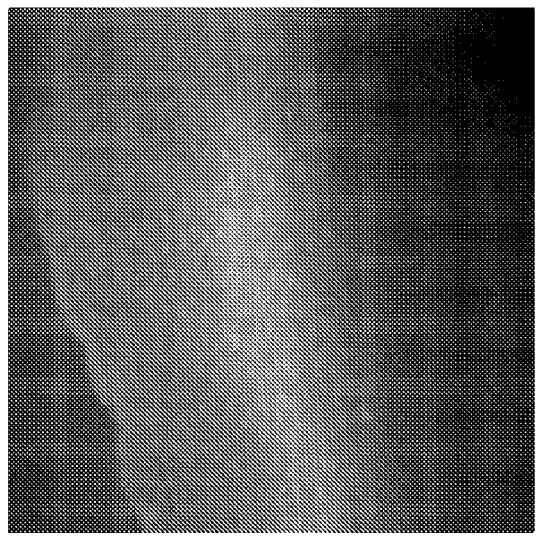
Figure 4C:
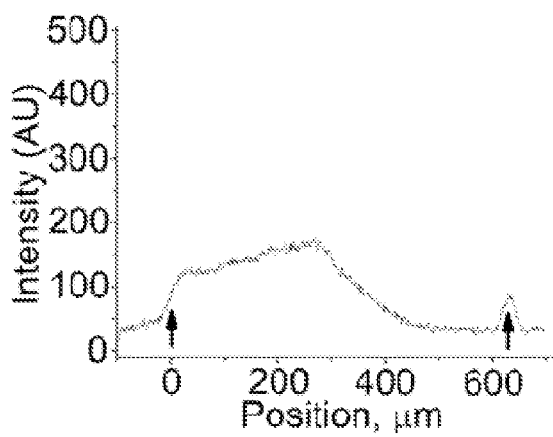
Figure 4D:
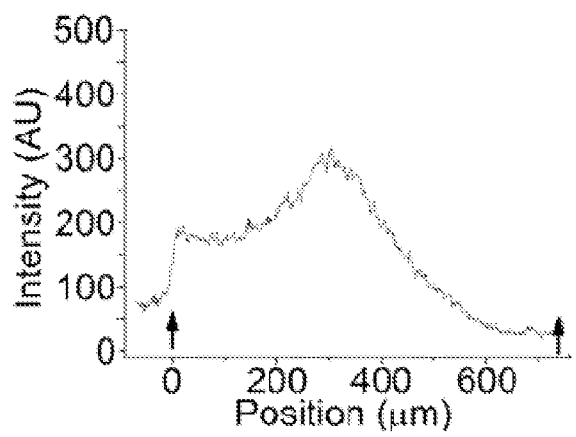
Figure 4E:
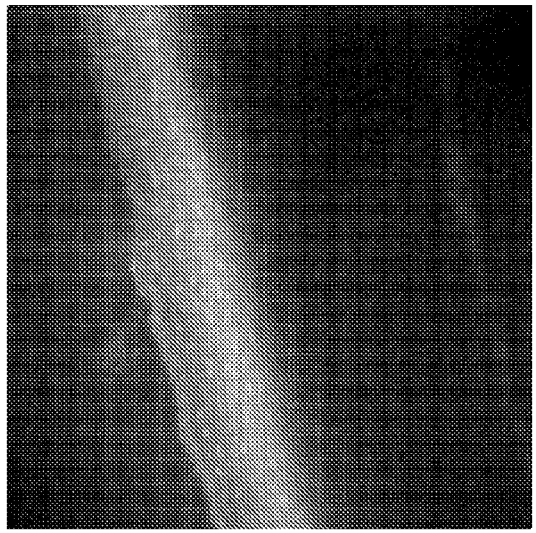
Figure 4F:
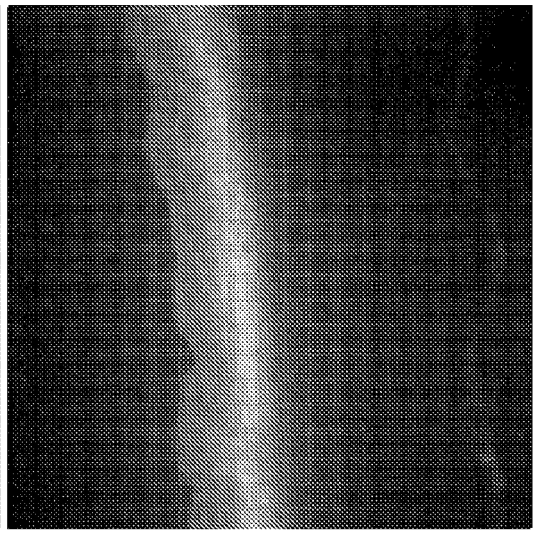
Figure 4G:
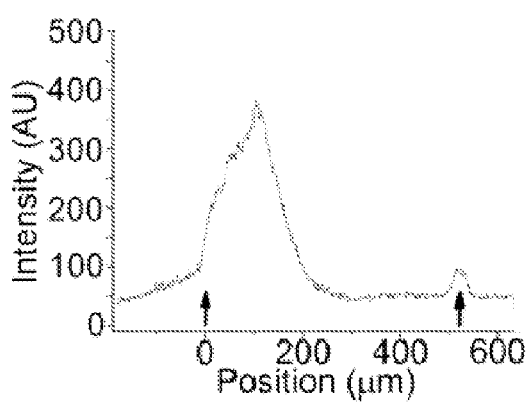
Figure 4H:
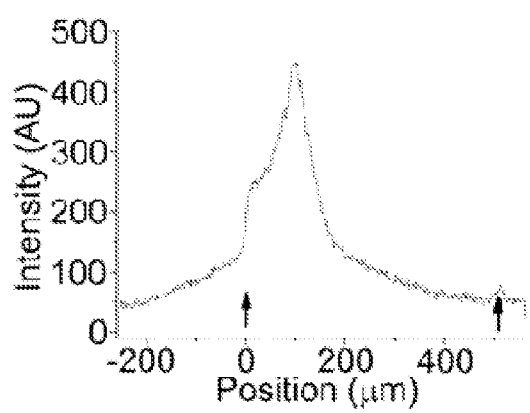

Following 10 minutes of exposure (of 2 eyes) to WST11-S solution, WST11 was evident through the entire outer half of the stroma (FIGS. 4A, 4C). Further exposure (30 minutes; 5 eyes) resulted in diffused fluorescence all the way to Descemet's membrane (FIGS. 4B, 4D). This treatment increased the stromal thickness from 360-380 μm to 600-730 μm. In contrast, application of WST11-D solution limited the penetration depth to the outer ⅓ (200 out of 520 μm) of the corneal stroma, at both 10 and 30 minutes exposure times (3 eyes and 5 eyes were tested, respectively) as shown in FIGS. 4E, 4G and FIGS. 4F, 4H, respectively. Importantly, the fluorescence of WST11-D in the cornea showed a relatively sharp front of drug migration that did not exceed the center of the stroma. However, at the depth of 200 μm the level of fluorescence was still higher for corneas following 30 minute exposure to WST11-D suggesting a higher accumulation level.

Comparable results for corneal impregnation and penetration depth were obtained with saline and dextran solutions of compounds 1-7. (data not shown).

Example 2

Photochemistry of WST11 in the Cornea (i) Photobleaching of WST11 in Ex-Vivo Treated Corneas It was previously described by the present inventors that generation of oxygen radicals upon illumination of certain bacteriochlorophyll derivatives such as WST11 in the absence of serum albumin is accompanied by bleaching of the NIR transition and absorption increase at ~645 nm due to the photochemical generation of a chlorophyll-like molecules (Ashur et al. 2009). Such changes are therefore important markers for the photochemical activity of such bacteriochlorophyll derivatives in situ. Hence, the changes in the optical absorption of several sulfonated bacteriochlorophyll derivatives during cornea illumination were monitored in de-epithelialized corneas of rabbits. Results obtained for 10 corneas of 5 euthanized rabbits treated with WST11 in saline are presented herein.

Figure 5:
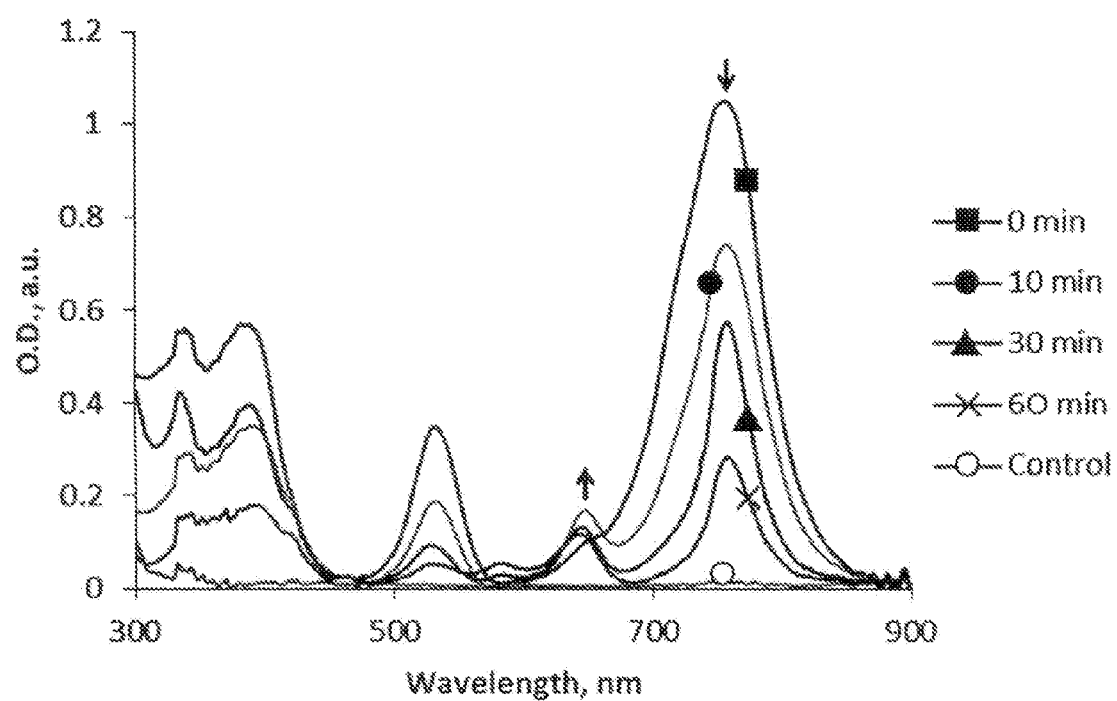
FIG. 5 are optical absorption spectra of WST11 from corneas ex-vivo treated with WST11 solution for 20 minutes prior to illumination at 755 nm, 10 mW/cm$^2$, for the specified time durations.

Eight de-epithelialized eyes were retreated with WST11-S for 20 min using an eye cap, and the remaining 2 eyes served as control. As shown in FIG. 5, the 755-nm absorption of corneal WST11 diminished by 30, 50 and 75% after NIR illumination for 10, 30 and 60 min, respectively (downward arrow). In parallel, the absorption increased at 645 nm (upward arrow), typical to the corresponding chlorin derivative formation by the photochemical interaction of WST11 with molecular oxygen (Ashur et al., 2009)

Figure 6:
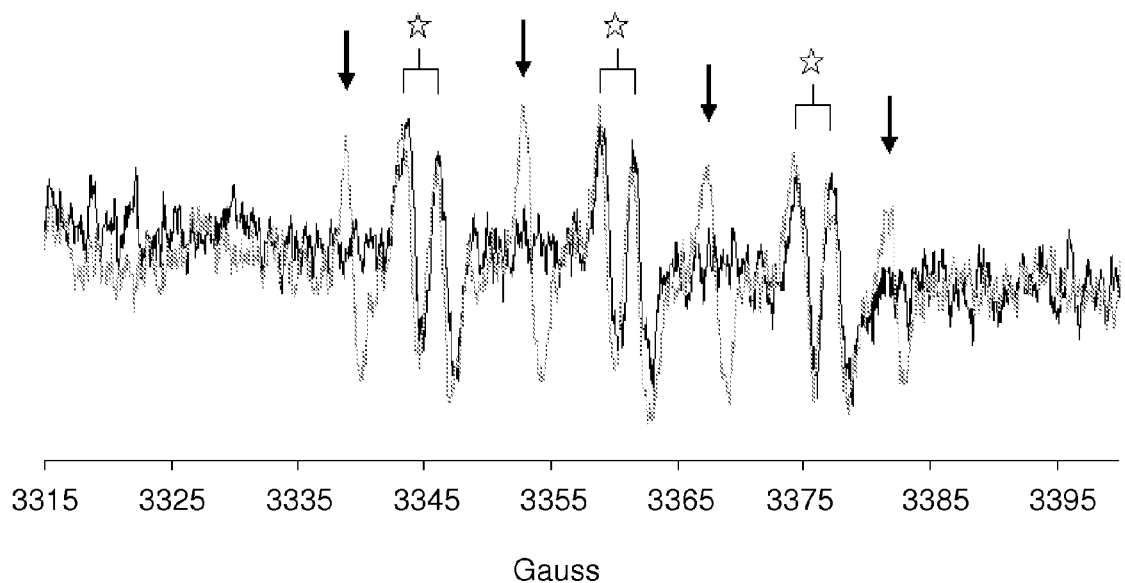
FIG. 6 is an electron spin resonance (ESR) spectrum of α-(4-pyridyl N-oxide)-N-tert-butylnitrone (4-POBN, 65 mM) in solution containing ethanol (8%) and WST11 (black) or RF (light blue), following NIR or UVA irradiation, respectively. The black arrows shows the quartet formed upon trapping singlet oxygen by 4-POBN, and the stars shows the double-triplet formed upon trapping hydroxyl and superoxide radicals.

(ii) Oxygen Radical Formation by Photoexcited WST11 in the Cornea Deduced from Electron Spin Resonance (ESR) Spectroscopy Comparison of the ESR spectra of α-(4-pyridyl N-oxide)-N-tert-butylnitrone (4-POBN) in aqueous solution following photoproduction of reactive oxygen species (ROS) by WST11/NIR (black) and RF/UVA (light blue) and spin trapping by 4-POBN, are presented in FIG. 6. The observed quartet due to singlet oxygen trapping is present only in the RF/UVA spectra, while the sextet represents superoxide and hydroxyl radical formation (stars) in both WST11/NIR and RF/UVA.

Figure 7:
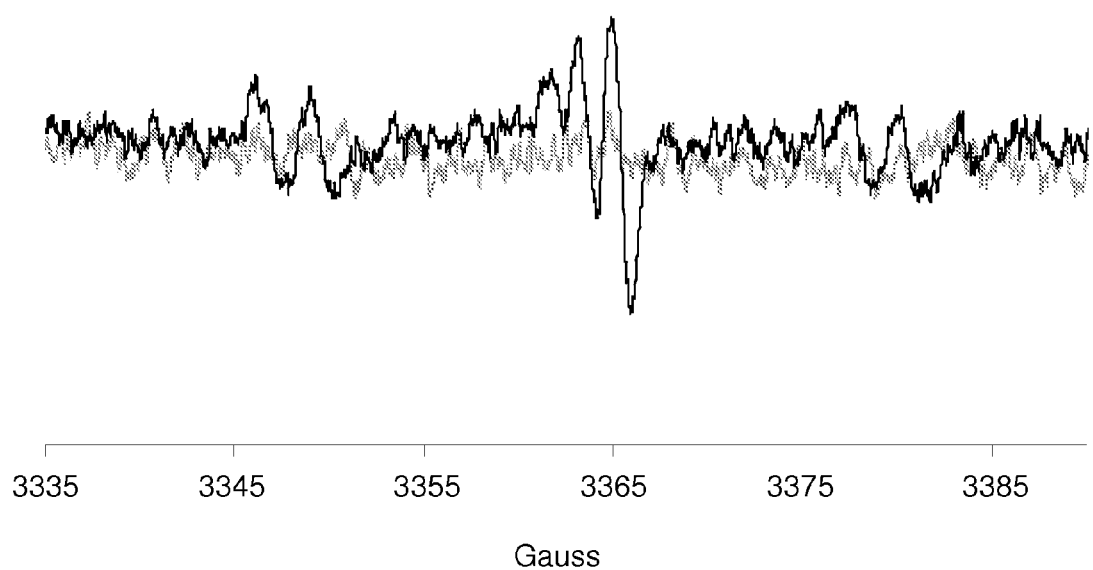
FIG. 7 are ESR spectra of 4-POBN obtained form ex-vivo WST11/NIR (black) or RF/UVA (light blue) treated corneas, following immersion in a 4-POBN (65 mM) ethanol-(8%) solution.

ESR measurements of ROS trapped in the rabbit cornea treated by WST11/NIR is shown in FIG. 7. The signals are similar to those observed in aqueous solutions with no traces of singlet oxygen. The signals generated by RF/UVA were at the noise level.

Example 3

Corneal Stiffening in Response to WST11-S/NIR Treatment

Stress-Strain Measurements of Ex-Vivo Treated Eyes

Stress-strain measurements were conducted in 12 rabbits as described in Materials and Methods. Briefly, 10 eyes of 10 rabbits were treated by WST11/NIR, and 2 eyes of 2 rabbits were treated by RF-D/UVA. The contralateral eyes served as control.

Figure 8A:
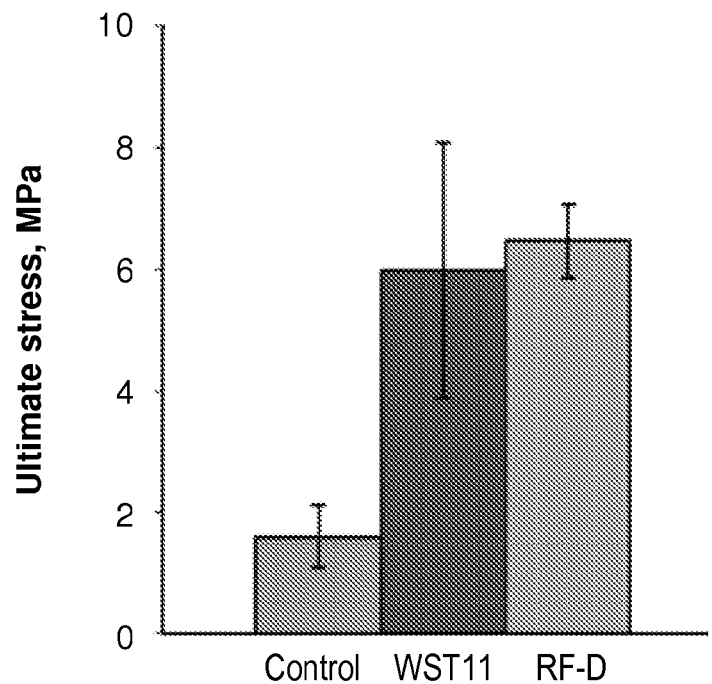
FIGS. 8A-8B are graphs presenting ex vivo stress-strain measurements values of corneal stiffness in ultimate stress units (8A) and Young's modulus (8B) of corneas after 30-min. incubation with WST11 followed by 30-min. NIR illumination (n=10), or incubation with RF-D solution followed by UVA irradiation (RF-D/UVA).
Figure 8B:
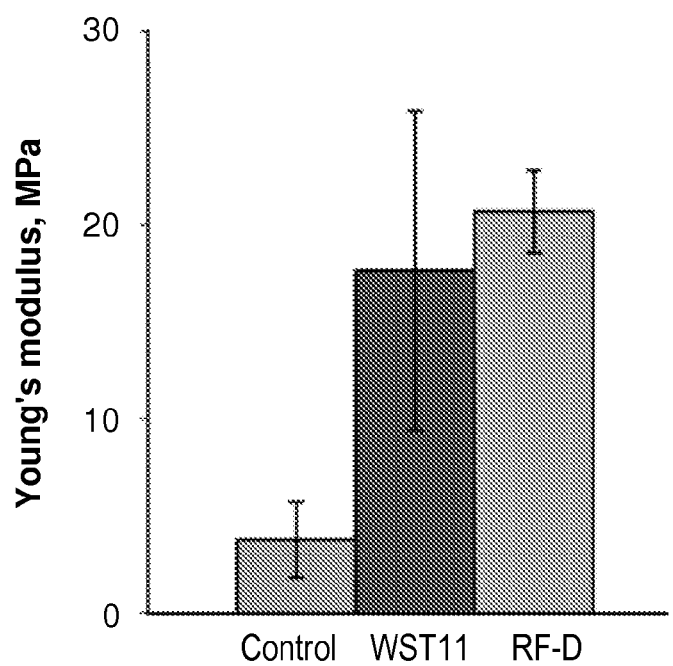

The stress-strain measurements following 30 min preincubation with WST11-S and then NIR illumination, showed a nearly 3-fold increase in the corneal stiffness (of all 10 eyes) as compared to the untreated control eyes (FIGS. 8A-8B). There was a maximal increase of 267% in the ultimate stress (P<0.0001) from a mean of 1.63 MegaPascal (MPa) without treatment to 5.98 MPa after treatment and an increase of 369% in Young's modulus (P<0.0001), from a mean of 3.76 MPa without treatment to 17.65 MPa after treatment. The results are depicted in Table 1.

The mean ultimate stress in the two RF-D/UVA-treated corneas increased from 1.44 MPa without treatment to 6.46 MPa after treatment and in the mean Young's modulus from 3.28 MPa without treatment to 20.72 MPa after treatment.

Thus, stiffening due to WST11/NIR treatment appeared similar to that observed in the two RF-D/UVA treated corneas.

Stress-Strain Measurements of In-Vivo Treated Eyes

Figure 9A:
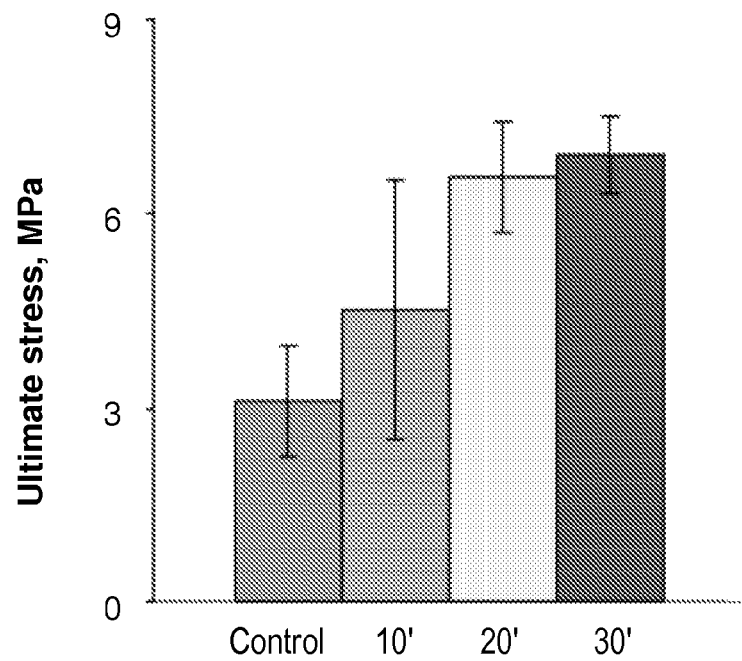
FIGS. 9A-9B are graphs presenting in vivo stress-strain measurements values of corneal stiffness in ultimate stress units (9A) and Young's modulus (9B), 1 month after treating rabbit corneas with WST11 (2.5 mg/ml) for 10, 20, or 30 minutes, followed by 30-min NIR illumination (755 nm, 10 mW/cm$^2$), or after RF/UVA treatment.
Figure 9B:
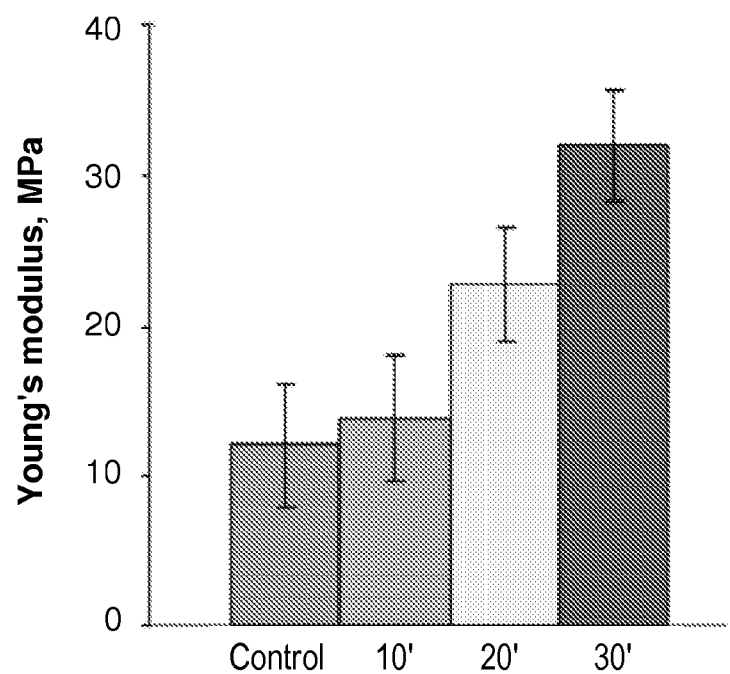

Corneas of 16 live rabbits were pretreated for 10 (n=4), 20 (n=6) and 30 (n=6) minutes with WST11-S (2.5 mg/ml). NIR illumination (755 nm, 10 mW/cm$^2$) was then delivered for 30 minutes. The eyes were allowed to heal, and one month later the ultimate stress of the treated corneas was measured (as described in Material and Methods), and found to increase by 45, 113, and 126%, respectively, as compared to the non-treated eyes. The mean Young's modulus in WST11-S/NIR-treated corneas showed a 10, 79 and 173% increase for the same treatment times. Results are shown in FIGS. 9A-9B, and in Tables 1 and 2.

Corneas treated by WST11-S/NIR developed edema for one week after treatment. The corneal epithelial defect healed gradually after 10-14 days. After epithelial healing, the corneas regained transparency, with some corneas demonstrating epithelial haze.

TABLE 1 rabbit cornea stiffening following WST11-S/NIR treatment

| Setting | Sample | Mean ultimate stress | | Mean Young's Modulus | |
|---|---|---|---|---|---|
| | | Intensity (MPa) | Increase % (P value) | Intensity (MPa) | Increase % (P Value) |
| Ex vivo | Control: untreated fellow eyes n = 10 | 1.63 ± 0.58 | | 3.76 ± 1.96 | |
| | WST11/NIR treated eyes n = 10 | 5.98 ± 2.11 | 286 (<0.0001) | 17.65 ± 8.25 | 410 (<0.0001) |
| In vivo 30 days | Control: untreated fellow eyes n = 6 | 3.06 ± 0.67 | | 11.7 ± 2.6 | |
| | WST11/NIR treated eyes n = 6 | 6.91 ± 0.53 | 111 (0.0049) | 32 ± 3.6 | 174 (0.0035) |

TABLE 2

Effect of WST11 incubation time on rabbit corneas stiffening

| | Sample | Mean ultimate stress | | Mean Young's Modulus | |
|---|---|---|---|---|---|
| | | Intensity (MPa) | Increase % (P value) | Intensity (MPa) | Increase % (P Value) |
| In vivo | Control: untreated fellow eyes n = 10 | 3.12 ± 0.73 | | 12.69 ± 3.31 | |
| | WST11 10 min treated eyes n = 4 | 4.51 ± 1.85 | 45 (0.1446) | 13.9 ± 3.9 | 9 (0.183) |
| | WST11 20 min treated eyes n = 6 | 6.66 ± 0.67 | 113 (<0.0001) | 22.7 ± 3.82 | 79 (0.0028) |

Notably, the in-vivo rabbits were 12 weeks old at the time of treatment, and 16 weeks old when sacrificed, while the ex-vivo group rabbits were sacrificed at the age of 12 weeks. The aging resulted in a higher baseline Young's modulus and ultimate stress values of the control eyes (Table 1) that probably accounts for the gap between the parameters achieved in the two settings (Knox et al., 2010; Elsheikh et al., 2007).

Stress-strain measurements of rabbit cornea were conducted, both ex vivo and in vivo as described above, but exposing the eyes to saline solutions of Compound 1-3 for the indicated times, followed by NIR illumination. The ultimate stress and Young's modulus values obtained for these compounds were similar to those obtained with WST11-S (data not shown).

Example 4

In Vivo Cornea Treatment by WST11-D/NIR

To determine the role of dextran, the photochemical treatment with a formulation of WST11 2.5 mg/ml containing 20% dextran T-500 (WST11-D) was examined. Six rabbits were examined: 3 rabbits were pretreated for 20 min with WST11-S solution and 3 with WST11-D solution, followed by NIR illumination for 30 minutes. Additional 4 rabbits were treated with RF (n=2) or RF-D (n=2) for 30 minutes, followed by 30-min UVA irradiation (370 nm, 3 mW/cm$^2$).

Figure 10A:
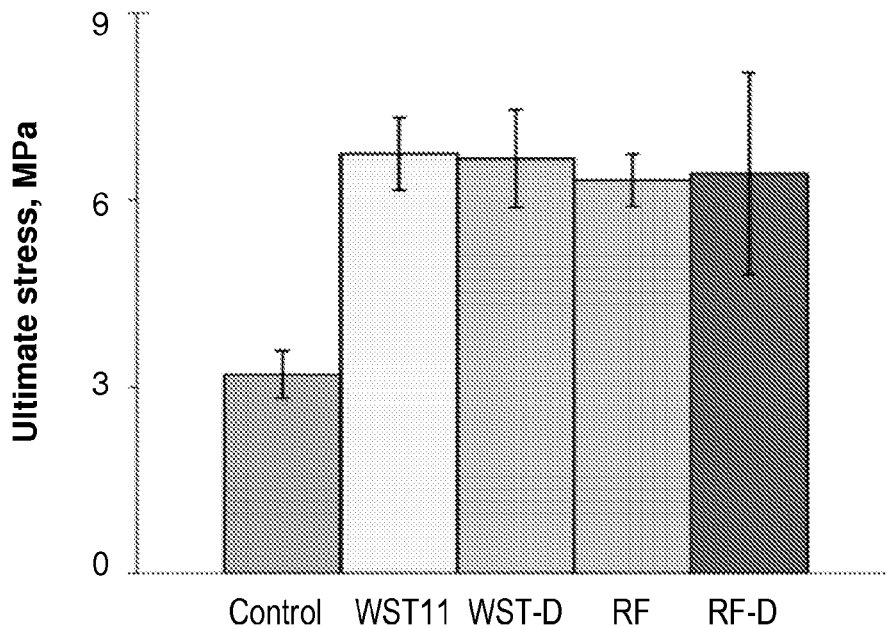
FIGS. 10A-10B are graphs presenting in vivo stress-strain measurements values of corneal stiffness in ultimate stress units (10A) and Young's modulus (10B), 1 month after treating rabbit corneas either with WST11 (2.5 mg/ml) in saline without dextran (WST11), or WST11 with dextran 500 (WST-D) for 20 minutes, followed by 30-min NIR illumination (755 nm, 10 mW/cm$^2$), or after treatment with RF with or without dextran, followed by 30-min UVA irradiation. Control-untreated eyes.
Figure 10B:
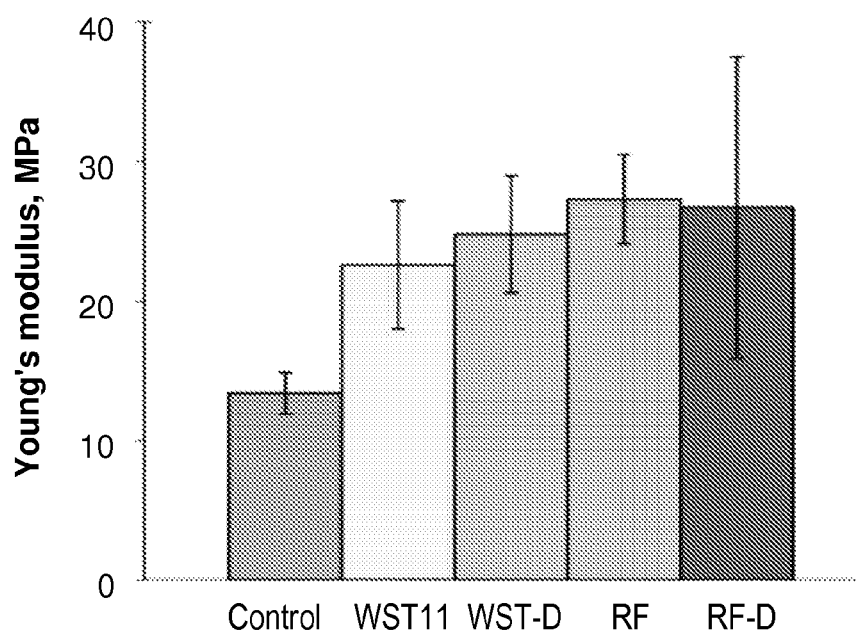

As shown in FIGS. 10A-10B, application of WST11-S or WST11-D did not appear to affect the approximately two-fold increase in both the mean ultimate stress and Young's modulus, as compared with untreated corneas of fellow eyes.

However, the important finding is that treatment with WST11 significantly reduced the extent and duration of the edema and epithelial defect compared to RF-D/UVA treatment. Corneal edema cleared after 5 days, and the epithelium healed within 7-9 days without haze development. In the RF and RF-D treated corneas, the epithelial defect healed after 4 days. In the RF-D group the edema resolved after 4 days with recovery of transparency, whereas in the RF group the edema persisted for 6 days, followed by 2 days of central epithelial haze.

Example 5

Endothelial and Keratocyte Response to WST11-S/NIR or WST11-D/NIR Treatment

The endothelial and keratocyte response of rabbits' eyes to incubation with saline or dextran solutions of WST11 and Compounds 1-7, followed by NIR illumination were studied. The effects of these various bactriochlorophyll solutions were practically the same. Detailed results are provided herein for measurements with WST11.

One rabbit underwent treatment with WST11 in saline (WST11-S; 20-minute incubation, 30-minute irradiation at 755 nm). Six rabbits underwent treatment with WST11D (n=4, 20-minute incubation, 30-minute irradiation at 755 nm), or with RF-D (n=2, 30-minute incubation, 30-minute irradiation at 370 nm) as described above (In-vivo studies section). Contralateral eyes were used as control.

Figure 11A:
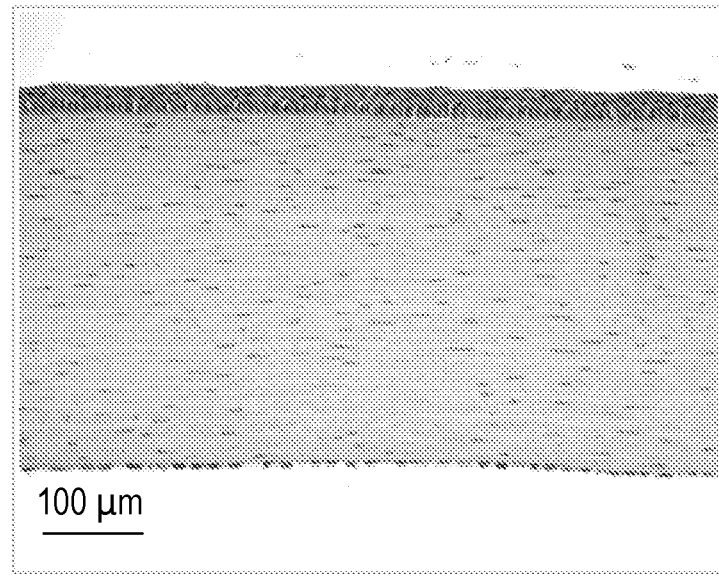
FIGS. 11A-11C are histological sections of rabbit corneas stained with hematoxylin-eosin two days (11A-11C) or 1 week (11D) post in vivo WST11/NIR illumination treatment (×20 magnification). 11A: control; 11B: cornea treated with WST11 in saline (WST11-S/NIR protocol); 11C: cornea treated with WST11 and dextran (WST11-D/NIR); 11D: 1 week after WST11-D/NIR treatment.
Figure 11B:
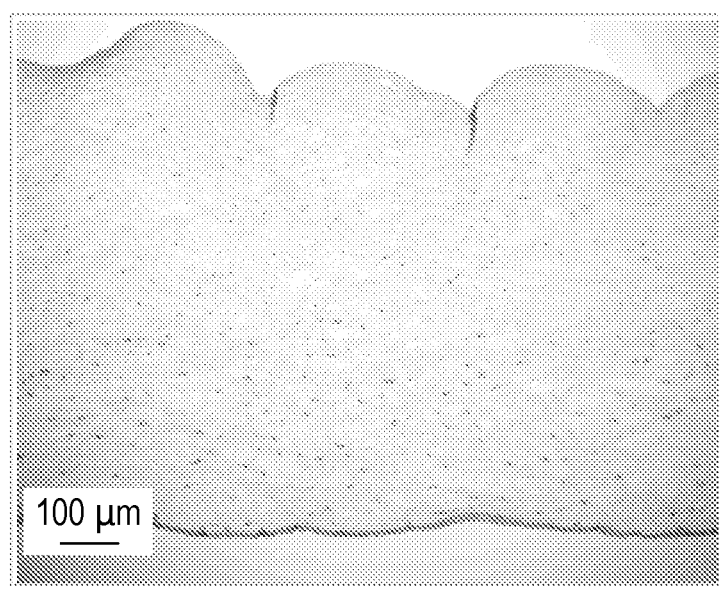
Figure 11C:
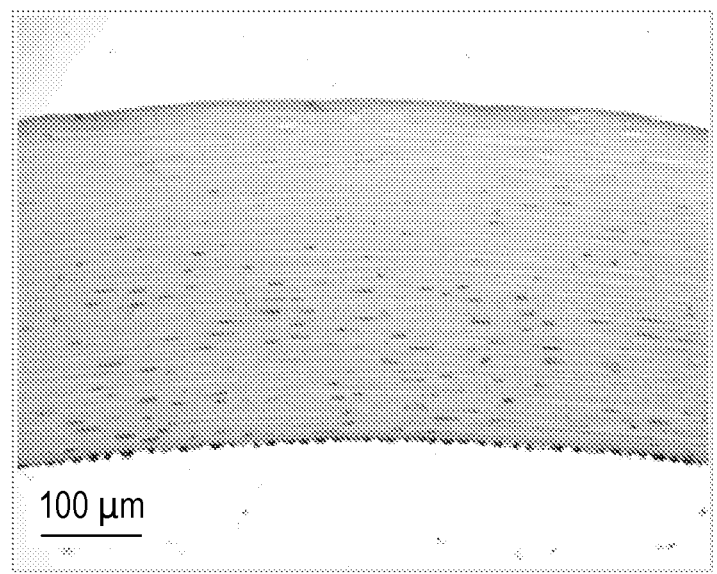
Figure 11D:
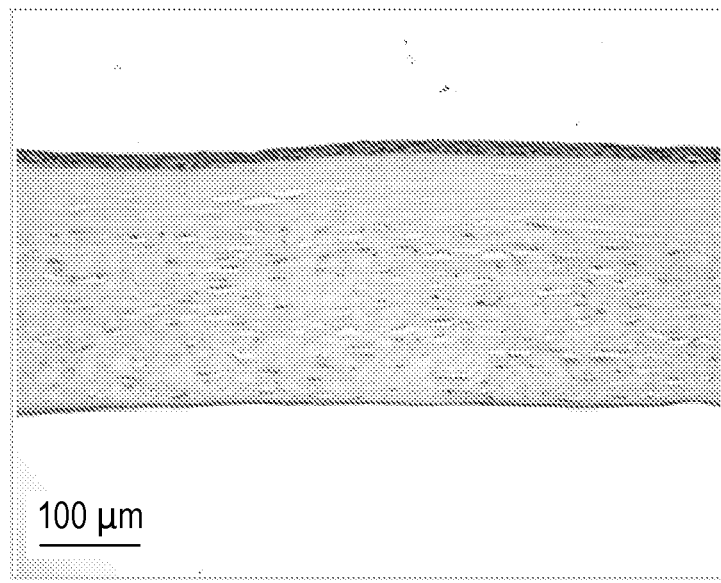

Histological examination of the corneas two days after WST11-S/NIR treatment showed marked edema (cornea swelling to 890 µm), and a reduced number of keratocytes throughout the stroma, more pronounced in the anterior half (see FIG. 1B). A honeycomb-like lacunar hydration pattern, containing keratocytes or keratocyte debris, was present. However, the endothelial cell layer appeared intact and did not differ from the control (FIG. 11A). There was no statistical difference in the endothelial counts between treatment and control (P=0.47). In contrast, corneas treated with WST11-D showed minimal corneal edema, absence of the epithelium in the central area and a statistically significant reduction in the number of keratocytes (481±121 cells/mm$^2$ in the treated corneas, as compared to 1060±210 cells/mm$^2$ in controls, P<0.0001) limited to the outer half of the stroma (FIG. 11C). There was no evidence of damage to the endothelium in comparison to the control, both after vital (data not shown) and H&E staining (FIG. 11A). One week after treatment, the histological sections showed shrinkage of the anterior stroma to 250 µm (in addition to the stromal compaction to 340 µm that occurred following formaldehyde fixation of control samples), loss of keratocytes in the anterior ⅓ of the stroma (80 µm) with epithelial healing, but no endothelial damage (FIG. 11D). H&E staining of the retina two days after WST11-D/NIR treatment did not show any morphological changes compared with control (data not shown).

Figure 12A:
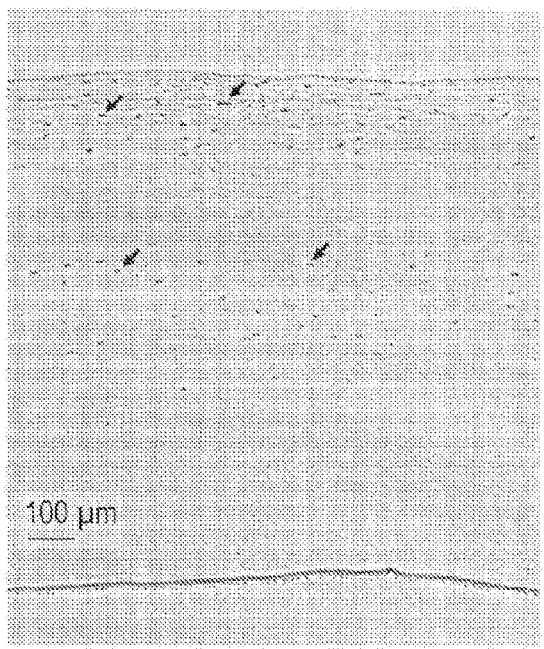
FIGS. 12A-12B are histological sections of rabbit corneas stained for apoptosis 1 day after in vivo treatment with WST11 in saline followed by NIR illumination. 12A—Control, untreated cornea; 12B WST11-S/NIR treated cornea.
Figure 12B:
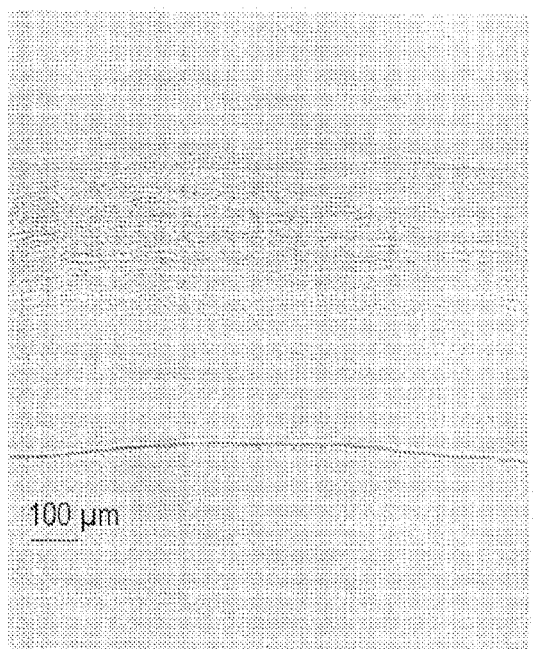

Apoptosis was examined using peroxidase-based terminal deoxyribonucleotidyl transferase-mediated dUTP-digoxigenin nick and labeling (TUNEL) assay. One day postoperatively, TUNEL-positive keratocytes were detected in the outer ½ of anterior stroma of treated corneas, as shown in FIG. 12B. No staining for TUNEL was observed in the posterior stroma the endothelium was absent and there was edema of the central stoma, as in the control corneas (FIG. 12A).

Example 6

Fluorescence Spectroscopy of Rabbit Corneas

Eight rabbit eyes were enucleated post mortem and corneal endothelium was de-epithlialized. Three eyes were immersed in SWT11-S solution and 3 eyes in SWT11-D solution for 30 minutes, followed by NIR illumination. Two eyes were treated with RF-D solution for 30 minutes, followed by UVA irradiation. Contralateral eyes served as control. Fluorescence of segments of the corneas was measured as described in Materials and Methods.

Figure 13:
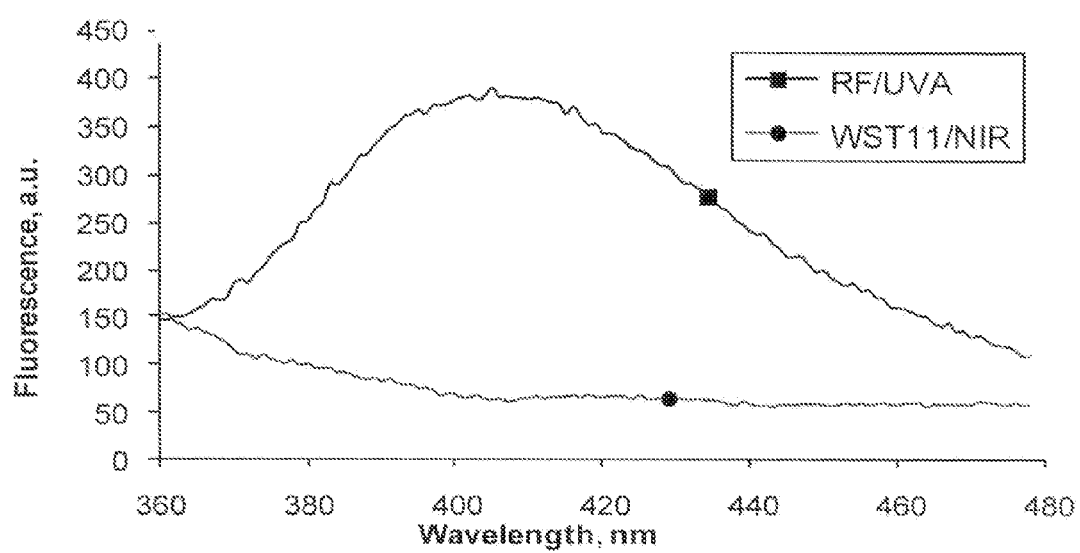
FIG. 13 presents fluorescence spectra of rabbit corneas treated with WST11 and NIR irradiation (WST11/NIR), or treated with riboflavin and UVA irradiation (RF/UVA).

Excitation of the RF-D/UVA treated corneas at 320 nm generated a clear emission signal at 405 nm that probably corresponded to the fluorescence of dityrosine, a known signature of cross linking (Kato et al., 1994). Such emission was absent in the WST11-S/NIR and WST11-D/NIR treated corneas, and in the controls as shown in FIG. 13. Excitation at any other wavelength did not provide any significant change in the cornea emission profile.

Example 7

Palladium Based Measurement of Systemic Absorption of Topically Applied WST11-D

Six rabbits were anesthetized as described in the Materials and Methods. After de-epithelialization, one cornea of each rabbit was treated with WST11-D 2.5 mg/ml (n=3) and 10 mg/ml (n=3) for 20 minutes using an eye cap. Blood samples (~0.5 ml) were taken from the ear vein before application (time 0), and at 10, 20, 40 and 60 minutes after application began, placed in pre-weighed polyethylene 1.5 ml test tubes, weighted and lyophilized. The dry samples were digested with nitric acid, and Pd concentrations were determined by inductively-coupled plasma mass spectrometry (ICP-MS) using a set of Pd standards (High-purity Standards, USA) as previously described (Mazor et al, 2005).

ICP-MS measurements of blood samples drawn from rabbits during and after topical application of WST11-D could not detect any significant levels of $Pd^{+2}$, as an evidence for no penetration of the drug into the circulation of the treated animals at all measured time points.

Example 8

Thermographic Analysis of the Corneal Surface

Three rabbits were treated with WST11-D for 20 minutes, followed by NIR illumination (755 nm, 10 mW/cm²) for 30 minutes. Temperature measurements on the corneal surface were performed during WST11-D/NIR treatment using an IR thermocamera (Thermal imager InfRec R300, NEC Avio Infrared Technologies Co., Ltd., Tokyo, Japan) with thermal resolution 0.05° C., temperature accuracy of ±1° C. and a spatial resolution of 120 µm. Images were recorded before irradiation, every 7 minutes during irradiation and at the conclusion (last seconds) of irradiation. Selected thermographic images were processed with InfReC Analyzer NS9500 Lite (NEC Avio Infrared Technologies Co., Ltd., Tokyo, Japan).

A constant temperature gradient from T=32° C. at the corneal center to T=37.5° C. at the limbal periphery was measured before, during and after treatment. Deviations of less than 1° C. were observed throughout the whole procedure (data not shown).

Example 9

Transepithelial Delivery of WST11 into Rabbit Cornea

Permeability of the cornea to drugs is clinically important because it is the major factor determining the efficacy of topically applied ophthalmic formulations. To study the transepithelial penetration of the ophthalmic formulations of the invention, the delivery of SWT11 was assessed in the presence of a known transepithelial permeability enhancing excipient comprising benzalkonium chloride solution containing NaCl.

Two rabbits were anesthetized and treated as follows:
In one eye of each rabbit, the epithelium was removed, and the central corneal area was incubated with a 2.5 mg/ml solution of WST11 in 0.9% sodium chloride, pH 7.3, using eye cap during 20 minutes. In the contralateral eye the epithelium was left intact and the central corneal area was incubated with a 2.5 mg/ml solution of WST11 in 0.44% sodium chloride containing 0.02% benzalkonium chloride, pH 7.3, using eye cap, during 20 minutes, and then the epithelium was removed.

Following incubation with the photosensitizer, the animals were euthanized, central corneal discs of 8 mm in diameter were removed, and photosensitizer's overall accumulation was estimated by recording absorption spectra and measurement of OD at 755 nm as described in Materials and Methods.

Accumulation of WST11 in the de-epithelialized corneas resulted in optical density (OD) of about 0.86 in one rabbit and about 0.75 in the second rabbit. Transepithelial corneal accumulation resulted in OD of about 0.12 in the first rabbit which is about 14% of WST11 accumulated in the de-epithelialized cornea, and about 0.16 in the second rabbit, which is about 21% of the photosensitizer that accumulated in the de-epithelialized cornea.

Thus, under the condition applied above, the amount of photosensitizer delivered by transepithelial corneal incubation can be ~⅙ of the amount accumulated in de-epithelialized cornea.

Example 10

Penetration Depth in Cornea of WST11 in Aqueous 65% Sucrose Solution

Aqueous 65% sucrose solution has similar viscosity as 20% dextran T-500 (~175 cP). The penetration depth of topically applied photosensitizer in a formulation comprising 65% sucrose was tested in corneas of rabbits. The results described herein were obtained for WST11 in 65% sucrose solution.

Two rabbits were anesthetized, their corneas were de-epithelialized and one eye of each rabbit was treated with a 2.5 mg/ml solution of WST11 in aqueous 65% sucrose solution, pH 7.3, using eye cap, during 10 minutes, and the contralateral eye was similarly treated but for 30 minutes. Then, the animals were euthanized, central corneal discs of 8 mm in diameter were removed, deep frozen and cut for sagittal slices as described in Materials and Methods.

After 10-min. incubation the photosensitizer penetrated to ~⅓ of the outer stroma, and after 30-min. incubation to ~½ of the outer stroma, in both animals (data not shown). Thus, a 65% sucrose solution can be applied as effectively as dextran for limiting photosensitizer penetration into cornea.

Example 11

WST11 Depth of Penetration into the Rabbit Sclera

Figure 14:
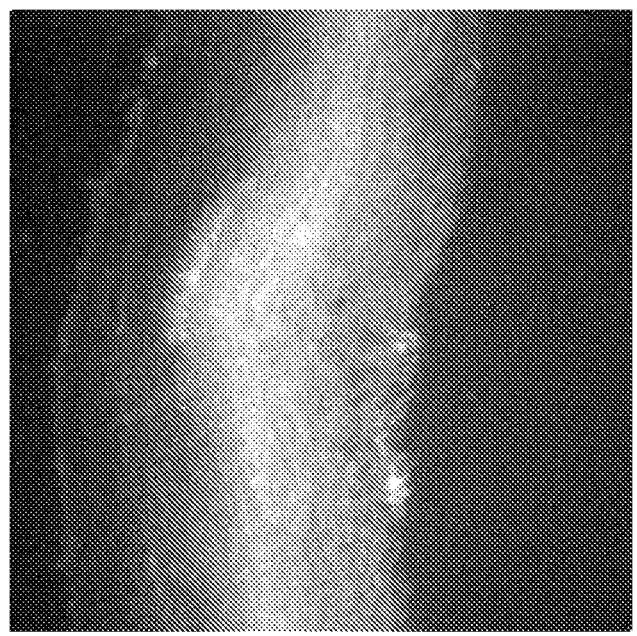
FIG. 14 is a fluorescence microscope picture of rabbit sclera showing penetration of WST11.

The depth of penetration of WST11 into rabbit sclera was assessed by fluorescence microscopy as described in Materials and Methods. The results shown in FIG. 14 indicate that WST11 applied ex vivo using eye cap and in-situ using Merocel® sponge penetrated into sclera tissue.

Example 12

Figure 17A:
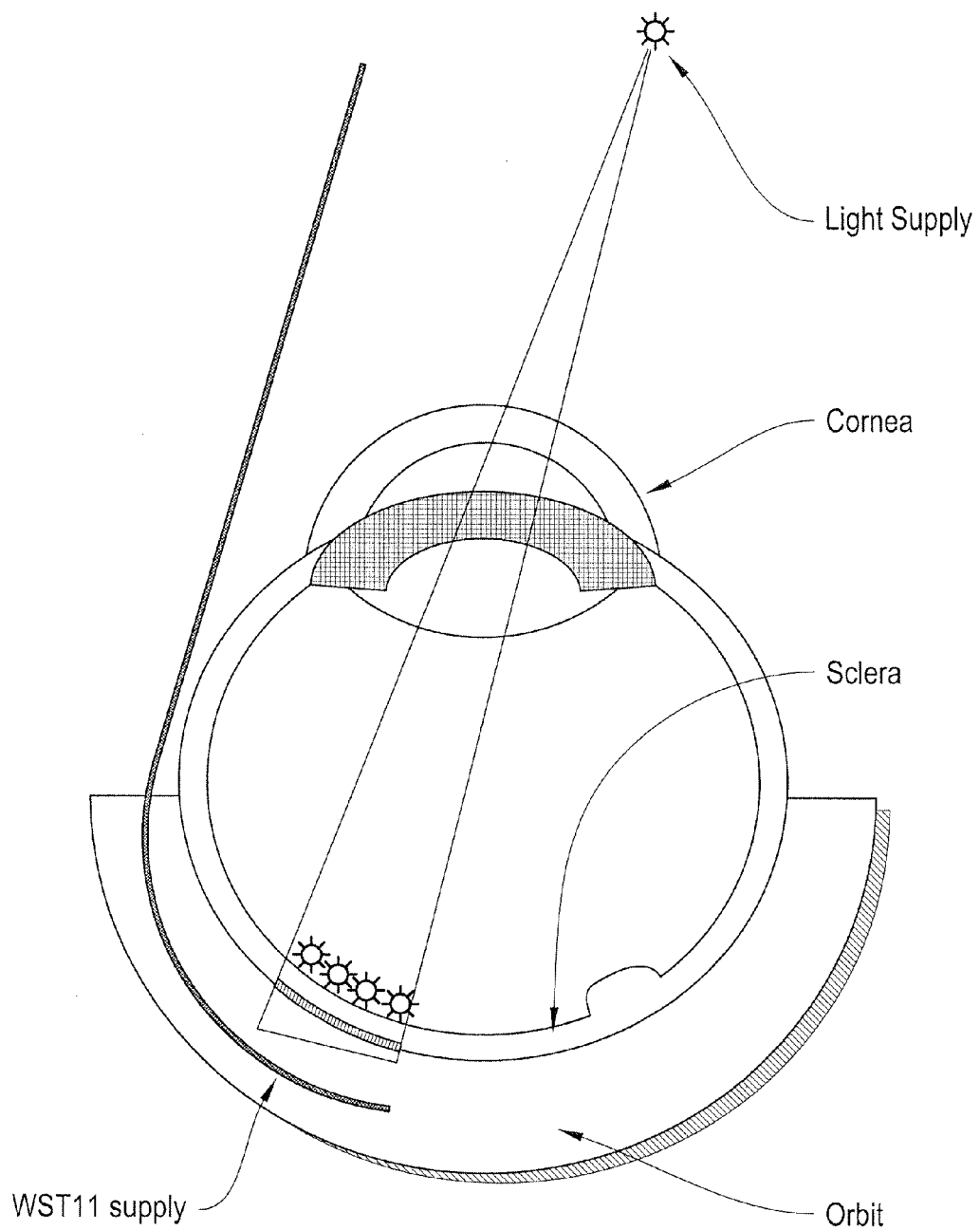
FIGS. 17A-17B are schematic illustration of the apparatus used for ex-vivo drug delivery to the sclera and external or direct illumination (17A) and illumination through the anterior cornea (17B).

Biomechanical Testing of Rabbit Sclera Treated Ex Vivo with WST11-S and External NIR Illumination Stress-strain tests of sclera of enucleated rabbits' eyes were performed following treatment with WST11 (2.5 mg/ml) as described in Materials and Methods. After photosensitizer impregnation, the sclera was illuminated by applying the laser beam directly onto the treated area (external illumination), using a flat optical fiber that run along a curved plastic or metal glide as shown in FIG. 17A. Strips of the sclera were cut and tested.

Figure 15A:
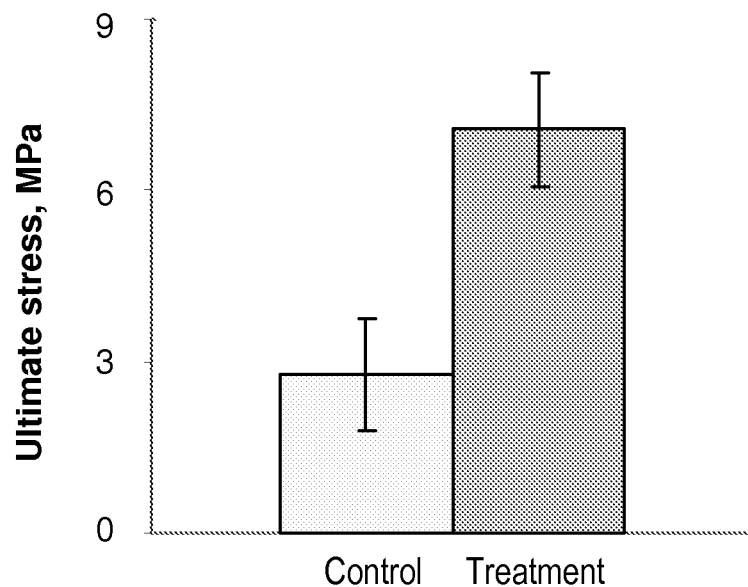
FIGS. 15A-15B are graphs presenting ex vivo stress-strain measurements values of upper equatorial sclera stiffness in ultimate stress units (15A) and Young's modulus (15B) of corneas after 30-min incubation with WST11 followed by 30-min direct NIR illumination (755 nm, 10 mW/cm$^2$) onto the posterior treated sclera. Control—untreated lower equatorial sclera.
Figure 15B:
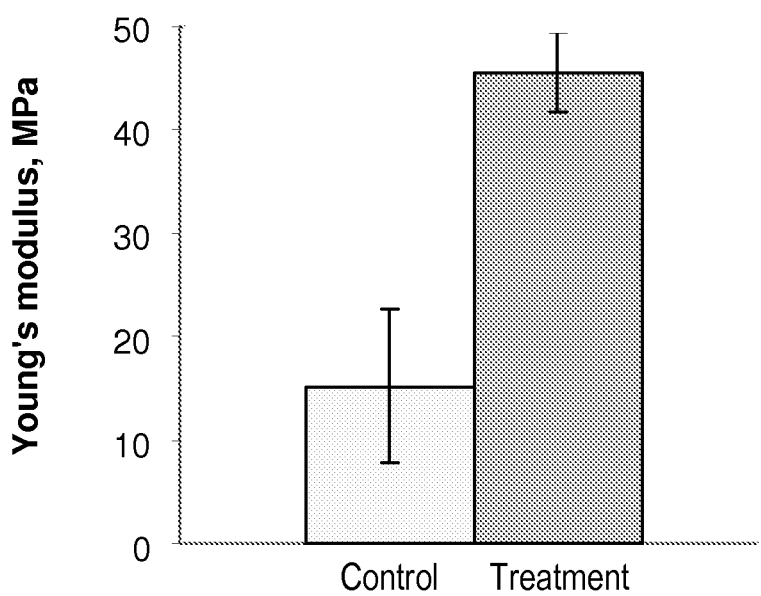

The measurements demonstrated a significant increase in the stiffness of the treated sclera. The mean maximal stress in the control sclera was 2.77±0.99 MPa. The mean maximal stress in WST11/NIR treated sclera was 7.6±0.99 MPa (174% increase). The mean Young's modulus in control sclera was 15.2±7.5 MPa. The mean Young's modulus in WST11/NIR treated sclera was 45.6±3.9 MPa (200% increase). The results are shown in FIGS. 15A-15B.

Example 13

Figure 17B:
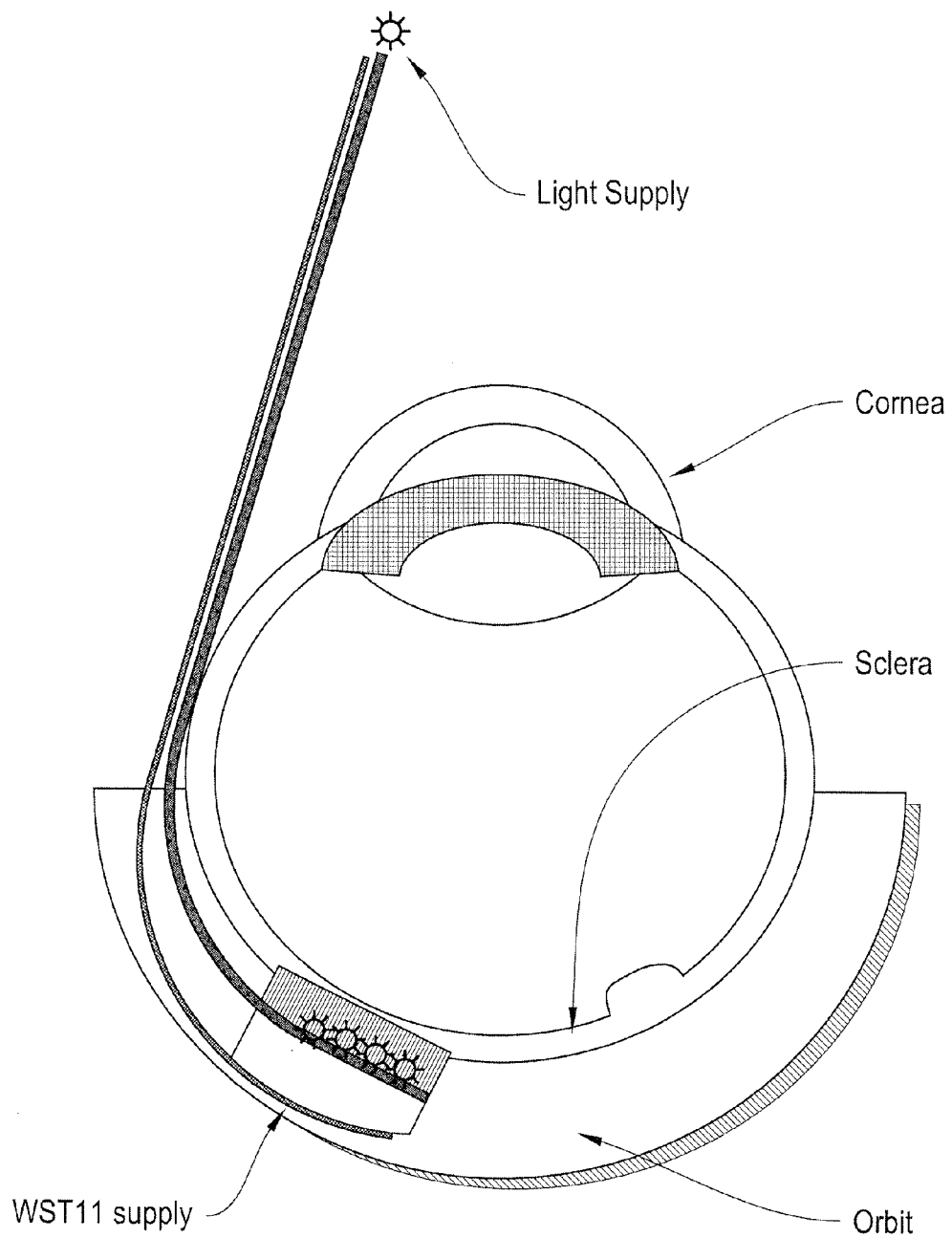
Figure 18A:
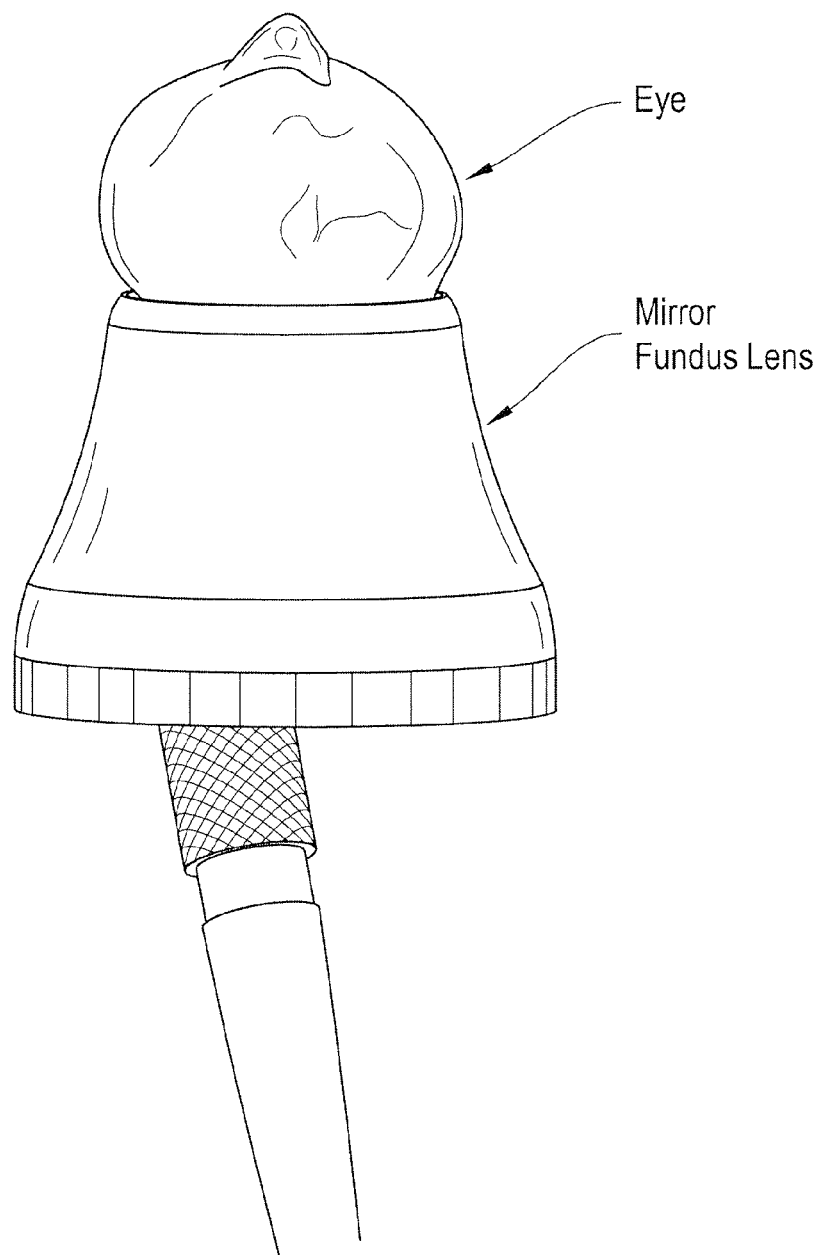
FIGS. 18A-18C are illustrations of the three mirror fundus lens apparatus used for NIR illumination of the posterior treated sclera of a rabbit eye by illuminating the anterior cornea.
Figure 18B:
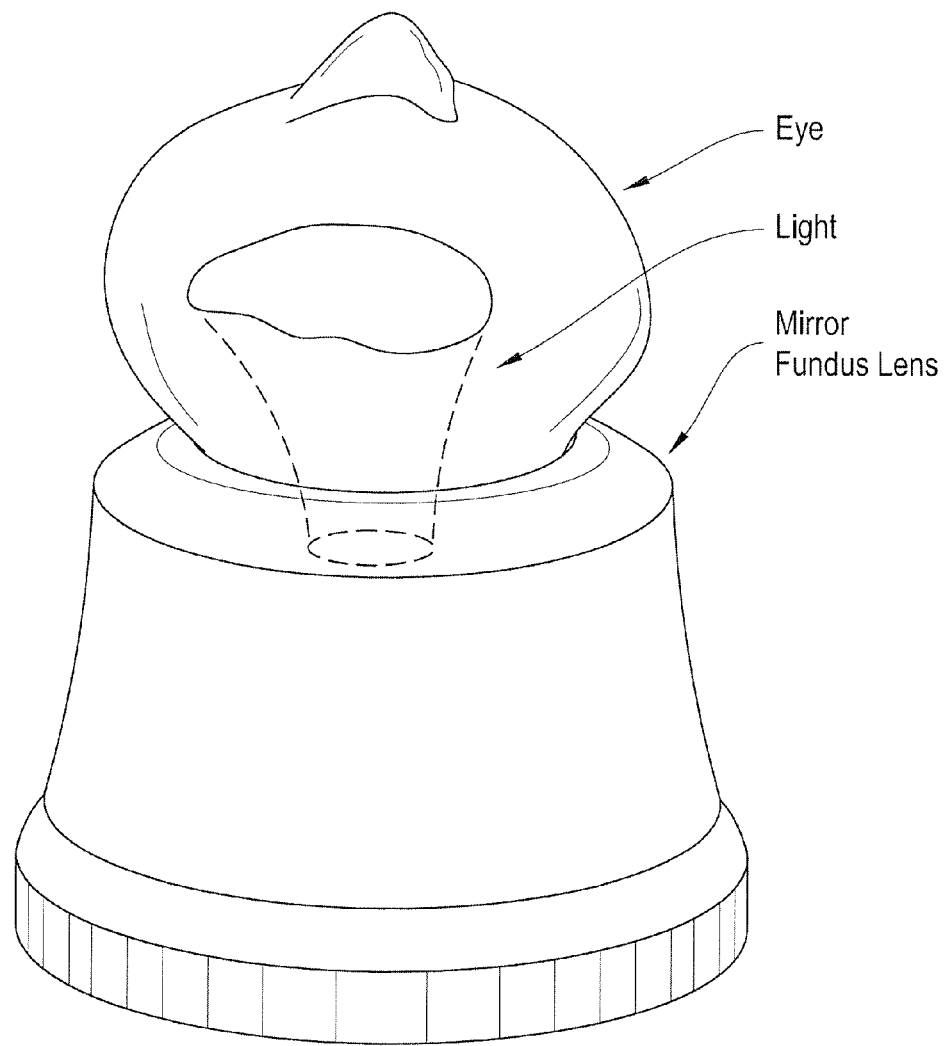
Figure 18C:
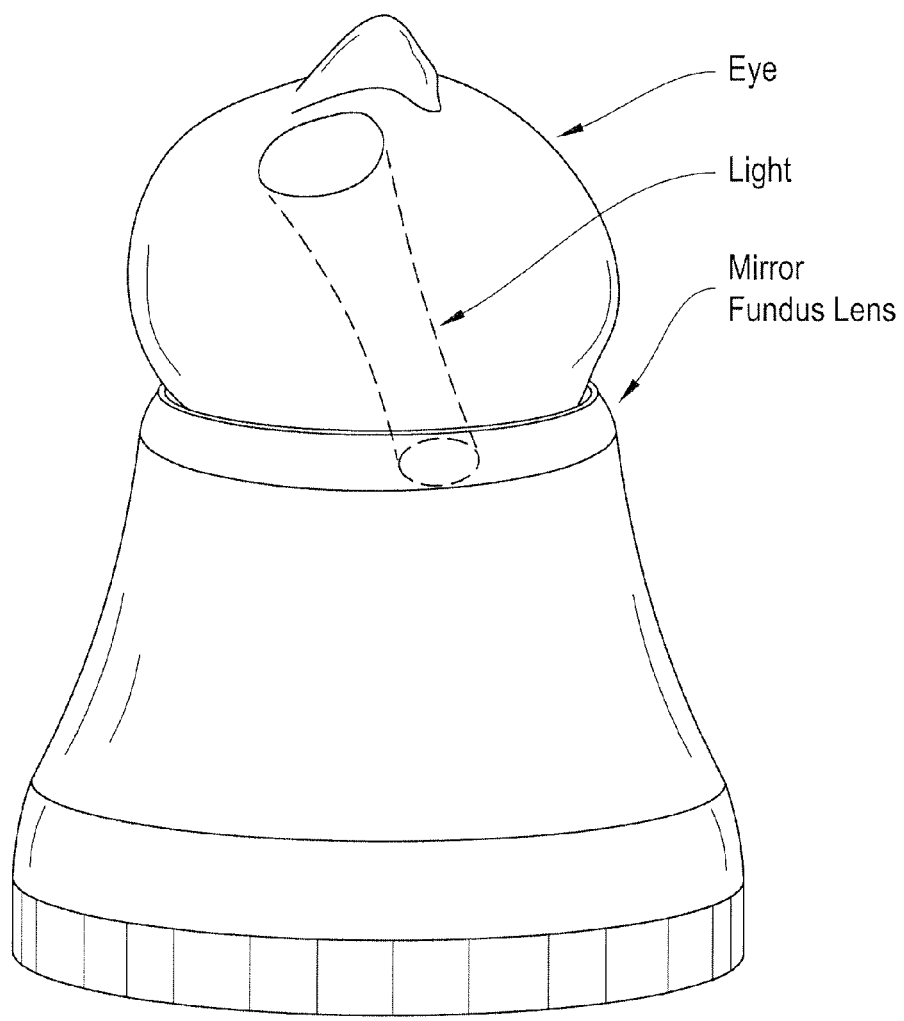

Biomechanical Testing of Rabbit Sclera Treated Ex Vivo with WST11-S and NIR Illumination Through the Anterior Eye Segment The inventors hypothesized that since tissues are fairly transparent to illumination at 755-820 nm, it should be possible to deliver sufficient illumination to the posterior sclera by NIR illumination through the cornea and anterior segment of the eye using either the three mirror fundus lens apparatus shown in FIGS. 18A-18C, or by illuminating the cornea through an indirect ophthalmoscope using the apparatus described in FIG. 17B.

Six eyes of three rabbits were enucleated. The posterior eye area up to the equatorial line was incubated using an eye cap with 2.5 mg/ml solution of WST11 in saline pH 7.3 for 20 minutes and then illuminated by NIR illumination through the anterior cornea using a diode laser (755 nm, 0.5 W) and three mirror fundus lens (FIGS. 18A-18C) for 30 minutes. Strips of sclera were cut and tested as described in Materials and Methods.

Figure 16A:
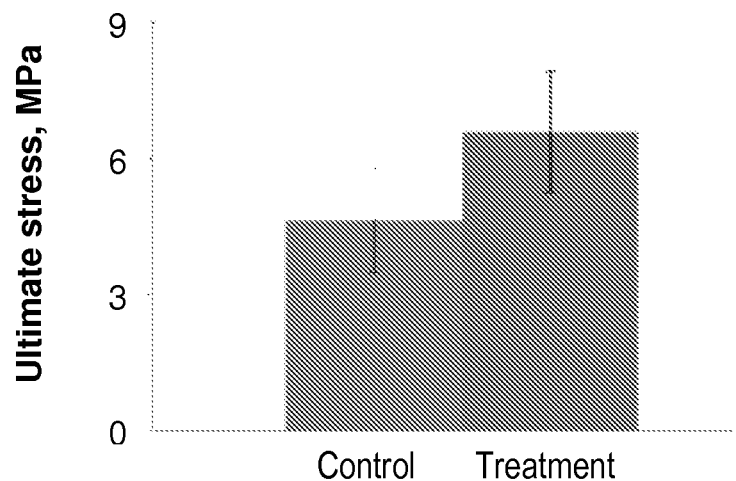
FIGS. 16A-16B are graphs presenting ex vivo stress-strain measurements values of upper equatorial sclera stiffness in ultimate stress units (15A) and Young's modulus (15B) of corneas after 20-min incubation with WST11 followed by 30-min NIR illumination (755 nm, 10 mW/cm$^2$) through the anterior cornea. Control—untreated lower equatorial sclera.
Figure 16B:
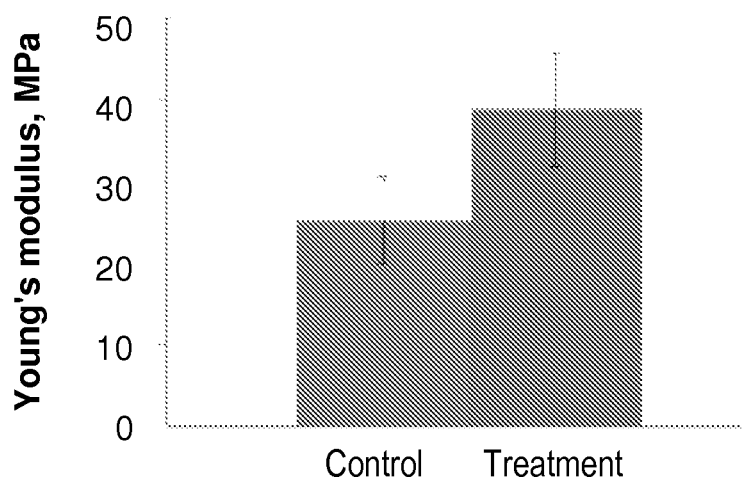

The measurements demonstrated an increase in the stiffness of the treated sclera. The mean maximal stress in control sclera was 4.65±1.15 MPa. The mean maximal stress in WST11/NIR treated corneas was 6.59±1.32 MPa (42% increase). The mean Young's modulus in control sclera was 25.25±5.30 MPa. The mean Young's modulus in WST11/NIR treated sclera was 38.83±6.89 MPa (54% increase). The results are shown in FIGS. 16A-16B

Example 14

In Vivo Sclera Stiffening with Illumination Through the Anterior Segment

In vivo scleral stiffening while avoiding retinal and eye orbit toxicity is achieved as follows:

Impregnation of the photosensitizer (a Bchl derivative) into the sclera is performed by inserting a sub-tenon glide through openings in the limbal conjunctiva in 4 quadrants. The inner distal 10 mm of the glide is porous and contains a reservoir of the test compound. This reservoir is connected by a tube that runs outside along the glide. After placing the glide attached to the sclera, the tube is connected to a syringe or pump, and the test compound reservoir is injected to impregnate the sclera. The sensitizer concentration and time of exposure is a priori optimized via ex-vivo measurements of enucleated rabbit eyes using fluorescence spectroscopy of frozen histological sclera sections as described in Example 11 above. If required, dextran or sucrose solutions are used to optimize penetration depth.

The retina safety depends on the traversing light energy. In preclinical and Phase II clinical trials of vascular targeted PDT with WST11, the inventors have shown that illumination of retina by 50-70 J (82-120 sec at 600 mW/cm$^2$) proved safe. Consequently, the treatment energy is set at the range of 5-12 J (10-20 mW/cm$^2$ for 20-10 min) for which minimal morbidity of the retina is expected.

Using the optimized parameters Bchl-S or Bchl-D is applied as described above followed by 755-nm frontal illumination at an optimized laser power output in the range of 20-250 mW to deliver an a priori optimized light intensity at the posterior segment of the eye. The illumination is performed using a NIR laser with He—Ne aiming beam through Goldmann 3 mirror fundus lens or NIR laser attached to an indirect ophthalmoscope with He—Ne aiming beam. One month after the treatment the rabbits are euthanized and the eyes are enucleated. Treatment success is assessed by strain-stress measurements of scleral strips excised from the superior and the inferior sclera of the treated eyes compared to the matching sclera of non-treated fellow eyes.

Example 15

In Vivo Sclera Stiffening with Illumination Through the Anterior Segment

In vivo scleral stiffening while avoiding retinal and eye orbit toxicity is achieved as described in Example 14, but the photosensitizer delivered to the sclera via a Merocel® sponge attached to the glide inserted through openings in the limbal conjunctiva, instead of using a porous glide to deliver the photosensitizer.

Example 16

In Vivo Sclera Stiffening with Illumination Through the Anterior Segment

In vivo scleral stiffening is achieved as described in Example 14, but illumination is applied externally by insertion of a glide connected to optical fiber through the limbal conjunctiva openings as illustrated in (FIG. 17B). This glide is designed to spread a diffuse light directed towards the sclera; it is opaque in its orbital aspect. The illumination glide is connected to a NIR laser or LED source to deliver the NIR light. Both impregnation and illumination glides are marked with a millimetric ruler to verify insertion depth. Position of illumination glide can be monitored during light delivery by fundoscopy or fundus imaging.

An alternative glide that is used for in vivo scleral stiffening is a glide designed as a combined unit for both drug and illumination delivery.

REFERENCES

Ashur I, et al. 2009, "Photocatalytic generation of oxygen radicals by the water-soluble bacteriochlorophyll derivative WST11, noncovalently bound to serum albumin", *J Phys Chem.*, 113:8027-37.

Avila M Y, Navia J L, 2010, "Effect of genipin collagen crosslinking on porcine corneas", *J Cataract Refract Surg.*, 36:659-664.

Berdugo M et al. 2008, "Evaluation of the new photosensitizer stakel (WST-11) for photodynamic choroidal vessel occlusion in rabbit and rat eyes", *Inv Ophthalmol Vis Sci.* 49:1633-1644.

Bourges J L et al., 2006, "PDT of corneal neovessels using a new hydrosoluble photosensitizer (WST11)", *Acta Ophthalmol Scand.*, 84(S 239:41): 352.

Brandis A, Mazor O, Neumark E, Rosenbach-Belkin V, Salomon Y, Scherz A. 2005, "Novel water-soluble bacteriochlorophyll derivatives for vascular-targeted photodynamic therapy: synthesis, solubility, phototoxicity, and the effect of serum proteins", *Photochem Photobiol.*, 81:983-993.

Elsheikh A, Wang D, Brown M, Rama P, Campanelli M, Pye D, 2007, "Assessment of corneal biomechanical properties and their variation with age", *Curr Eye Res.*, 32:11-19.

Hafezi F, Kanellopoulos J, Wiltfang R, Seiler T. 2007, "Corneal collagen crosslinking with riboflavin and ultraviolet A to treat induced keratoectasia after laser in situ keratomileusis" *J Cataract Refract Surg.*, 33:2035-2040.

Hafezi F, Mrochen M, Iseli H P, Seiler T. 2009, "Collagen crosslinking with ultraviolet-A and hypoosmolar riboflavin solution in thin corneas", *J Cataract Refract Surg.*, 35:621-624.

Kato Y, Uchida K, Kawakishi S. Aggregation of collagen exposed to UVA in the presence of riboflavin: a plausible role of tyrosine modification. *Photochem Photobiol.* 1994; 59:343-349.

Knox Cartwright N E, Tyrer J R, Marshall J, 2010, "Age-related differences in the elasticity of the human cornea", *Invest Ophthalmol Vis Sci.*, 52:4324-4329.

Lepor H. 2008, "Vascular targeted photodynamic therapy for localized prostate cancer", *Rev Urol.*, 10:254-261.

Letko E, Majmudar P A, Forstot S L, Epstein R J, Rubinfeld R S, 2011, "UVA-light and riboflavin-mediated corneal collagen cross-linking", *Int ophthalmol clin.*, 51:63-76.

Liu K et al. 2004, "Superoxide, hydrogen peroxide and hydroxyl radical in D1/D2/cytochrome b-559 Photosystem II reaction center complex", *Photosynthesis Research.*, 81:41-47.

Mazor O. et al. 2005, "WST11, A novel water-soluble bacteriochlorophyll derivative; cellular uptake, pharmacokinetics, biodistribution, and vascular targeted photodynamic activity against melanoma tumors", *Photochem Photobiol.*, 81:342-345.

Moore C M, Pendse D, Emberton M. 2009, "Photodynamic therapy for prostate cancer-a review of current status and future promise", *Nat Clin Pract Urol.*, 6:18-30.

Raiskup-Wolf F, Hoyer A, Spoerl E, Pillunat L E. 2008, "Collagen cross-linking with riboflavin and ultraviolet-A light in keratoconus: long-term results", *J Cataract Refract Surg.* 34:796-801

Søndergaard A P, Hjortdal J, Breitenbach T, Ivarsen A, 2010, "Corneal distribution of riboflavin prior to collagen cross-linking", *Curr Eye Res.*, 116:121-135.

Spence D J, Peyman G A. 1976, "A new technique for the vital staining of the corneal endothelium", *Inv Ophthalmol Vis Sci.*, 15: 1000-1002.

Spoerl E, Mrochen M, Sliney D, Trokel S, Seiler T. 2007, "Safety of UVA-riboflavin cross-linking of the cornea", *Cornea*, 26:385-389.

Trachtenberg J et al. 2007, "Vascular targeted photodynamic therapy with palladium-bacteriopheophorbide photosensitizer for recurrent prostate cancer following definitive radiation therapy: assessment of safety and treatment response", *J Urol.*, 178:1974-1979.

Vakrat-Haglili Y et al., 2005, "The microenvironment effect on the generation of reactive oxygen species by Pd-Bacteriopheophorbide", *J Am Chem Soc.*, 127:6487-6497.

Wollensak G, 2010(a) "Histological changes in human cornea after cross-linking with riboflavin and ultraviolet A", Letter to the editor. *Acta Ophthalmol.* 88:e17-18.

Wollensak G, Aurich H, Wirbelauer C, Saadettin S. 2010(b), "Significance of the riboflavin film in corneal collagen crosslinking", *J Cataract Refract Surg.*, 36:114-120.

Wollensak G, Spoerl E, Reber F, Pillunat L, Funk R. 2003(c), "Corneal endothelial cytoxicity of riboflavin/UVA treatment in vitro", *Ophthalmic Res.*, 35:324-328.

Wollensak G, Spoerl E, Reber F, Seiler T. 2004(a) "Keratocyte cytotoxicity of riboflavin/UVA-treatment in vitro", *Eye*, 18:718-722.

Wollensak G, Spoerl E, Seiler T. 2003(a) "Riboflavin/ultraviolet-A-induced collagen crosslinking for the treatment of keratoconus", *Am J Ophthalmol*, 135:620-627.

Wollensak G, Spoerl E, Wilsch M, Seiler T. 2003(b) "Endothelial cell damage after riboflavin-ultraviolet-A treatment in the rabbit", *J Cataract Refract Surg.* 29:1786-1790.

Wollensak G, Spoerl E, Wilsch M, Seiler T. 2004(b) "Keratocyte apoptosis after corneal collagen cross-linking using riboflavin/UVA treatment", *Cornea.* 23:43-49.

The invention claimed is:

1. A method of treating keratoconus by photodynamic therapy (PDT), said method comprising the steps of:
   (i) administering to an eye of an individual in need thereof an effective amount of Palladium $3^1$-oxo-15-methoxycarbonylmethyl-rhodobacteriochlorin $13^1$-(2-sulfoethyl)amide, or a pharmaceutically acceptable salt thereof, and
   (ii) irradiating the eye of said individual with light at a red or near infrared (NIR) wavelength.

2. The method according to claim 1, wherein the pharmaceutically acceptable salt thereof is a potassium salt of Palladium $3^1$-oxo-15-methoxycarbonylmethyl-rhodobacteriochlorin $13^1$-(2-sulfoethyl)amide.

3. The method according to claim 2, wherein the potassium salt of Palladium $3^1$-oxo-15-methoxycarbonylmethyl-rhodobacteriochlorin $13^1$-(2-sulfoethyl)amide is Palladium $3^1$-oxo-15-methoxycarbonylmethyl-rhodobacteriochlorin $13^1$-(2-sulfoethyl)amide dipotassium salt.

4. The method according to claim 1, wherein the pharmaceutically acceptable salt thereof is a salt of Palladium $3^1$-oxo-15-methoxycarbonylmethyl-rhodobacteriochlorin $13^1$-(2-sulfoethyl) amide with a monovalent alkaline metal or ammonium.

5. The method according to claim 4, wherein the pharmaceutically acceptable salt thereof is a salt of Palladium $3^1$-oxo-15-methoxycarbonylmethyl-rhodobacteriochlorin $13^1$-(2-sulfoethyl) amide with a monovalent alkaline metal selected from the group consisting of potassium, sodium and lithium.

* * * * *